(12) United States Patent
Le et al.

(10) Patent No.: US 7,037,657 B2
(45) Date of Patent: May 2, 2006

(54) MUTANT NURR1 GENE IN PARKINSON'S DISEASE

(75) Inventors: Wei-Dong Le, Houston, TX (US); Demetrios K. Vassilatis, Seattle, WA (US)

(73) Assignee: Baylor College of Medicine, Houston, TX (US)

( * ) Notice: Subject to any disclaimer, the term of this patent is extended or adjusted under 35 U.S.C. 154(b) by 539 days.

(21) Appl. No.: 10/205,951

(22) Filed: Jul. 26, 2002

(65) Prior Publication Data

US 2003/0119026 A1  Jun. 26, 2003

Related U.S. Application Data

(60) Provisional application No. 60/308,294, filed on Jul. 27, 2001.

(51) Int. Cl.
*C12Q 1/68* (2006.01)
*C07H 21/02* (2006.01)
*C07H 21/04* (2006.01)

(52) U.S. Cl. .................. 435/6; 435/91.2; 536/23.1; 536/23.5

(58) Field of Classification Search .................. 435/6, 435/91.1, 91.21, 91.5; 536/23.5, 24.31
See application file for complete search history.

(56) References Cited

U.S. PATENT DOCUMENTS

| | | | |
|---|---|---|---|
| 6,284,539 B1 | 9/2001 | Bowen et al. | |
| 6,312,949 B1 | 11/2001 | Sakurada et al. | |
| 6,395,546 B1 | 5/2002 | Zobel et al. | |

OTHER PUBLICATIONS

Mages et al. Molecular Endocrinology. 1994. 8: 1583-1591.*
McEvoy et al. The Journal of Immunology. 2002. 168: 2979-2987.*
Nichols et al. Movement Disorders. 2004 19: 649-655.*
Tan et al. Neuroscience Letters. 2003. 347: 139-142.*
Nichols et al. Neurology. Mar. 2003. 60: A281-282.*
Le, Wei-dong, et al.; Mutations in NR4A2 associated with familial Parkinson disease; Nature Genetics 33:85-89, Jan. 2003.
Le, W., et al.; Corrigendum—Mutations in NR4A2 associated with familial Parkinson disease; Nat. Genet. 33:214, Feb. 2003.
Zetterstrom, Rolf H., et al.; Dopamine Neuron Agenesis in Nurr1-Deficient Mice; Science 276:248-250, Apr. 11, 1997.
Zetterstrom, Rolf H., et al.; Cellular expression of the immediate early transcription factors Nurr1 and NGFI-B suggests a gene regulatory role in several brain regions including the nigrostriatal dopamine system; Molecular Brain Research 41:111-120, 1996.
Wallen, Asa, et al.; Fate of Mesencephalic AHD2—Expressing Dopamine Progenitor Cells in Nurr1 Mutant Mice; Experimental Cell Research 253:737-746, 1999.
Torii, T., et al.; Organization of the human orphan nuclear receptor Nurr1 gene; Gene 230:255-232. 1999.
Saucedo-Cardenas, Odila, et al.; Comparative Distribution of NURR1 and NUR77 Nuclear Receptors in the Mouse Central Nervous System; Journal of Molecular Neuroscience; 7:51-63, 1996.
Saucedo-Cardenas, Odila, et al.; Nurr1 is essential for the induction of the dopaminergic phenotype and the survival of ventral mesencephalic late dopaminergic precursor neurons; Proc. Natl. Acad. Sci. USA (Neurobiology) 95:4013-4018, Mar. 1998.
Sakurada, Kazuhiro, et al.; Nurr1, an orphan nuclear receptor, is a transcriptional activator of endogenous tyrosine hydroxylase in neural progenitor cells derived from the adult brain; Development 126:4017-4026, 1999.
Sacchetti, Paola, et al.; Nurr1 enhances transcription of the human dopamine transporter gene through a novel mechanism; Journal of Neurochemistry 76:1565-1572, 2001.

(Continued)

*Primary Examiner*—Carla J. Myers
(74) *Attorney, Agent, or Firm*—Fulbright & Jaworski, LLP

(57) ABSTRACT

The identification of mutations in NURR1 provides molecular tools for the development of diagnostic, prophylactic and therapeutic agents for Parkinson's Disease. In specific embodiments, two point mutations are identified in exon 1 of the NURR1 gene in 10/107 (9.3%) cases of familial Parkinson's disease (PD). The mutations reduce NURR1 gene expression (mRNA and protein levels) by 87–95% and decrease tyrosine hydroxylase (a rate-limited dopamine synthesis enzyme) gene expression in vitro. It is also demonstrated that in vivo NURR1 mRNA levels in the lymphocytes from the PD patients with the exon 1 mutation are reduced by 68–84%, and in over 50% sporadic PD patients the NURR1 mRNA levels in lymphocytes are significantly reduced. A homozygous polymorphism is identified in intron 6 of NURR1 that correlates with the presence of Parkinson's disease. A splicing variant in NURR1 exon 5 is identified.

14 Claims, 11 Drawing Sheets

OTHER PUBLICATIONS

Le, Wei-dong, et al.; Reduced Nurr1 Expression Incresases the Vulnerability of Mesencephalic Dopamine Neurons to MPTP-Induced Injury; J Neurochem. 73:2218-2221, 1999.

Le, Wei-dong, et al.; Selective Agenesis of Mesencephalic Dopaminergic Neurons in Nurr1-Deficient Mice; Experimental Neurology 159:451-458, 1999.

Castillo, Susan O., et al.; Organization, Sequence, Chromosomal Localization, and Promoter Identification of the Mouse Orphan Nuclear Receptor Nurr1 Gene; Genomics 41:250-257, 1997.

Buervenich, Silvia, et al.; Brief Research Communicatin—NURR1 Mutations in Cases of Schizophrenia and Manic-depressive Disorder; American Journal of Medical Genetics (Neuropsychiatric Genetics) 96:808-813, 2000.

Ichinose, Hiroshi, et al.; Molecular cloning of the human Nurr1 gene: characterization of the human gene and cDNAs; Gene 230:233-239, 1999.

Le, Wei-dong, et al.; Polymorphism at Intron 6 of Nurr1 Gene Is Associated with Familial Parkinson Disease; Neurology 56(3):A120, Apr. 2001.

* cited by examiner

Dominant form:Exon5-6
<u>TCTCCCCTTCGCCCCCGGTGAGTCTGATCAGTGCCCTCGTCAGGGCCCATGTCGAC</u>
Exon 5
<u>TCCAACCCGGCTATGACCAGCCTGGACTATTCCAGGTTCCAGGCGAACCCTGACTA</u>
<u>Exon 5</u>                                              Exon 6
Splicing variant:Exon5-6
<u>TCTCCCCTTCGCCCCCG------------------------------</u>
Exon 5

<u>---------------------------TTCCAGGCGAACCCTGACTA</u>
Exon 5                                                Exon 6

FIG. 8

MUTANT NURR1 GENE IN PARKINSON'S DISEASE

CROSS-REFERENCE TO RELATED APPLICATIONS

This application claims priority to U.S. Provisional Patent Application Ser. No. 60/308,294, filed Jul. 27, 2001, which is incorporated by reference herein in its entirety.

STATEMENT REGARDING FEDERALLY SPONSORED RESEARCH OR DEVELOPMENT

The present invention was funded in part by government grant NIH RO-1 NS 40370-01 from the National Institutes of Health. The federal government may have certain rights in the invention.

FIELD OF THE INVENTION

The present invention relates to the field of human genetics, and in particular, to the identification of a mutant NURR1 polynucleotide implicated in Parkinson's Disease.

BACKGROUND OF THE INVENTION

The identification of genes contributing to the etiology of Parkinson's disease (PD) is very complicated. The disorder, in all likelihood, is not a disease with a single cause. A growing body of evidence indicates that PD might be caused by genetic defects and/or by as yet undefined environmental insults acting on genetically predisposed individuals in the process of aging (Langston, 1998; Goldman et al., 1998).

Genetic factors have been linked to familial PD (fPD) or parkinsonism by the demonstration of mutations in the α-synuclein gene (Polymeropoulos et al., 1997), in the parkin gene (Kitada et al., 1998), in the tau gene (Clark et al., 1998), and in several undefined genes mapped to 1p35 (Valente et al, 2001), 1p36 (Van Duijn et al, 2001), 2p13 (Gasser et al., 1998), 4p15.7 (Farrer et al., 1998), and 4p14 (Leroy et al., 1998) and 12p11.2–q13.1 (Funayama et al., 2002). Defective or decreased expression of genes that regulate the development and survival of midbrain dopaminergic (DAergic) neurons may be an important risk factor associated with PD.

The evidence for genetic factors in sporadic PD (sPD) was initially quite controversial (Langston, 1998), but there is now increasing evidence suggesting a significant role for genetic factors in determining PD susceptibility. Recent studies using sensitive PET imaging to detect subclinical nigral dysfunction have shown a higher concordance among monozygotic than dizygotic twins (Piccini et al., 1999). In addition, the combination of a certain α-synuclein promoter polymorphism within the APE4 allele has been suggested to elevate the risk of sporadic PD (Kruger et al., 1999). The data, taken together, suggest strongly that genetic susceptibility factors contribute, either directly or indirectly, to the onset of PD.

NURR1 is highly expressed in the midbrain DAergic neurons (Saucedo-Cardenas et al., 1997). Furthermore, NURR1 is essential for the development of DAergic neurons in the midbrain. Depletion of Nurr1 results in a selective agenesis of mesencephalic DAergic neurons (Zetterstrom et al., 1997; Castillo et al., 1997; Saucedo-Cardenas et al., 1998, Le et al., 1999). Nurr1 is also a transcriptional activator of endogenous tyrosine hydroxylase, a key DA synthesis enzyme (Sakurada et al, Development, 1999), and an enhancer of DA transporter transcription (Sacchetti et al, J Neurochem, 2001).

NURR1 is critical for the survival of late DAergic precursor neurons (Saucedo-Cardenas et al., 1998, Wallen et al., 1998). In the absence of NURR1 during the late stage of development in the NURR1 null mutant mice, the midbrain DA precursor cells degenerate and die of apoptosis. Furthermore, acutely reduced expression of NURR1 (e.g., by antisense knockdown) impairs the expression of the DAergic phenotype in adult SN (Apostolakjs et al., 2002). Reduction of NURR1 expression (e.g. in NURR1+/− mice) confers increased susceptibility to MPTP-induced nigral injury (Le et al., 1999), and decreased DA transmission in the nigral-striatal pathway (Zetterstrom et al., 1997).

The human NURR1 (SEQ ID NO: 1) (also known as NOT/TINUR/RNR-1/HZF-3, a homolog of rodent Nurr1) has been mapped on chromosome $2q^{22-23}$ (Mages et al., 1994, and is approximately 8.3 kb long and consists of eight exons and seven introns (Ichinose et al., 1999). The NURR1 gene is highly conserved, and the expression of the gene is mediated by various transcriptional factors and binding sites in the promoter region (Castillo et al., 1997). Wild type NURR1 expressed as a protein having the amino acid sequence of SEQ ID NO: 2.

In addition, NURR1 may have at least two splicing variants in the human brain (Ichinose et al., 1999). Different deletion mutants were constructed in the promoter region of NURR1 and in the transcriptional initiation sites. The results suggested that transcription regulators, alternative splicing and the selective use of the transcription initiation site may control NURR1 expression and function (Torii et al., 1999). Furthermore, missense mutations in exon 3 of NURR1 have been linked to schizophrenia and manic-depressive disorder (Buervenich et al., 2000). Since the dysfunction of DAergic neurons is one of the major factors in PD, a preventive approach may be contrived by studying whether the disease is correlated with NURR1.

U.S. Pat. No. 6,284,539 describes methods to direct multipotential precursor cells from the central nervous system to adopt a dopaminergic cell fate. Generally, NURR1 is introduced into central nervous system (CNS) stem cells. In specific embodiments, in vitro neural populations enriched in dopaminergic cells for transplantation in Parkinson's Disease or other neurological disorders are generated. In other specific embodiments, there are methods for generating tyrosine hydroxylase expressing cells in a culture of mammalian CNS stem cells by culturing mammalian CNS stem cells in vitro, introducing a NURR1 polynucleotide that is expressed, incubating the mammalian CNS stem cells, and identifying tyrosine hydroxylase expressing cells in the culture.

U.S. Pat. No. 6,312,949 is related to a cell comprising an exogenous NURR1 nucleic acid that encodes an amino acid sequence that is expressed and induces tyrosine hydroxylase expression within the cell. In specific embodiments, the cells can be used to treat catecholamine-related deficiencies associated with disease states such as Parkinson's disease.

U.S. Pat. No. 6,395,546 is directed to methods for generating dopaminergic neurons in vitro from embryonic and adult central nervous system cells. Specifically, these cells are isolated, cultured in vitro and stimulated to differentiate into dopaminergic neurons by down-regulating COUP-TFI and/or COUP-TFII expression or increasing NOT1 expression.

Zetterstrom et al. (1996) describe in situ hybridization of NURR1 mRNA in the developing and adult mouse and rat in several regions during early central nervous system (CNS) development, suggesting it is involved in the development and maturation of specific sets of CNS neurons.

Finally, Buervenich et al. (2000) describe that direct sequencing of genomic DNA revealed two different missense mutations in the third exon of NURR1 in two schizophrenic patients and another missense mutation in the same exon in an individual with manic-depressive disorder. All three mutations caused a similar reduction of in vitro transcriptional activity of NURR1 dimers of about 30–40%. Neither of these amino acid changes, nor any sequence changes whatsoever, were found in patients with Parkinson's disease or control DNA material of normal populations.

Thus, there remains an absence in the art for association between NURR1 mutations and the etiology of Parkinson's disease.

SUMMARY OF THE INVENTION

The present invention is directed to a system(s), method(s), and composition(s) that comprise a defective NURR1 associated with Parkinson's disease and/or symptoms similar thereto.

The present inventors recognized that NURR1, a member of nuclear receptor/retinoic acid receptor superfamily, is be a candidate gene for PD susceptibility. Subsequent investigation of NURR1 revealed the potential for novel therapies to treat Parkinson's disease and other DAergic dysfunction related disorders using genetic-pharmacology directed to NURR1 and mutants thereof.

To investigate whether the genetic variations of the NURR1 gene may occur in familial PD, and in some embodiments in sporadic PD, and to determine the association, if any, between genetic variations and the risk of PD, the entire coding and non-coding regions of 8 exons of the NURR1 gene were analyzed using genomic DNA from 107 familial PD and 120 sporadic PD as compared to 221 age-matched normal controls (NC). Two novel point mutations at exon 1 of the NURR1 gene in 12/107 fPD patients were found, and these mutations reduced NURR1 gene expression in vitro by 87–95%. Further, direct assay of mRNA levels of NURR1 from PD patient lymphocytes revealed a substantial reduction of NURR1 expression in fpD patients (68–84% reduction) having the exon1 mutations in the NURR1 gene and in 11/19 sPD patients (30–65%), as compared with 24 age-matched normal controls. Additionally, a homozygous polymorphism in intron 6 of the NURR1 gene was also found to be closely associated with fPD and sPD. The data provides insight into the etiology and molecular mechanisms leading to mesencephalic dopaminergic cell death in PD and facilitates the development of novel therapeutic treatments for the disease.

The present invention includes DNA sequences that encode mutant versions of the human Nurr1 protein, as well as DNA sequences that result in a polymorphism at the NURR1 gene locus. In all of these cases, the uses of the sequences include, but are not limited to, treatment of PD.

One of the sequences of the present invention that may be responsible for, or contribute to the onset of, PD is a segment of the human NURR1 gene that contains a mutation at base pair position −291 (referred to herein as −291-T-del) relative to the initiator AUG codon. This deletion results in a dramatic reduction in NURR1 expression, possibly through inactivation of the transcriptional regulatory elements or by affecting NURR1 mRNA stability. Homologs of this mutant oligonucleotide sequence may also have important roles in the investigation of PD. Since in specific embodiments treatment of PD ultimately involves the inactivation or compensation for the presence of the mutant NURR1 gene, versions of the instant mutant oligonucleotide are useful as probes to detect relevant sequences. For example, the relevant sequences may be mRNA, DNA, a primer or a probe containing the sequence, or an antisense version of the sequence.

Treatment of PD may encompass the expression, such as by administration, of the oligonucleotide containing the aforementioned point mutation. Therefore, expression vectors containing any of the versions of the oligonucleotide sequence (i.e. antisense, homologues, etc.) are useful.

The presence of the −291-T-del mutant gene in an individual may constitute a risk factor for PD because the reduction in NURR1 expression associated with the mutation (and all the mutations herein disclosed) leads to dopaminergic dysfunction that gives rise to the Parkinson's phenotype. Therefore, any sequence related to the gene sequence, or any molecules that activate the NURR1 gene and subsequently alter the gene expression, may be useful in the diagnosis, treatment or prevention of PD and other dopaminergic dysfunction-related disorders. Relevant sequences may include the full-length mutant gene or relevant portions thereof, in addition to homologs and antisense versions of the gene or portions thereof. Relevant portions of the mutant gene include nucleotide sequences that span the region of the gene containing the respective mutation of the present invention. Expression vectors containing such relevant sequences have medical applications.

Given the correlation of the mutant NRR1 gene with PD, various types of gene therapy are contemplated by the present invention. The embodiments of the present invention for detecting, preventing the onset of, or treating PD in an individual having the mutated NURR1 gene include administering wild-type Nurr1 protein, or any molecules that activate or alter NURR1 expression, to the individual. Blocking the transcription or translation (possibly by adding an antisense oligonucleotide) of the mutant Nurr1 protein in the individual may also be useful in this regard. Inhibition of the biological activity of the mutant protein (possibly by adding either an agonist or an antagonist of the mutant Nurr1) is another embodiment of the present invention.

Another sequence that may be responsible for, or contribute to, the onset of PD is a segment of the human NURR1 gene that contains a mutation at base pair position −245 (relative to the initiator AUG codon) which results in a substitution of a G for a T (referred to herein as −245T-G-sub). This mutation in exon 1 of the NURR1 gene causes a dramatic reduction in NURR1 expression, possibly through inactivation of the transcriptional regulatory elements or by affecting the mRNA stability. Homologs of this substitution mutant DNA sequence may have roles in the detection of PD. Relevant sequences that may be used for isolation of the entire mutant gene, or relevant portions thereof, may be mRNA, DNA, a primer and/or a probe containing the mutant oligonucleotide sequence, or an antisense version of the sequence.

The −245T-G-sub mutant gene may constitute a risk factor for PD. Since treatment of PD may ultimately involve the inactivation, or compensation for the presence of the mutant gene, various versions of the mutant gene are useful in the diagnosis or treatment or prevention of PD. These related sequences may include homologs and antisense versions of the full-length mutant gene. Additionally, molecules that activate the NURR1 gene or alter the gene expression are medically useful.

Expression vectors containing either the full-length mutant gene or the antisense version have medical applications.

As in the case of the NURR1 deletion mutant, the substitution mutant is used to prevent, delay the onset of, and/or treat PD. The treatments may encompass methods as described for the deletion mutant.

Related to the expression vectors is that the mutant NURR1 gene present in an individual who suffers from PD is treated by administration of functional Nurr1 protein to the individual, particularly at a level sufficient to avoid deleterious effects of insufficient NURR1. Alternatively, one can inhibit the transcription or translation of the mutant NURR1 gene in the individual. Inhibition of the biological activity of the mutant Nurr1 protein is also a useful medical strategy.

A third variation in the NURR1 gene that correlates with PD is a homozygous polymorphism mutant in intron 6, which interrupts the exon encoding the ligand-binding domain of NURR1. Oligonucleotide sequences that correspond to this region of the NURR1 gene, homologs to this oligonucleotide, DNA regions corresponding to the oligonucleotide and primers, and ligands and/or probes designed based on this oligonucleotide sequence are useful in assessing the risk of PD.

A fourth variation in the NURR1 gene is a splicing variant in exon 5. RT-PCR sequence analysis of an exon 5–7 fragment reveals a 75 nucleotide deletion in the middle of exon 5 in some individuals of the study population.

A specific method for predicting the predisposition to PD, or for detecting the presence of PD involves isolation of the genomic DNA from an individual, digestion with the restriction enzyme BseR1 and analysis of the digestion products.

Expression vectors comprising the polymorphous oligonucleotide and antisense versions of the polymorphous oligonucleotide sequence have potential medical applications.

Nucleotide sequences comprising the full-length version of the NURR1 mutant gene, or relevant portions thereof, containing the polymorphism in intron 6, homologs of this mutant gene, primers and/or probes derived from the full-length gene or its relevant portions, and/or antisense versions of the gene or its relevant portions are used in gene therapy for PD. Additionally, expression vectors comprising such sequences may be useful in this regard.

Treatment of PD or other dopaminergic dysfunction may involve strategies such as inhibition of expression of the mutant gene, administration of normal amounts of Nurr1 protein, inactivating the gene product that results from transcription or translation of the mutant gene, administration of any molecule that activates or alters the expression of the NURR1 gene and combinations of such treatments.

Therefore, in one embodiment, the present invention may be summarized as an oligonucleotide sequence, and its homologs, which has a sequence selected from the following group: (a) the sequence of SEQ ID NO: 1, except that the T at position −291 is deleted; (b) a subsequence of SEQ ID NO: 1, where the subsequence is 8 to 9824 nucleotides long and includes position −291 of SEQ ID NO: 1, except that the T at position −291 of SEQ ID NO: 1 is deleted; (c) a sequence that is complementary to that of the sequence specified in (a); and (d) a sequence that is complementary to that of the subsequence specified in (b).

In another embodiment, the present invention may be summarized as an oligonucleotide sequence, and its homologs, which has a sequence selected from the following group: (a) the sequence of SEQ ID NO: 1, except that the G at position −245 is replaced with T; (b) a subsequence of SEQ ID NO: 1, where the subsequence is 8 to 9824 nucleotides long and includes position −245 of SEQ ID NO: 1, except that the G at position −245 is replaced with a T and which subsequence includes the G to T substitution; (c) a sequence that is complementary to that of the sequence specified in (a); and (d) a sequence that is complementary to that of the subsequence specified in (b).

In yet another embodiment, the present invention may be summarized as an oligonucleotide sequence, and homologs thereof, which has a sequence selected from the following group: (a) the sequence of SEQ ID NO: 1, which SEQ ID NO: 1 has a BseR1 restriction enzyme site in intron 6, where a polymorphism in intron 6 results in deletion of the BseR1 restriction enzyme site; (b) a subsequence of SEQ ID NO: 1 including a BseR1 restriction enzyme site in intron 6, where the subsequence may be from 8 to 9824 nucleotides long and includes a polymorphism in intron 6 that results in deletion of the BseR1 restriction enzyme site; (c) a sequence that is complementary to that of the sequence specified in (a); and (d) a sequence that is complementary to that of the subsequence specified in (b).

A further embodiment of the present invention may be summarized as an oligonucleotide sequence, and homologs thereof, which has a sequence selected from the group consisting of (a) the sequence of SEQ ID NO: 1 except that approximately 75 nucleotides are deleted from the region of SEQ ID NO: 1 corresponding to exon 5; (b) a subsequence of SEQ ID NO: 1, where the subsequence is between 8 and 9750 nucleotides long and spans the portion of SEQ ID NO: 1 that correlates to exon 5 of the NURR1 gene except that a splicing variant wherein approximately 75 nucleotides are deleted from the exon 5 portion of the subsequence is present; (c) a sequence that is complementary to that of the sequence specified in (a); and (d) a sequence that is complementary to that of the subsequence specified in (b).

The nucleotides of the various sequence embodiments of the present invention may include DNA, RNA or mRNA. Further, the present invention contemplates amino acid sequences derived from the various nucleotide sequence embodiments of the present invention.

The present invention also contemplates methods of preventing, delaying the onset of, or treating Parkinson's Disease or dopaminergic dysfunction-related disorders in an individual expressing a mutant NURR1 gene. The contemplated methods include: (a) administering normal Nurr1 protein to the individual; (b) inhibiting the transcription, translation, or other expression of the mutant NURR1 gene in the individual; (c) inhibiting the biological action of the mutant Nurr1 protein in the individual; or (d) administering to the individual any molecule that activates the NURR1 gene or that alters the expression of the NURR1 gene; or (e) a combination of (a)–(d).

In one embodiment of the present invention, there is a method of diagnosing Parkinson's disease in an individual, comprising the steps of obtaining a sample from said individual, wherein said sample comprises nucleic acid; and assaying said sample for a NURR1 polynucleotide, wherein said NURR1 polynucleotide has an alteration. In a specific embodiment, NURR1 polynucleotide comprises a sequence selected from the group consisting of SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, and SEQ ID NO:94. In another specific embodiment, the assaying step comprises amplification with at least one primer selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:37, SEQ ID NO:38, SEQ ID NO:39, SEQ ID NO:40, SEQ ID NO:41, SEQ ID NO:42, SEQ ID NO:88, SEQ ID NO:89, SEQ ID NO:90, SEQ ID NO:91, SEQ ID NO:92, SEQ ID NO:93, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, and SEQ ID NO:123.

In an additional specific embodiment, the alteration is a mutation in said NURR1 polynucleotide. In a further specific embodiment, the mutation is in a regulatory region of said NURR1 polynucleotide. In another specific embodiment, the mutation is a deletion in said NURR1 polynucleotide. In an additional specific embodiment, the mutation is a substitution in said NURR1 polynucleotide. In a further specific embodiment, the deletion is at position −291 in said NURR1 polynucleotide. In a specific embodiment, the substitution is at position −245 in said NURR1 polynucleotide. In another specific embodiment, the substitution is a T to G substitution at position −245 in said NURR1 polynucleotide. In an additional specific embodiment, the mutation comprises a deletion in exon 5. In another specific embodiment, the deletion is of approximately 75 nucleotides. In an additional specific embodiment, the deletion does not disrupt the reading frame of said NURR1 polynucleotide. In a further specific embodiment, the alteration is a polymorphism in said NURR1 polynucleotide. In an additional specific embodiment, the polymorphism is a homozygous 7048G7049 polymorphism. In a specific embodiment, a symptom of said Parkinson's disease is selected from the group consisting of rest tremor, cogwheel rigidity, bradykinesia, postural reflex impairment, good response to 1-dopa treatment, the absence of prominent oculomotor palsy, cerebellar or pyramidal signs, amyotrophy, dyspraxia, and dysphasia. In another specific embodiment, the individual further comprises a defect at chromosome 2q22–2q23.

In another embodiment of the present invention, there is a method of diagnosing Parkinson's disease in an individual comprising the steps of obtaining a sample from said individual; and assaying said sample for a decrease in NURR1 level, wherein said decrease indicates said individual has said Parkinson's disease. In a specific embodiment, the NURR1 level is a NURR1 mRNA level or a NURR1 polypeptide level. In a specific embodiment, the sample further comprises a decrease in tyrosine hydroxylase expression.

In another embodiment of the present invention, there is a method of identifying an individual at risk for Parkinson's disease comprising the steps of obtaining a sample from said individual; and assaying said sample for a decrease in NURR1 level, wherein said decrease indicates said individual is at risk for said Parkinson's disease. In a specific embodiment, the NURR1 level is a NURR1 mRNA level. In a further specific embodiment, the NURR1 level is a NURR1 polypeptide level. In an additional specific embodiment, the sample further comprises a decrease in tyrosine hydroxylase expression.

In an additional embodiment of the present invention, there is a method of detecting the presence or absence of a mutation associated with Parkinson's disease in an individual, comprising isolating a nucleic acid from said individual, said nucleic acid comprising a test NURR1 polynucleotide; comparing the test NURR1 polynucleotide to a reference NURR1 polynucleotide; and identifying a difference between the test NURR1 polynucleotide and the reference NURR1 polynucleotide, wherein a difference determines the presence or absence of the mutation. In a specific embodiment, the test NURR1 polynucleotide and the reference NURR1 polynucleotide have an identical nucleic acid sequence at and/or near position −245. In a further specific embodiment, the test NURR1 polynucleotide and the reference NURR1 polynucleotide have a different nucleic acid sequence at and/or near position −245. In another specific embodiment, the test NURR1 polynucleotide and the reference NURR1 polynucleotide have an identical nucleic acid sequence at and/or near position −291. In an additional specific embodiment, the test NURR1 polynucleotide and the reference NURR1 polynucleotide have a different nucleic acid sequence at and/or near position −291. In another specific embodiment, the difference is further defined as a −291T-del in the test NURR1 polynucleotide. In a further specific embodiment, the difference is further defined as a −245T-G-sub in the test NURR1 polynucleotide. In an additional specific embodiment, the comparing step is further defined as comprising SSCP analysis, DHPLC, sequencing, hybridization, or a combination thereof.

In an additional embodiment of the present invention, there is a method of identifying an upregulator of NURR1 polynucleotide expression, comprising the steps of providing a test compound to a transgenic animal, wherein said transgenic animal comprises a reporter nucleic acid sequence operably regulated by a NURR1 promoter; comparing the level of the reporter nucleic acid sequence expression in said animal in the absence and presence of the test compound, wherein an increase in said level following administration of said test compound indicates said test compound is an upregulator. In a specific embodiment, the method further comprises the step of administering the upregulator in a pharmaceutically acceptable composition to an individual having a dopaminergic dysfunction-related disorder. In a specific embodiment, the individual is further defined as having at least one symptom of Parkinson's disease.

In an additional embodiment of the present invention, there is a method of treating Parkinson's disease in an organism, comprising the step of administering to the organism a therapeutically effective amount of a NURR1 polypeptide. In a specific embodiment, the NURR1 polypeptide is administered to said organism by administering a NURR1 polynucleotide. In a specific embodiment, the NURR1 polynucleotide is administered in a vector. In an additional specific embodiment, the vector comprises a plasmid, a viral vector, a lipid, a liposome, a polypeptide, or a combination thereof. In another specific embodiment, the polynucleotide is administered with a physiologically acceptable carrier.

In another embodiment of the present invention, there is a kit for diagnosing Parkinson's disease in an animal comprising a primer for assaying a NURR1 polynucleotide. In a specific embodiment, the primer is selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:37, SEQ ID NO:38, SEQ ID NO:39, SEQ ID NO:40, SEQ ID NO:41, SEQ ID NO:42, SEQ ID NO:88, SEQ ID NO:89, SEQ ID NO:90, SEQ ID NO:91, SEQ ID NO:92, SEQ ID NO:93, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, and SEQ ID NO:123.

In an additional embodiment of the present invention, there is an isolated NURR1 polynucleotide comprising a −291T-del. In another embodiment of the present invention, there is an isolated NURR1 polynucleotide comprising a −245T-G-sub. In an additional embodiment of the present invention, there is an isolated NURR1 polynucleotide comprising a 7048G7049 polymorphism.

In one embodiment of the present invention, there is a transgenic animal comprising a mutant NURR1 polynucleotide, said animal exhibiting at least one symptom associated with Parkinson's disease. In a specific embodiment, the animal is a mouse or rat. In a specific embodiment, the symptom associated with Parkinson's disease comprises rest tremor, cogwheel rigidity, bradykinesia, postural reflex impairment, good response to 1-dopa treatment, the absence of prominent oculomotor palsy, cerebellar or pyramidal signs, amyotrophy, dyspraxia, or dysphasia. In an additional specific embodiment, the mutant NURR1 polynucleotide is further defined as comprising a −291T-del, a −245T-G sub, a homozygous 7048G7049 polymorphism, a mutation as in SEQ ID NO:36, or a combination thereof.

In another embodiment of the present invention, there is a method of treating Parkinson's Disease in an individual, wherein the individual expresses a mutant NURR1 polynucleotide, the method comprising a step selected from the group consisted of administering functional Nurr1 protein to the individual; inhibiting the transcription or translation of the mutant NURR1 polynucleotide in the individual; inhibiting the biological action of the mutant Nurr1 protein in the individual; administering to the individual any molecule that activates the NURR1 polynucleotide or that alters the expression of the NURR1 polynucleotide; or a combination thereof.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the features and advantages of the present invention, reference is now made to the detailed description of the invention along with the accompanying figures in which corresponding numerals in different figures refer to corresponding parts and in which:

In FIGS. 2A and 2B, there is shown direct sequencing analysis of PCR amplified exon 1 demonstrating a heterozygous −291-T-del and −245-T-G-sub as indicated by an arrow. In FIGS. 2C and 2D the subclone confirmed the −291T-del and the −245-T-G-sub mutations. W: Wild-type; M: Mutation. In FIG. 2E there is a diagram of the exon 1 sequence encoding the −291-T-del or −245-T-G-sub.

FIGS. 4B, 4C, 4D, and 4E represent four completed families with the identified −291-T-del mutation. Haplotypes of members in these four PD families were constructed based on the informative genotyping of microsatellites and SNPs, and the disease-associated haplotypes were defined in box.

FIG. 5A demonstrates real-time RT-PCR determination of NURR1 mRNA levels in HEK293 cells or SH-5YSY cells transfected with human NURR1: wild-type (lane 1), −291T-del (lane 2), −245T-G-sub (lane 3), wild-type plus −291T-del (lane 4), vector alone (lane 5), or without transfection (lane 6). FIG. 5B illustrates a transfection efficiency assay by measuring β-galactosidase mRNA levels in HEK239 cells co-transfected with human NURR1: wild-type (lane 1), −291T-del (lane 2); −245T-G-sub (lane 3); or β-galactosidase+vector (lane 4). FIG. 5C shows measurement of luciferase activity in the extracts of SH-5YSY cells co-transfected with the luciferase reporter plasmid and the human NURR1 gene: wild-type NURR1 gene (lane 1); −291T-del (lane 2); −245T-G-sub (lane 3); or vector alone (lane 4). FIG. 5D demonstrates TH mRNA levels in SH5YSY cells transfected with wild-type NURR1 gene (lane 1), −291T-del (lane 2), −245T-G-sub (lane 3), or vector alone (lane 4). FIG. 5E provides real-time RT-PCR measurement of mRNA levels of NURR1 (upper panel) vs. GAPDH (lower panel) in the lymphocytes of 5 members of a fPD family. FIG. 5F shows relative NURR1 mRNA levels were determined by the threshold cycle after normalization with GAPDH. Lane 1: the PD patient's two healthy sisters used as a normal controls; lane 2: the PD patient's father; lane 3: the patient's PD mother; and lane 4: the PD patient himself. Values in FIGS. 5A, 5C, and 5F represent the mean±SD of three experiments in triplicate. *p<0.01, p<0.005, and *p<0.001 vs wild-type (Student-t test).

FIG. 8 is a sequence comparison of the dominant form of NURR1 exon5–6 (top) and a splicing variant (bottom) of the present invention wherein 75 nucleotides are deleted from the dominant form.

DETAILED DESCRIPTION OF THE INVENTION

Figure 1:
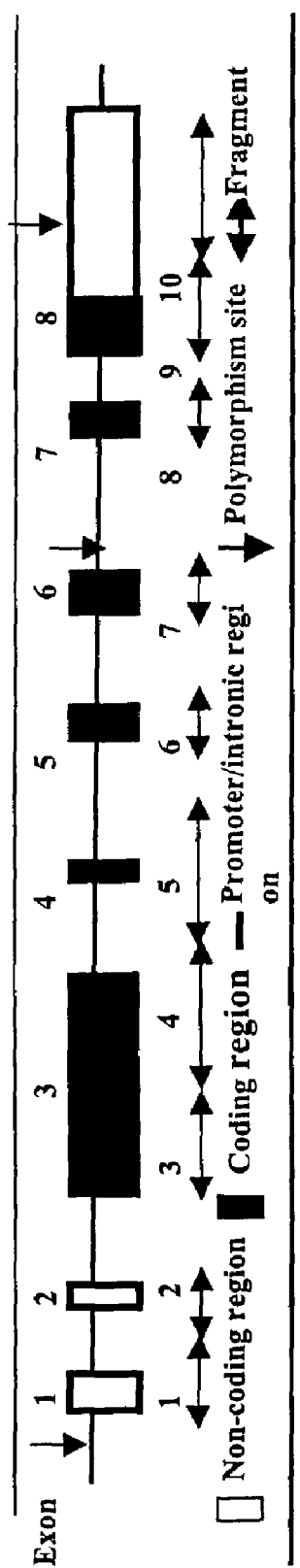
FIG. 1 is a diagram of the genomic structure of human NURR1 gene and a table of some relevant PCR primers in accordance with the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

I. Definitions

Terms defined herein have meanings as commonly understood by a person of ordinary skill in the areas relevant to the present invention. Terms such as "a", "an" and "the" are not intended to refer to only a single entity, but include a general class of which a specific example may be used for illustration. The terminology herein is used to describe specific embodiments of the invention, but their usage does not limit the invention, except as outlined in the claims.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end oligonucleotides referred to as the "5'end" if its 5' phosphate is not linked to the 3' oxygen of a mononucleotide pentose ring and as the "3'end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "a gene encoding," "nucleic acid molecule encoding," "DNA sequence encoding," and "DNA encoding" means a nucleic acid sequence comprising the coding region of a gene or in other words the nucleic acid sequence which encodes a gene product, such as a protein. In the case of DNA, for example, the terms refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper-initiation of transcription and/or correct processing of the primary RNA transcript. Alternatively, the coding region utilized in the expression vectors of the present invention may contain endogenous enhancers/promoters, splice junctions, intervening sequences, polyadenylation signals, or a combination of both endogenous and exogenous control elements.

As used herein, the term "amplifiable nucleic acid" is used in reference to nucleic acids that may be amplified by any amplification method. It is contemplated that "amplifiable nucleic acid" will usually comprise a "sample template."

"Amplification" is a special case of nucleic acid replication involving template specificity. It is to be contrasted with nonspecific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al, 1972). Other nucleic acid will not be replicated by this amplification enzyme. Similarly, in the case of T7 RNA polymerase, this amplification enzyme has a stringent specificity for its own promoters (Chamberlin et al., 1970). In the case of T4 DNA ligase, the enzyme will not ligate the two oligonucleotides where there is a mismatch between the oligonucleotide substrate and the template at the ligation junction (Wu and Wallace, 1989). Finally, Taq and Pfu polymerases by virtue of their ability to function at high temperature, are found to display high specificity for the sequences bounded and thus defined by the primers; the high temperature results in thermodynamic conditions that favor primer hybridization with the target sequences and not hybridization with non-target sequences (Erlich (ed.), PCR Technology, Stockton Press, 1989).

As used herein, the term "amplification reagents" refers to those reagents (deoxyribonucleotide triphosphates, buffer, etc.), needed for amplification except for primers. nucleic acid template and the amplification enzyme. Typically, amplification reagents along with other reaction components are placed and contained in a reaction vessel (test tube, microwell, etc.).

The term "antagonist" refers to molecules or compounds which inhibit the action of a composition (e.g., a protein). Antagonists may or may not be homologous to the targets of these compositions in respect to conformation, charge or other characteristics. In particularly preferred embodiments, antagonists prevent the functioning of proteins. It is contemplated that antagonists may prevent binding of a protein and its target(s). However, it is not intended that the term be limited to a particular site or function.

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter that permits the synthesis of a complementary strand. Once introduced into a cell, this transcribed strand combines with natural sequences produced by the cell to form duplexes. These duplexes then block either the further transcription or translation. In this manner mutant phenotypes may be generated. The designation "negative" is sometimes used in the art in reference to the antisense strand, and "positive" is sometimes used in reference to the sense strand.

The term "antisense" also is used in reference to RNA sequences that are complementary to a specific RNA sequence (e.g. mRNA). The term "antisense strand" is used in reference to a nucleic acid strand that is complementary to the "sense" strand. The designation (−) (i.e., "negative") is sometimes used in reference to the antisense strand with the designation sometimes used in reference to the sense (i.e., "positive") strand.

A gene may produce multiple RNA species which are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on CDNA I wherein CDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

The term "at position X, near position X, or both" as used herein, refers to nucleotides at a particular position X and/or flanking the position, such as at about 30–40 nucleotides on either side of position X, at about 20 nucleotides on either side of position X, at about 15 nucleotides on either side of position X, at about 10 nucleotides on either side of position X, at about 7 nucleotides on either side of position X, at about 5 nucleotides on either side of position X, or at about two or three nucleotides on either side of position X. A skilled artisan recognizes that alterations, such as mutations, near a particular position are capable of influencing the activity of the region, gene or gene product of interest.

The terms "complement," "complementary" or "complementarity" as used herein, refer to the natural binding of polynucleotides under permissive salt and temperature conditions by base-pairing. For example, for the sequence "A-G-T" binds to the complementary sequence "T-C-A". Complementarity between two single-stranded molecules may be partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "correlates with expression of a polynucleotide," as used herein, indicates that the detection of the presence of ribonucleic acid that is similar to a particular nucleotide sequence by Northern analysis is indicative of the presence of mRNA encoding a protein in a sample and thereby correlates with expression of the transcript from the polynucleotide encoding the protein.

A "deletion," as used herein, refers to a change in either amino acid or nucleotide sequence in which one or more amino acid or nucleotide residues, respectively, are absent.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "gene" means the deoxyribonucleotide sequences comprising the coding region of a structural gene and the including sequences located adjacent to the coding region on both the 5' and 3', ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences, these sequences. The term "gene" encompasses both cDNA and genomic forms of a gene. A genomic form or clone of a gene contains the coding region ("exons") interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional processing, and that determine stability of the mRNA.

The term "isolated" when used in relation to a nucleic acid, as in "an isolated oligonucleotide" refers to a nucleic acid sequence that is identified and separated from at least one containment nucleic acid with which it is ordinarily associated in its natural source. Isolated nucleic acid is such present in a form or setting that is different from that in which it is found in nature (e.g., in an expression vector). In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a mammalian protein includes, by way of example, such nucleic acid in cells ordinarily expressing, a protein where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "Parkinson's disease," as used herein refers to any medical condition wherein an individual experiences one or more of the following symptoms: rest tremor, cogwheel rigidity, bradykinesia, postural reflex impairment, good response to 1-dopa treatment, the absence of prominent oculomotor palsy, cerebellar or pyramidal signs, amyotrophy, dyspraxia, and/or dysphasia. In a specific embodiment, the present invention is utilized for the treatment of a dopaminergic dysfunction-related disorder. In a specific embodiment, the individual with Parkinson's disease comprises DNA comprising a NURR1 defect, such as a particular mutation. Specific mutations include −291T-del, −245T-G sub, a homozygous 7048G7049 polymorphism, a mutation as in SEQ ID NO:36, or a combination thereof. In other specific embodiments, the individual also comprises a defect at chromosome 2q22–2q23 and/or a decrease in tyrosine hydroxylase expression.

As used herein, the term "poly-A RNA" refers to RNA molecules having a stretch of adenine nucleotides at the 3' end. This polyadenine stretch is also referred to as a "poly-A tail". Eukaryotic mRNA molecules contain poly-A tails and are referred to as poly-A RNA.

As used herein, the term "polymerase chain reaction" ("PCR") refers to the method of K. B. Mullis U.S. Pat. Nos. 4,683,195, 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence.

To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle", there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction". Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection, incorporation $^{32}$P-labeled deoxynucleotide triphosphates, such as dCTP or dATP, into the amplified segment). In addition to genomic DNA, any oligonucleotide sequence can be amplified with the appropriate set of primer molecules. In particular the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence," as used herein, denotes a DNA sequence that directs both the termination and polyadenylation of the nascent RNA transcript. Efficient polyadenylation of the recombinant transcript is desirable, as transcripts lacking a poly A tail are unstable and are rapidly degraded. The poly A signal utilized in an expression vector may be "heterologous" or "endogenous." An endogenous poly A signal is one that is found at the 3' end of the coding region of a given gene in the genome. A heterologous poly A signal is one which is isolated from one gene and placed 3' to another gene. A commonly used heterologous poly A signal is the SV40 poly A signal. The SV40 poly A signal is contained on a 237 bp BamHI/Bcl restriction fragment, and directs both termination and polyadenylation (Sambrook et al., 1989).

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification but may alternatively be double stranded. If double stranded, the primer is first treated to separate its strands before being used to prepare extension products. Often, the primer is an oligodeoxyribonucleotide.

The primer must be sufficiently long to prime the synthesis of extension products in the presence of the inducing agent. The exact lengths of the primers will depend on many factors, including temperature, source of primer and the method used.

As used herein, the term "promoter/enhancer" denotes a segment of DNA which contains sequences capable of providing both promoter and enhancer functions (i.e., the functions provided by a promoter element and an enhancer element, as discussed above). For example, the long terminal repeats of retroviruses contain both promoter and enhancer functions. The enhancer/promoter may be "endogenous," "exogenous," or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques), such that transcription of that gene is directed by the linked enhancer/promoter. Transcriptional control signals in eukaryotes comprise "promoter" and "enhancer" elements. Promoters and enhancers consist of short arrays of DNA sequences that interact specifically with cellular proteins involved in transcription (Maniatis et al., 1987). Promoter and enhancer elements have been isolated from a variety of eukaryotic sources including genes in yeast, insect and mammaliann cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review, see Voss et al, 1986; and Maniatis et al, supra). For example, the SV40 early gene enhancer is very active in a wide variety of cell types from many mammalian species, and has been widely used for the expression of proteins in mammalian cells (Dijkema et al, 1985). Two other examples of promoter/enhancer elements active in a broad range of mammalian cell types are those from the human elongation factor Iα gene (Uetsuki et al, 1989; Kim et al., 1990; Mizushima et al., 1990), and the long terminal repeats of the Rous sarcoma virus (Gorman et al., 1982), and the human cytomegalovirus (Boshart et al., 1985).

As used herein the terms "protein" and "peptide" refer to any compound comprising amino acids joined via peptide bonds including a peptide or polypeptide.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc.

As used herein the term "regulatory factors" refers to any factors (e.g., proteins, enzymes, peptides, small molecules, and nucleic acids) involved in the regulation of signaling pathways. For example, such factors include, but are not limited to, proteins, IKBS, IKKS, and agonists, antagonists, and cofactors that interact with these factors. It is contemplated that the regulatory factors can either directly or indirectly (e.g., through other factors) bind to a target of interest.

The term "sample," as used herein, is used in its broadest sense. The term encompasses biological sample(s) suspected of containing nucleic acid encoding a protein or fragments thereof and may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The presence of "splicing signals" on an expression vector often results in higher levels of expression of the recombinant transcript. Splicing signals mediate the removal of introns from the primary RNA transcript and consist of a splice donor and acceptor site (See e.g., Sambrook et al. 1989). A commonly used splice donor and acceptor site is the splice junction from the 16S RNA of SV40.

A "substitution," or "sub", as used herein, refers to the replacement of one or nucleotides by different amino acids or nucleotides, respectively.

As used herein, the term "target" when used in reference to the polymerase chain reaction, refers to the region of nucleic acid bounded by the primers used for polymerase chain reaction, the "target" is sought to be sorted oat from other nucleic acid sequences. A "segment" is defined as a region of nucleic acid within the target sequence.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microillection, liposome fusion, lipofection, protoplast fusion, retroviral infection, and biolistics. Thus, the term "stable transfection" or "stably transfected" refers to the introduction and integration of foreign DNA into the genome of the transfected cell. The term "stable transfectant" refers to a cell which has stably integrated foreign DNA into the genomic DNA. The term also encompasses cells that transiently express the inserted DNA or RNA for limited periods of time. Thus, the term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "treatment" as used herein refers to the prevention, improvement, amelioration, or removal of at least one symptom of a disease and, in a preferred embodiment, is Parkinson' disease or any disease related to deficient dopaminergic neurons. A skilled artisan recognizes that the treatment may result As used herein, the term "vector" is used in reference to nucleic acid molecules that transfer DNA segment(s) from one cell to another. The term "vehicle" is sometimes used interchangeably with "vector."

II. The Present Invention

NURR1, a member of nuclear receptor superfamily, essential for phenotype of the nigral dopaminergic neurons (Zetterstrom et al., 1997; Saucedo-Cardenas et al., 1998; Caastillo et al., 1998), is considered relevant to Parkinson's disease. To determine whether NURR1 is a susceptibility gene for PD, genetic analysis of NURR1 gene was performed in 201 PD patients and 221 age-matched normal controls (NC). Two PD-related mutations (−291T deletion and −245 T to G substitution) were identified in the first exon of NURR1 gene. These mutations affect one of the NURR1 alleles in 9.3% (10/107) of familial PD but not in sporadic PD (n=94) or in NC (n=221). Genotype-phenotype analysis in the ten families of these PD patients with the identified mutations clearly showed a segregation between PD and non-PD. Haplotype analysis in four complete fPD pedigrees suggested that at least two distinct founders may exist in fPD patients. The age at onset of disease and clinical features of these patients were not different from typical PD. The mutations resulted in a dramatically decreased NURR1 mRNA in vitro and in vivo and affected the tyrosine hydroxylase expression. In addition, NURR1 mRNA levels from lymphocytes of PD patients with the −291T-del showed a significant reduction. Together these data indicate that mutations in the exon 1 of NURR1 can cause dopaminergic dysfunction, which in specific embodiments leads to the phenotype of PD.

A skilled artisan recognizes that NURR1 sequences may be obtained from publicaly available databases, including the National Center for Biotechnology Information's GenBank database, or from the database of Celera Genomics, Inc. (Rockville, Md.). Examples of nucleic acid NURR1 sequences, followed by the Genbank accession number, include SEQ ID NO:43 (AB017586), SEQ ID NO:44 (AJ278700), SEQ ID NO:45 (NM_013613), SEQ ID NO:46 (NM_006186), SEQ ID NO:47 (BB539587), SEQ ID NO:48 (BB536225), SEQ ID NO:49 (BB432168), SEQ ID NO:50 (BB424269), SEQ ID NO:51 (BB345745), SEQ ID NO:52 (BB322941), SEQ ID NO:53 (BB023391), SEQ ID NO:54 (BB023355), SEQ ID NO:55 (AB019433), SEQ ID NO:56 (XM_002441), SEQ ID NO:57 (AV356519), SEQ ID NO:58 (AV356512), SEQ ID NO:59 (AV382234), SEQ ID NO:60 (AV368035), SEQ ID NO:61 (AV352127), SEQ ID NO:62 (AV341553), SEQ ID NO:63 (AV245724), SEQ ID NO:64 (AV221665), SEQ ID NO:65 (AB014889), SEQ ID NO:66 (U72345), SEQ ID NO:67 (U86783), SEQ ID NO:68 (U67738), SEQ ID NO:69 (U93471), SEQ ID NO:70 (U93429), SEQ ID NO:71 (S53744), SEQ ID NO:72 (R35928), and SEQ ID NO:73 (R25908). Examples of amino acid NURR1 sequence include SEQ ID NO:74 (548390), SEQ ID NO:75 (XP_002441), SEQ ID NO:76 (CAC27783), SEQ ID NO:77 (A46225), SEQ ID NO:78 (NP_038641), SEQ ID NO:79 (NP_006177), SEQ ID NO:80 (BAA77328), SEQ ID NO:81 (BAA75666), SEQ ID NO:82 (Q07917), SEQ ID NO:83 (P43354), SEQ ID NO:84 (Q04913), SEQ ID NO:85 (AAB68748), SEQ ID NO:86 (AAB68706), and SEQ ID NO:87 (AAB25138). In specific embodiments of the present invention, a NURR1 nucleic acid sequence of SEQ ID NO:1 and/or a NURR1 amino acid sequence of SEQ ID NO:2 is utilized.

III. Nucleic Acid-Based Expression Systems

A. Vectors

In specific methods of the present invention, a vector is utilized to transport an exogenous nucleic acid sequence. A nucleic acid sequence is "exogenous," if it is foreign to the cell into which the vector is being introduced or if the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., yeast artificial chromosomes (YACS) or bacterial artificial chromosomes (BACs)). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The identity of tissue-specific promoters or elements, as well as assays to characterize their activity, is well known to those of skill in the art. Examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

5. Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the recombinant vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid of the present application encoding a gene product or a portion thereof. Further examples of selectable and screenable markers are well known to one of skill in the art.

B. Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryotic host cell for replication of many vectors. Bacterial cells used as host cells for vector replication and/or expression include *E. coli* K12, DH5a, JM109, and KC8 strains, as well as a number of commercially available bacterial hosts such as SURE® Competent Cells and SOLO-PACKä Gold Cells (STRATAGENE®, La Jolla). Alternatively, bacterial cells such as *E. coli* K12 or LE392 strains could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. No. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROLä Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

IV. Nucleic Acid Detection

In addition to their use in directing the expression of NURR1 proteins, polypeptides and/or peptides, the nucleic acid sequences disclosed herein have a variety of other uses. For example, they have utility as probes or primers for embodiments involving nucleic acid hybridization.

A. Hybridization

The use of a probe or primer of between 13 and 100 nucleotides, preferably between 17 and 100 nucleotides in length, or in some aspects of the invention up to 1–2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

B. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to at least one of SEQ ID NO:43 through SEQ ID NO:73 or to SEQ ID NO:94 are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids that contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in their entirety.

A reverse transcriptase PCR™ (RT-PCR) amplification procedure may be performed to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). Davey et al., European Application No. 329 822 disclose a nucleic acid amplification process involving cyclically synthesizing single-stranded RNA ("ssRNA"), ssDNA, and double-stranded DNA (dsDNA), which may be used in accordance with the present invention.

Miller et al., PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

C. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art. See Sambrook et al., 1989. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

D. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCRTM(see above), single-strand conformation polymorphism analysis ("SSCP"), denaturing high pressure liquid chromatography (DHPLC) and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

E. Kits

All the essential materials and/or reagents required for detecting a NURR1 nucleic acid sequence in a sample may be assembled together in a kit. This generally will comprise at least one probe or primer designed to hybridize specifically to individual nucleic acids of interest in the practice of the present invention, including any one of SEQ ID NOS:43 through SEQ ID NO:73, or SEQ ID NO:94. Examples of such primers include SEQ ID NOS:3 through SEQ ID NO:30, SEQ ID NOS:37 through SEQ ID NO:42, SEQ ID NOS:88 through SEQ ID NO:93, and/or SEQ ID NOS:95 through SEQ ID NO:123. Also included may be enzymes suitable for amplifying nucleic acids, including various polymerases (reverse transcriptase, Taq, etc.), deoxynucleotides and buffers to provide the necessary reaction mixture for amplification. Such kits may also include enzymes and other reagents suitable for detection of specific nucleic acids or amplification products. Such kits generally will comprise, in suitable means, distinct containers for each individual reagent or enzyme as well as for each probe or primer pair.

V. NURR1 Nucleic Acids

A. Nucleic Acids and Uses Thereof

Certain aspects of the present invention concern at least one NURR1 nucleic acid. In certain aspects, the at least one NURR1 nucleic acid comprises a wild-type or mutant NURR1 nucleic acid. In particular aspects, the NURR1 nucleic acid encodes for at least one transcribed nucleic acid. In particular aspects, the NURR1 nucleic acid encodes at least one NURR1 protein, polypeptide or peptide, or biologically functional equivalent thereof. In other aspects, the NURR1 nucleic acid comprises at least one nucleic acid segment of SEQ ID NO:43 through SEQ ID NO:73 or SEQ ID NO:94, or at least one biologically functional equivalent thereof.

The present invention also concerns the isolation or creation of at least one recombinant construct or at least one recombinant host cell through the application of recombinant nucleic acid technology known to those of skill in the art or as described herein. The recombinant construct or host cell may comprise at least one NURR1 nucleic acid, and may express at least one NURR1 protein, polypeptide or peptide, or at least one biologically functional equivalent thereof.

As used herein "wild-type" refers to the naturally occurring sequence of a nucleic acid at a genetic locus in the genome of an organism, and sequences transcribed or translated from such a nucleic acid. Thus, the term "wild-type" also may refer to the amino acid sequence encoded by the nucleic acid. As a genetic locus may have more than one sequence or alleles in a population of individuals, the term "wild-type" encompasses all such naturally occurring alleles. As used herein the term "polymorphic" means that variation exists (i.e. two or more alleles exist) at a genetic locus in the individuals of a population. As used herein "mutant" refers to a change in the sequence of a nucleic acid or its encoded protein, polypeptide or peptide that is the result of the hand of man.

A nucleic acid may be made by any technique known to one of ordinary skill in the art. Non-limiting examples of synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. Pat. No. 5,705,629, each incorporated herein by reference. A non-limiting example of enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells, such as recombinant DNA vector production in bacteria (see for example, Sambrook et al. 1989, incorporated herein by reference).

A nucleic acid may be purified on polyacrylamide gels, cesium chloride centrifugation gradients, or by any other means known to one of ordinary skill in the art (see for example, Sambrook et al. 1989, incorporated herein by reference).

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g. adenine "A," guanine "G," thymine "T" and cytosine "C") or RNA (e.g. A, G, uracil "U" and C). The term "nucleic acid" encompass the terms "oligonucleotide" and "polynucleotide." The term "oligonucleotide" refers to at least one molecule of between about 3 and about 100 nucleobases in length. The term "polynucleotide" refers to at least one molecule of at least about 40 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss", a double stranded nucleic acid by the prefix "ds", and a triple stranded nucleic acid by the prefix "ts."

Thus, the present invention also encompasses at least one nucleic acid that is complementary to a NURR1 nucleic acid. In particular embodiments, the invention encompasses at least one nucleic acid or nucleic acid segment complementary to the sequence set forth in at least one of SEQ ID NO:43 through SEQ ID NO:73 or SEQ ID NO:94. Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" also refers to nucleic acid(s) that are substantially complementary, as may be assessed by the same nucleotide comparison set forth above. The term "substantially complementary" refers to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 75%, about 80%, about 85%, about 90%, about 95%, to about 100%, and any range therein, of the nucleobase sequence is capable of base-pairing with at least one single or double stranded nucleic acid molecule during hybridization. In certain embodiments, the term "substantially complementary" refers to at least one nucleic acid that may hybridize to at least one nucleic acid strand or duplex in stringent conditions. In certain embodiments, a "partly complementary" nucleic acid comprises at least one sequence that may hybridize in low stringency conditions to at least one single or double stranded nucleic acid, or contains at least one sequence in which less than about 70% of the nucleobase sequence is capable of base-pairing with at least one single or double stranded nucleic acid molecule during hybridization.

As used herein, "hybridization", "hybridizes" or "capable of hybridizing" is understood to mean the forming of a double or triple stranded molecule or a molecule with partial double or triple stranded nature. The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating at least one nucleic acid, such as a gene or nucleic acid segment thereof, or detecting at least one specific mRNA transcript or nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence of formamide, tetramethylammonium chloride or other solvent(s) in the hybridization mixture. It is generally appreciated that conditions may be rendered more stringent, such as, for example, the addition of increasing amounts of formamide.

It is also understood that these ranges, compositions and conditions for hybridization are mentioned by way of non-limiting example only, and that the desired stringency for a particular hybridization reaction is often determined empirically by comparison to one or more positive or negative controls. Depending on the application envisioned it is preferred to employ varying conditions of hybridization to achieve varying degrees of selectivity of the nucleic acid(s) towards target sequence(s). In a non-limiting example, identification or isolation of related target nucleic acid(s) that do not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

One or more nucleic acid(s) may comprise, or be composed entirely of, at least one derivative or mimic of at least one nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refers to a molecule that may or may not structurally resemble a naturally occurring molecule, but functions similarly to the naturally occurring molecule. As used herein, a "moiety" generally refers to a smaller chemical or molecular component of a larger chemical or molecular structure, and is encompassed by the term "molecule."

As used herein a "nucleobase" refers to a naturally occurring heterocyclic base, such as A, T, G, C or U ("naturally occurring nucleobase(s)"), found in at least one naturally occurring nucleic acid (i.e. DNA and RNA), and their naturally or non-naturally occurring derivatives and mimics. Non-limiting examples of nucleobases include purines and pyrimidines, as well as derivatives and mimics thereof, which generally can form one or more hydrogen bonds ("anneal" or "hybridize") with at least one naturally occurring nucleobase in manner that may substitute for naturally occurring nucleobase pairing (e.g. the hydrogen bonding between A and T, G and C, and A and U).

Nucleobase, nucleoside and nucleotide mimics or derivatives are well known in the art, and have been described in exemplary references such as, for example, Scheit, Nucleotide Analogs (John Wiley, New York, 1980), incorporated herein by reference. "Purine" and "pyrimidine" nucleobases encompass naturally occurring purine and pyrimidine nucleobases and also derivatives and mimics thereof, including but not limited to, those purines and pyrimidines substituted by one or more of alkyl, carboxyalkyl, amino, hydroxyl, halogen (i.e. fluoro, chloro, bromo, or iodo), thiol, or alkylthiol wherein the alkyl group comprises of from about 1, about 2, about 3, about 4, about 5, to about 6 carbon atoms. Non-limiting examples of purines and pyrimidines include deazapurines, 2,6-diaminopurine, 5-fluorouracil, xanthine, hypoxanthine, 8-bromoguanine, 8-chloroguanine, bromothymine, 8-aminoguanine, 8-hydroxyguanine, 8-methylguanine, 8-thioguanine, azaguanines, 2-aminopurine, 5-ethylcytosine, 5-methylcyosine, 5-bromouracil, 5-ethyluracil, 5-iodouracil, 5-chlorouracil, 5-propyluracil, thiouracil, 2-methyladenine, methylthioadenine, N,N-diemethyladenine, azaadenines, 8-bromoadenine, 8-hydroxyadenine, 6-hydroxyaminopurine, 6-thiopurine, 4-(6-aminohexyl/cytosine), and the like. A table of exemplary, but not limiting, purine and pyrimidine derivatives and mimics is also provided herein below.

As used herein, "nucleoside" refers to an individual chemical unit comprising a nucleobase covalently attached to a nucleobase linker moiety. A non-limiting example of a "nucleobase linker moiety" is a sugar comprising 5-carbon atoms (a "5-carbon sugar"), including but not limited to deoxyribose, ribose or arabinose, and derivatives or mimics of 5-carbon sugars. Non-limiting examples of derivatives or mimics of 5-carbon sugars include 2'-fluoro-2'-deoxyribose or carbocyclic sugars where a carbon is substituted for the oxygen atom in the sugar ring. By way of non-limiting example, nucleosides comprising purine (i.e. A and G) or 7-deazapurine nucleobases typically covalently attach the 9 position of the purine or 7-deazapurine to the 1'-position of a 5-carbon sugar. In another non-limiting example, nucleosides comprising pyrimidine nucleobases (i.e. C, T or U) typically covalently attach the 1 position of the pyrimidine to 1'-position of a 5-carbon sugar (Kornberg and Baker, DNA Replication, 2nd Ed. (Freeman, San Francisco, 1992). However, other types of covalent attachments of a nucleobase to a nucleobase linker moiety are known in the art, and non-limiting examples are described herein.

As used herein, a "nucleotide" refers to a nucleoside further comprising a "backbone moiety" generally used for the covalent attachment of one or more nucleotides to another molecule or to each other to form one or more nucleic acids. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when the nucleotide comprises derivatives or mimics of a naturally occurring 5-carbon sugar or phosphorus moiety, and non-limiting examples are described herein.

A non-limiting example of a nucleic acid comprising such nucleoside or nucleotide derivatives and mimics is a "polyether nucleic acid", described in U.S. Pat. No. 5,908,845, incorporated herein by reference, wherein one or more nucleobases are linked to chiral carbon atoms in a polyether backbone. Another example of a nucleic acid comprising nucleoside or nucleotide derivatives or mimics is a "peptide nucleic acid", also known as a "PNA", "peptide-based nucleic acid mimics" or "PENAMs", described in U.S. Pat. Nos. 5,786,461, 5891,625, 5,773,571, 5,766,855, 5,736,336, 5,719,262, 5,714,331, 5,539,082, and WO 92/20702, each of which is incorporated herein by reference. A peptide nucleic acid generally comprises at least one nucleobase and at least one nucleobase linker moiety that is either not a 5-carbon sugar and/or at least one backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

Peptide nucleic acids generally have enhanced sequence specificity, binding properties, and resistance to enzymatic degradation in comparison to molecules such as DNA and RNA (Egholm et al., Nature 1993, 365, 566; PCT/EP/ 01219). In addition, U.S. Pat. Nos. 5,766,855, 5,719,262, 5,714,331 and 5,736,336 describe PNAs comprising naturally and non-naturally occurring nucleobases and alkylamine side chains with further improvements in sequence specificity, solubility and binding affinity. These properties promote double or triple helix formation between a target nucleic acid and the PNA.

U.S. Pat. No. 5,641,625 describes that the binding of a PNA to a target sequence has applications including the creation of PNA probes to nucleotide sequences, modulating (i.e. enhancing or reducing) gene expression by binding of a PNA to an expressed nucleotide sequence, and cleavage of specific dsDNA molecules. In certain embodiments, nucleic acid analogues such as one or more peptide nucleic acids may be used to inhibit nucleic acid amplification, such as in PCR, to reduce false positives and discriminate between single base mutants, as described in U.S. Pat. No. 5,891,625.

U.S. Pat. No. 5,786,461 describes PNAs with amino acid side chains attached to the PNA backbone to enhance solubility. The neutrality of the PNA backbone may contribute to the thermal stability of PNA/DNA and PNA/RNA duplexes by reducing charge repulsion. The melting temperature of PNA containing duplexes, or temperature at which the strands of the duplex release into single stranded molecules, has been described as less dependent upon salt concentration.

One method for increasing amount of cellular uptake property of PNAs is to attach a lipophilic group. U.S. application Ser. No. 117,363, filed Sep. 3, 1993, describes several alkylamino functionalities and their use in the attachment of such pendant groups to oligonucleotides. U.S. application Ser. No. 07/943,516, filed Sep. 11, 1992, and its corresponding published PCT application WO 94/06815, describe other novel amine-containing compounds and their incorporation into oligonucleotides for, inter alia, the purposes of enhancing cellular uptake, increasing lipophilicity, causing greater cellular retention and increasing the distribution of the compound within the cell.

Additional non-limiting examples of nucleosides, nucleotides or nucleic acids comprising 5-carbon sugar and/or backbone moiety derivatives or mimics are well known in the art.

In a certain aspect, the present invention concerns at least one nucleic acid that is an isolated nucleic acid. As used herein, the term "isolated nucleic acid" refers to at least one nucleic acid molecule that has been isolated free of, or is otherwise free of, the bulk of the total genomic and transcribed nucleic acids of one or more cells, particularly mammalian cells, and more particularly human and/or mouse and/or rat cells. In certain embodiments, "isolated nucleic acid" refers to a nucleic acid that has been isolated free of, or is otherwise free of, bulk of cellular components and macromolecules such as lipids, proteins, small biological molecules, and the like. As different species may have a RNA or a DNA containing genome, the term "isolated nucleic acid" encompasses both the terms "isolated DNA" and "isolated RNA". Thus, the isolated nucleic acid may comprise a RNA or DNA molecule isolated from, or otherwise free of, the bulk of total RNA, DNA or other nucleic acids of a particular species. As used herein, an isolated nucleic acid isolated from a particular species is referred to as a "species specific nucleic acid." When designating a nucleic acid isolated from a particular species, such as human, such a type of nucleic acid may be identified by the name of the species. For example, a nucleic acid isolated from one or more humans would be an "isolated human nucleic acid", a nucleic acid isolated from human would be an "isolated human nucleic acid", and so forth.

Of course, more than one copy of an isolated nucleic acid may be isolated from biological material, or produced in vitro, using standard techniques that are known to those of skill in the art. In particular embodiments, the isolated nucleic acid is capable of expressing a protein, polypeptide or peptide that has NURR1 activity. In other embodiments, the isolated nucleic acid comprises an isolated NURR1 gene.

In certain embodiments, a "gene" refers to a nucleic acid that is transcribed. As used herein, a "gene segment" is a nucleic acid segment of a gene. In certain aspects, the gene includes regulatory sequences involved in transcription, or message production or composition. In particular embodiments, the gene comprises transcribed sequences that encode for a protein, polypeptide or peptide. In other particular aspects, the gene comprises a NURR1 nucleic acid, and/or encodes a NURR1 polypeptide or peptide coding sequences. The term "an amino acid sequence" as used herein may be used interchangeably with the terms protein, polypeptide, or peptide, and the like. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, and so forth. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide and/or peptide encoding unit. As will be understood by those in the art, this function term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

"Isolated substantially away from other coding sequences" means that the gene of interest, in this case the NURR1 gene(s), forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by the hand of man.

In certain embodiments, the nucleic acid is a nucleic acid segment. As used herein, the term "nucleic acid segment", is a smaller fragment of a nucleic acid, such as for non-limiting example, one that encodes only part of the NURR1 peptide or polypeptide sequence. Thus, a "nucleic acid segment" may comprise any part of the NURR1 gene sequence(s), of from about 2 nucleotides to the full length of the NURR1 peptide or polypeptide encoding region. In certain embodiments, the "nucleic acid segment" encompasses the full length NURR1 gene(s) sequence. In particular embodiments, the nucleic acid comprises any part of at least one of SEQ ID NO:43 through SEQ ID NO:73 or SEQ ID NO:94 sequence(s), of from about 2 nucleotides to the full length of the sequence disclosed in at least one of SEQ ID NO:43 through SEQ ID NO:73 or SEQ ID NO:94.

Various nucleic acid segments may be designed based on a particular nucleic acid sequence, and may be of any length. In certain embodiments, the nucleic acid segment may be a probe or primer. As used herein, a "probe" is a relatively short nucleic acid sequence, such as an oligonucleotide, used to identify other nucleic acid sequences to which it hybridizes. As used herein, a "primer" is a relatively short nucleic acid sequence used as a starting molecule for polymerization to extend from, such as in polymerase chain reaction, which is a method well known in the art. A non-limiting example of this would be the creation of nucleic acid segments of various lengths and sequence composition for probes and primers based on the sequences disclosed in at least one of SEQ ID NO:43 through SEQ ID NO:73 or SEQ ID NO:94.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The overall length may vary considerably between nucleic acid constructs. Thus, a nucleic acid segment of almost any length may be employed, with the total length preferably being limited by the ease of preparation or use in the intended recombinant nucleic acid protocol.

In a non-limiting example, one or more nucleic acid constructs may be prepared that include a contiguous stretch of nucleotides identical to or complementary to at least one of SEQ ID NO:43 through SEQ ID NO:73 or SEQ ID NO:94. A nucleic acid construct may be about 3, about 5, about 8, about 10 to about 14, or about 15, about 20, about 30, about 40 about 50, about 100, about 200, about 500, about 1,000, about 2,000, about 3,000, about 5,000, about 10,000, about 15,000, about 20,000, about 30,000, about 50,000, about 100,000, about 250,000, about 500,000, about 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges", as used herein, means any length or range including or between the quoted values (i.e. all integers including and between such values).

In particular embodiments, the invention concerns one or more recombinant vector(s) comprising nucleic acid sequences that encode a NURR1 protein, polypeptide or peptide that includes within its amino acid sequence a contiguous amino acid sequence in accordance with, or essentially as set forth in one of SEQ ID NO:74 through SEQ ID NO:87, particularly one corresponding to human Nurr1. In other embodiments, the invention concerns recombinant vector(s) comprising nucleic acid sequences that encode a mouse NURR1 protein, polypeptide or peptide that includes within its amino acid sequence a contiguous amino acid sequence. In particular aspects, the recombinant vectors are DNA vectors.

For example, the term "a sequence essentially as set forth in SEQ ID NO:74 means that the sequence substantially corresponds to a portion of SEQ ID NO:74 and has relatively few amino acids that are not identical to, or a biologically functional equivalent of, the amino acids of SEQ ID NO:74.

The term "biologically functional equivalent" is well understood in the art and is further defined in detail herein. Accordingly, a sequence that has between about 70% and about 80%; or more preferably, between about 81% and about 90%; or even more preferably, between about 91% and about 99%; of amino acids that are identical or functionally equivalent to the amino acids of at least one of SEQ ID NO:74 through SEQ ID NO:87 will be a sequence that is "essentially as set forth in at least one of SEQ ID NO:74 through SEQ ID NO:87", provided the biological activity of the protein, polypeptide or peptide is maintained.

In certain other embodiments, the invention concerns at least one recombinant vector that includes within its sequence a nucleic acid sequence essentially as set forth in at least one of SEQ ID NO:43 through SEQ ID NO:73 or SEQ ID NO:94. In particular embodiments, the recombinant vector comprises DNA sequences that encode protein(s), polypeptide(s) or peptide(s) exhibiting NURR1 activity.

The term "functionally equivalent codon" is used herein to refer to codons that encode the same amino acid, such as the six codons for arginine and serine, and also refers to codons that encode biologically equivalent amino acids. Information on codon usage in a variety of non-human organisms is known in the art (see for example, Bennetzen and Hall, 1982; Ikemura, 1981a, 1981b, 1982; Grantham et al., 1980, 1981; Wada et al., 1990; each of these references are incorporated herein by reference in their entirety). Thus, it is contemplated that codon usage may be optimized for other animals, as well as other organisms such as fungi, plants, prokaryotes, virus and the like, as well as organelles that contain nucleic acids, such as mitochondria, chloroplasts and the like, based on the preferred codon usage as would be known to those of ordinary skill in the art.

It will also be understood that amino acid sequences or nucleic acid sequences may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

Excepting intronic and flanking regions, and allowing for the degeneracy of the genetic code, nucleic acid sequences that have between about 70% and about 79%; or more preferably, between about 80% and about 89%; or even more particularly, between about 90% and about 99%; of nucleotides that are identical to the nucleotides of at least one of SEQ ID NO:43 through SEQ ID NO:73 or SEQ ID NO:94 will be nucleic acid sequences that are "essentially as set forth in at least one of SEQ ID NO:43 through SEQ ID NO:73 or SEQ ID NO:94".

It will also be understood that this invention is not limited to the particular nucleic acid or amino acid sequences of NURR1 Recombinant vectors and isolated nucleic acid segments may therefore variously include these coding regions themselves, coding regions bearing selected alterations or modifications in the basic coding region, and they may encode larger polypeptides or peptides that nevertheless include such coding regions or may encode biologically functional equivalent proteins, polypeptide or peptides that have variant amino acids sequences.

The nucleic acids of the present invention encompass biologically functional equivalent NURR1 proteins, polypeptides, or peptides. Such sequences may arise as a consequence of codon redundancy or functional equivalency that are known to occur naturally within nucleic acid sequences or the proteins, polypeptides or peptides thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Changes designed by man may be introduced, for example, through the application of site-directed mutagenesis techniques as discussed herein below, e.g., to introduce improvements or alterations to the antigenicity of the protein, polypeptide or peptide, or to test mutants in order to examine NURR1 protein, polypeptide or peptide activity at the molecular level.

Fusion proteins, polypeptides or peptides may be prepared, e.g., where the NURR1 coding regions are aligned within the same expression unit with other proteins, polypeptides or peptides having desired functions. Non-limiting examples of such desired functions of expression sequences include purification or immunodetection purposes for the added expression sequences, e.g., proteinaceous compositions that may be purified by affinity chromatography or the enzyme labeling of coding regions, respectively.

As used herein the term "sequence" encompasses both the terms "nucleic acid" and "proteinaceous" or "proteinaceous composition." As used herein, the term "proteinaceous composition" encompasses the terms "protein", "polypeptide" and "peptide." As used herein "artificial sequence" refers to a sequence of a nucleic acid not derived from sequence naturally occurring at a genetic locus, as well as the sequence of any proteins, polypeptides or peptides encoded by such a nucleic acid. A "synthetic sequence", refers to a nucleic acid or proteinaceous composition produced by chemical synthesis in vitro, rather than enzymatic production in vitro (i.e. an "enzymatically produced" sequence) or biological production in vivo (i.e. a "biologically produced" sequence).

VI. Pharmaceutical Compositions

Aqueous compositions of the present invention comprise an effective amount of a chemical compound or pharmaceutically acceptable salts thereof or the NURR1 protein, polypeptide, peptide, epitopic core region, inhibitor, and/or such like, and a NURR1 agonist or antagonist dissolved and/or dispersed in a pharmaceutically acceptable carrier and/or aqueous medium. Aqueous compositions of gene therapy vectors expressing any of the foregoing are also contemplated.

The phrases "pharmaceutically and/or pharmacologically acceptable" refer to molecular entities and/or compositions that do not produce an adverse, allergic and/or other untoward reaction when administered to an animal, such as a human, as appropriate.

As used herein, "pharmaceutically acceptable carrier" includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For human administration, preparations should meet sterility, pyrogenicity, general safety and/or purity standards as required by FDA Office of Biologics standards.

The biological material should be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, sub-cutaneous, intralesional, and/or even intraperitoneal routes. The preparation of an aqueous compositions that contain an effective amount of chemical compound or pharmaceutically acceptable salts thereof or a NURR1 agent as an active component and/or ingredient will be known to those of skill in the art in light of the present disclosure. Typically, such compositions can be prepared as injectables, either as liquid solutions and/or suspensions; solid forms suitable for using to prepare solutions and/or suspensions upon the addition of a liquid prior to injection can also be prepared; and/or the preparations can also be emulsified.

The pharmaceutical forms suitable for injectable use include sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microorganisms, such as bacteria and/or fungi.

Solutions of the active compounds as free base and/or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and/or use, these preparations contain a preservative to prevent the growth of microorganisms.

A chemical compound or NURR1 protein, polypeptide, peptide, agonist and/or antagonist of the present invention can be formulated into a composition in a neutral and/or salt form. Pharmaceutically acceptable salts, include the acid addition salts (formed with the free amino groups of the protein) and/or which are formed with inorganic acids such as, for example, hydrochloric and/or phosphoric acids, and/or such organic acids as acetic, oxalic, tartaric, mandelic, and/or the like. Salts formed with the free carboxyl groups can also be derived from inorganic bases such as, for example, sodium, potassium, ammonium, calcium, and/or ferric hydroxides, and/or such organic bases as isopropylamine, trimethylamine, histidine, procaine and/or the like. In terms of using peptide therapeutics as active ingredients, the technology of U.S. Pat. Nos. 4,608,251; 4,601,903; 4,599,231; 4,599,230; 4,596,792; and/or 4,578,770, each incorporated herein by reference, may be used.

The carrier can also be a solvent and/or dispersion medium containing, for example, water, ethanol, polyol (for example, glycerol, propylene glycol, and/or liquid polyethylene glycol, and/or the like), suitable mixtures thereof, and/or vegetable oils. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof. The preparation of more, and/or highly, concentrated solutions for direct injection is also contemplated, where the use of DMSO as solvent is envisioned to result in extremely rapid penetration, delivering high concentrations of the active agents to the desired area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like can also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media which can be employed will be known to those of skill in the are in light of the present disclosure. For example, one dosage could be dissolved in 1 ml of isotonic NaCl solution and/or either added to 1000 ml of hypodermoclysis fluid and/or injected at the proposed rate of infusion, (see for example, "Remington's Pharmaceutical Sciences" 15th Edition, pages 1035–1038 and/or 1570–1580). Some variation in dosage will necessarily occur depending on the condition of the subject being treated. The person responsible for administration will, in any event, determine the appropriate dose for the individual subject.

The chemical compound or pharmaceutically acceptable salts thereof or the active NURR1 protein-derived peptides and/or agents may be formulated within a therapeutic mixture to comprise about 0.0001 to 1.0 milligrams, and/or about 0.001 to 0.1 milligrams, and/or about 0.1 to 1.0 and/or even about 10milligrams per dose and/or so on. Multiple doses can also be administered.

In addition to the compounds formulated for parenteral administration, such as intravenous and/or intramuscular injection, other pharmaceutically acceptable forms include, e.g., tablets and/or other solids for oral administration; liposomal formulations; time release capsules; and/or any other form currently used, including cremes.

One may also use nasal solutions and/or sprays, aerosols and/or inhalants in the present invention. Nasal solutions are usually aqueous solutions designed to be administered to the nasal passages in drops and/or sprays. Nasal solutions are prepared so that they are similar in many respects to nasal secretions, so that normal ciliary action is maintained. Thus, the aqueous nasal solutions usually are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation.

Additional formulations which are suitable for other modes of administration include vaginal suppositories and/or pessaries. A rectal pessary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25–60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens as preservatives, a dye and/or flavoring, such as cherry and/or orange flavor.

A. Lipid Formulations and/or Nanocapsules

In certain embodiments, the use of lipid formulations and/or nanocapsules is contemplated for the introduction of a chemical compound or pharmaceutically acceptable salts thereof or NURR1 protein, polypeptides, peptides and/or agents, and/or gene therapy vectors, including both wild-type and/or antisense vectors, into host cells.

Nanocapsules can generally entrap compounds in a stable and/or reproducible way. To avoid side effects due to intracellular polymeric overloading, such ultrafine particles (sized around 0.1 mm) should be designed using polymers able to be degraded in vivo. Biodegradable polyalkyl-cyanoacrylate nanoparticles that meet these requirements are contemplated for use in the present invention, and/or such particles may be easily made.

In a preferred embodiment of the invention, the pharmaceutical may be associated with a lipid. The pharmaceutical associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/pharmaceutical-associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes.

Phospholipids may be used for preparing the liposomes according to the present invention and may carry a net positive, negative, or neutral charge. Diacetyl phosphate can be employed to confer a negative charge on the liposomes, and stearylamine can be used to confer a positive charge on the liposomes. The liposomes can be made of one or more phospholipids.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Lipids suitable for use according to the present invention can be obtained from commercial sources. For example, dimyristyl phosphatidylcholine ("DMPC") can be obtained from Sigma Chemical Co., diacetyl phosphate ("DCP") is obtained from K & K Laboratories (Plainview, N.Y.); cholesterol ("Chol") is obtained from Calbiochem☐Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Phospholipids can form a variety of structures other than liposomes when dispersed in water, depending on the molar ratio of lipid to water. At low ratios the liposome is the preferred structure. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs.

Liposomes interact with cells via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Liposome-mediated oligonucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the lipid may be associated with a hemagglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer and expression of an oligonucleotide in vitro and in vivo, then they are applicable for the present invention. Where a bacterial promoter is employed in the DNA construct, it also will be desirable to include within the liposome an appropriate bacterial polymerase.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in DRUG CARRIERS IN BIOLOGY AND MEDICINE, G. Gregoriadis ed. (1979) pp. 287–341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000 g and the liposomal pellets washed. The washed liposomes are resuspended at an appropriate total phospholipid concentration, e.g., about 50–200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

A pharmaceutical composition comprising the liposomes will usually include a sterile, pharmaceutically acceptable carrier or diluent, such as water or saline solution.

B. Kits

Therapeutic kits of the present invention are kits comprising a chemical compound or pharmaceutically acceptable salts thereof or a NURR1 protein, polypeptide, peptide, inhibitor, gene, vector and/or other NURR1 effector. Such kits will generally contain, in suitable container means, a pharmaceutically acceptable formulation of a chemical compound or pharmaceutically acceptable salts thereof or a NURR1 protein, polypeptide, peptide, domain, inhibitor, and/or a gene and/or vector expressing any of the foregoing in a pharmaceutically acceptable formulation. The kit may have a single container means, and/or it may have distinct container means for each compound.

When the components of the kit are provided in one and/or more liquid solutions, the liquid solution is an aqueous solution, with a sterile aqueous solution being particularly preferred. The chemical compound or pharmaceutically acceptable salts thereof or NURR1 compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the chemical compound or pharmaceutically acceptable salts thereof or NURR1 protein, gene and/or inhibitory formulation are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate chemical compound or pharmaceutically acceptable salts thereof or a NURR1 protein and/or gene composition within the body of an animal. Such an instrument may be a syringe, pipette, forceps, and/or any such medically approved delivery vehicle.

VII. Methods of Making Transgenic Mice

A particular embodiment of the present invention provides transgenic animals that contain the transgenic constructs of interest. In a specific embodiment, there is a transgenic non-human animal whose genome comprises a transgene encoding a NURR1 amino acid sequence, wherein said transgene is under the control of an operably linked promoter active in eukaryotic cells. In another specific embodiment the promoter is constitutive, tissue-specific, and/or inducible. In an additional specific embodiment, the animal is a mouse. In a preferred embodiment, a transgenic mouse is generated wherein the mouse harbors a NURR1 mutation, such as the −291T-del or the −245T-G-sub mutations. In specific embodiments, the transgenic mouse is then utilized to screen for drug candidates for a disease related to defective NURR1, such as Parkinson's disease.

In a general aspect, a transgenic animal is produced by the integration of a given transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, with standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 mg/ml in 5 mM Tris, pH 7.4 and 0.1 mM EDTA.

Other methods for purification of DNA for microinjection are described in Hogan et al. Manipulating the Mouse Embryo (Cold Spring Harbor Laboratory, Cold Spring Harbor, N.Y., 1986), in Palmiter et al. Nature 300:611 (1982); in The Qiagenologist, Application Protocols, 3rd edition, published by Qiagen, Inc., Chatsworth, Calif.; and in Sambrook et al. Molecular Cloning: A Laboratory Manual (Cold Spring Harbor Laboratory, Cold Spring Harbor, N.Y., 1989).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

VIII. Gene Therapy Administration

Where appropriate, gene therapy vectors can be formulated into preparations in solid, semisolid, liquid, or gaseous forms in the ways known in the art for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds.

Accordingly, the pharmaceutical composition of the present invention may be delivered via various routes and to various sites in an animal body to achieve a particular effect (see, e.g., Rosenfeld et al., 1991; Rosenfeld et al., 1991a; Jaffe et al., 1992). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, and topical administration.

One skilled in the art recognizes that different methods of delivery may be utilized to administer a vector into a cell. Examples include: (1) methods utilizing physical means, such as electroporation (electricity), a gene gun (physical force), or applying large volumes of a liquid (pressure); and (2) methods wherein said vector is complexed to another entity, such as a liposome or transporter molecule.

Accordingly, the present invention provides a method of transferring a therapeutic gene to a host, which comprises administering the vector of the present invention, preferably as part of a composition, with any of the aforementioned routes of administration or alternative routes known to those skilled in the art and appropriate for a particular application. Effective gene transfer of a vector to a host cell in accordance with the present invention can be monitored in terms of a therapeutic effect (e.g., alleviation of some symptom or sign associated with the particular disease being treated) or, further, by evidence of the transferred gene or expression of the gene within the host (e.g., with the polymerase chain reaction in conjunction with sequencing, Northern or Southern hybridizations, or transcription assays to detect the nucleic acid in host cells, or with immunoblot analysis, antibody-mediated detection, mRNA, or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be approximated further through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

The following examples are offered by way of example, and are not intended to limit the scope of the invention in any manner.

EXAMPLE 1

Materials and Methods

Study population. The study population consisted of 107 fPD, 94 sPD and 221 normal control subjects (NC). Subjects participated following informed consent. Race: Most of the fPD (96/107), sPD (87/94) and NC (194/221) were Caucasians, and the rest of them were African-American (7/107 fPD, 5/94 sPD, and 16/221 NC) or Hispanic (4/107 fPD, 2/94 sPD, and 11 NC). Age: the age at the disease onset was 29–75 yrs (55±22 yrs) for fPD and 42–78 yrs (62±11 yrs) for sPD; the age for NC was 28–79 yrs (58±11 yrs). Gender: There were 62 men and 45 women in fPD group; 54 men and 40 women in sPD group; and 128 men and 93 women in NC group. There was no difference in age and gender between PD and normal controls as assessed by analysis of variance (ANOVA). Family history: All fPD patients had a family history of PD in the first-degree relatives. Of 107 fPD 70 patients were from families with a history of PD for at least two generations. Diagnosis: All patients with PD were examined at the Parkinson's Disease Center, Baylor College of Medicine, and the diagnosis of PD was based on generally accepted criteria: the presence of two or more of the following signs and symptoms (rest tremor, cogwheel rigidity, bradykinesia and postural reflex impairment), good response to 1-dopa treatment, and the absence of prominent oculomotor palsy, cerebellar or pyramidal signs, amyotrophy, dyspraxia, dysphasia or other a typical features. The age at onset of PD was defined as appearance of the first symptom based on a detailed medical interview. Haplotype analysis: Haplotype analysis was performed in four available pedigrees of fPD with −291-T-del mutation using single PCR-restriction fragment length polymorphism (RFLP) or HDX analysis to detect single-nucleotide polymorphism (SNP) or repeats. DNA was amplified by PCR using sense and antisense primers specific for those SNP and microsatellite markers (D2S2922, D2S7048, D2S1353, D2S142, and D2S8336, Table 1a and 1b).

TABLE 1a

Primers and conditions used for PCR amplification

| Exon | Sense primer (5'–3') | Antisense primer (5'–3') | Annealing (° C.) | Product Size (bp) |
|---|---|---|---|---|
| 1 | CGCAAGCCACATAAACAAGG (SEQ ID NO: 88) | ACTGCATGGGCTGCATCTACT (SEQ ID NO: 95) | 59 | 269 |
| 2 | AGCTTCCTGTGTCTGTATTTCA (SEQ ID NO: 96) | CCTACCTTCAGCCGAGTTACAG (SEQ ID NO: 97) | 60 | 152 |
| 3A | GACCCAGGCTGAGTGTGTTATC (SEQ ID NO: 98) | GGTGGAAGTTGTGGAGAGATC (SEQ ID NO: 99) | 58 | 324 |
| 3B | ATCTCTCCACAACTTCCACCAG (SEQ ID NO: 100) | CTGCTTCCCTTTCTCAGACACC (SEQ ID NO: 101) | 59 | 488 |
| 4 | TCGTAGACCCCAGTCACATAAC (SEQ ID NO: 102) | ATGTCTTCCTCCAAATGGGTCG (SEQ ID NO: 103) | 60 | 433 |

TABLE 1a-continued

Primers and conditions used for PCR amplification

| Exon | Sense primer (5'–3') | Antisense primer (5'–3') | Annealing (° C.) | Product Size (bp) |
|---|---|---|---|---|
| 5 | AATGCTTCTAGTCAGTGAAGGC (SEQ ID NO: 104) | GCCAGCTTCTTACCCTGGAATA (SEQ ID NO: 105) | 59 | 410 |
| 6 | ATTCCAGTTCCAGGCGAACCCT (SEQ ID NO: 106) | GTCTCCTCCCTCCCTTATTACC (SEQ ID NO: 107) | 59 | 231 |
| 7 | AATTGCAGGTCCAACCCAGTG (SEQ ID NO: 108) | TGCAGTACTGACCTGTGACCA (SEQ ID NO: 109) | 60 | 199 |
| 8A | GTCACAGGTCAGTACTGCAG (SEQ ID NO: 110) | GGAGGTCTTACAAAGGTAAAG (SEQ ID NO: 111) | 59 | 319 |
| 8B | GACAAACTTTTCCTGGACAC (SEQ ID NO: 112) | CACTGTATTGTGTGTAGTCC (SEQ ID NO: 113) | 59 | 302 |

TABLE 1b

Primers used to amplify fragments and methods for haplotype analysis

| Locus | Sense Primer 5'–3' | Antisense Primer 5'–3' | ° C. | Method | Allele (bp) |
|---|---|---|---|---|---|
| D2S2922 | AAAGGGGATGAACCGGGTA (SEQ ID NO: 114) | TTTTCCGAAAGAGGTGTGAC (SEQ ID NO: 115) | 51 | Sau961 | 334, 176, 158 (333) |
| D2S7048 | CGACCAAGACCTGCTTTTG (SEQ ID NO: 116) | TAGGTTTCCCTTCCTCCCT (SEQ ID NO: 117) | 59 | BseR1 | 153, 75, 78 |
| D2S1353 | CCAGGGACATTGCTTAACAT (SEQ ID NO: 118) | GAGCAGGATTTGTAACCCTG (SEQ ID NO: 119) | 54 | (CA) n | 154–164 |
| D2S142 | TGGAGACACTGAACGGGTA (SEQ ID NO: 120) | TGAAAAGTTTTGAGATGGAG (SEQ ID NO: 121) | 56 | (CA) n | 254–266 |
| D2S8336 | TCCTAACCTGCAGGCAGAAC (SEQ ID NO: 122) | CTGAACTGCAACAACCAAGC (SEQ ID NO: 123) | 59 | HDX | 203 |

Genomic DNA was extracted from peripheral blood lymphocytes using a standard phenol-chloroform purification method. DNA was amplified by PCR using sense and antisense primers specific for the 5' flanking region and all exons and the exon-intron boundaries of NURR1 gene. The sequences of the oligonucleotide primers used for the amplification are shown below and in FIG. 1:

| | |
|---|---|
| AAATCCCACCCGAACTGCGTG (SEQ ID NO: 3) | GACACTTCACTTTCCCCGAAG (SEQ ID NO: 4) |
| GCAAGCCACATAAACAAGG (SEQ ID NO: 5) | ACTGCATGGGCTGCATCTACT (SEQ ID NO: 6) |
| GCTTCCTGTGTCTGTATTTCA (SEQ ID NO: 7) | CTACCTTCAGCCGAGTTACAG (SEQ ID NO: 8) |
| ACCCAGGCTGAGTGTGTTATC (SEQ ID NO: 9) | TGCTTCCCTTTCTCAGACACC (SEQ ID NO: 10) |
| CGTAGACCCCAGTCACATAAC (SEQ ID NO: 11) | TGTCTTCCTCCAAATGGGTCG (SEQ ID NO: 12) |
| ATGCTTCTAGTCAGTGAAGGC (SEQ ID NO: 13) | CCAGCTTCTTACCCTGGAATA (SEQ ID NO: 14) |
| TTCCAGTTCCAGGCGAACCCT (SEQ ID NO: 15) | GTCTCCTCCCTCCCTTATTACC (SEQ ID NO: 16) |
| ATTGCAGGTCCAACCCAGTG (SEQ ID NO: 17) | GCAGTACTGACCTGTGACCA (SEQ ID NO: 18) |
| GTCACCAGACTGGAAAATTC (SEQ ID NO: 19) | TAACACCGTCCAACATTCCT (SEQ ID NO: 20) |

All PCR reactions were performed in a 25 µl reaction volume containing a mixture of 1.5 mM MgCl$_2$, 0.2 mmol of each dNTP, 5 pmol up primer, 5 pmol low primer and 2.5 U of HotStart Taq (QIAGEN; Valencia, Calif.) DNA polymerase. After a 10 minute (min) denaturation step at 95° C., the PCR reaction consisted of: (a) 35 cycles of 94° C. for 45 sec, annealing 58° C.–62° C. respectively for 45 seconds (sec), and 30 sec at 72° C.; (b) a final 10 min extension at 72° C. The PCR products were visualized on 0.8% agarose gel stained with ethidium bromide.

HDX analysis was carried out with MDE™ Gel solution (FMC; Philadelphia, Pa.). After thermal cycling of genomic DNA, inactive DNA polymerase was inactivated by adding EDTA to a final concentration of 5 mM (1 µl of 0.5 M EDTA per 100 µl reaction) according to the manufacturer's recommendations. The reaction mixture was heated for 3 minutes at 94° C., then slowly (1° C./minute) cooled to room temperature (37° C.). Triple dye loading buffer 1 µl (FMC; Philadelphia, Pa.) was added to each 5 µl of sample and mixed well. Gels were run at a constant voltage of 20 V/cm. The power supply may be set for 1500–1900 volts for a 60 cm plate. DNA bands were visualized after silver staining.

The abnormal PCR products detected by HDX analysis were separated on a 1.5% agarose gel. The products were excised from the gel, purified using a QIAEX II gel extraction kit (QIAGEN) and processed for direct sequencing in both directions by the dideoxy chain terminator method using an automated sequencer (Applied Biosystems; Weiterstadt, Germany).

Direct sequencing of the genomic DNA specimens detected a heterozygous variation in the exon 1 of the NURR1 gene in 10 of 107 fPD, verifying that the exon 1 fragment encoding the variant of the NURR1 gene had been subcloned. The PCR amplified NURR1 gene fragment was ligated into pGEM-T Easy Vector (Promega; Madison, Wis.) overnight at 4° C. and then transformed into JM109 cells. The insert clones were selected using standard procedures. Single colonies of plasmid DNA were isolated using the Wizard Plus Minipreps DNA purification system (Promega; Madison, Wis.) for sequence analysis.

The 7048G7049 polymorphism in intron 6 of NURR1 gene creates a deletion of the BseR1 recognition site. To determine the frequency and the heterozygous/homozygous state of the deletion BseR1 recognition site, a gene fragment containing the entire intron 6 and part of exon 5 and 7 was amplified by PCR and digested with BseR1.

Primers used in the amplification were:

5'-GGG ATA TCA TGT GGA CAA ACC-3' (SEQ ID NO:21)

5'-GAA GCA TGG GAA ACG TGT GTC-3' (SEQ ID NO:22).

The annealing temperature was set to 59° C. The PCR product was digested with 5 units of BseR1 (New England Biolabs) for 16 hr. at 37° C., and the digestion products were visualized by staining with ethidium bromide on a 2% agarose gel.

To determine the functional consequence of the exon 1 variant of NURR1 gene on NURR1 gene expression and DAergic phenotype, the human NURR1 gene encoding the −291-T-del was reconstructed. Human genomic DNA for NURR1 (GenBank Accession No. ABO17586; SEQ ID NO:43) was cloned into the NotI site of the expression vector pCMX. The T deletion and the T to G substitution in the first exon of the NURR1 gene were isolated by PCR amplification of the genomic fragment between restriction sites BstB 1 and NruI. The resulting PCR fragment was subsequently subcloned into the pGEM vector (Promega) and fully sequenced. No nucleotide alterations were detected. Site-directed mutagenesis (QuikChange Site-directed mutagenesis kit from Stratagene (La Jolla, Calif.)) was performed in the pGEM vector into which wild-type pCMX-NURR1 had been constructed using long-distance PCR (Clontech Laboratories, Inc.; Palo Alto, Calif.). The mutated fragment was excised by BstBI and NruI digestion and subcloned into the corresponding region of pCMX carrying the otherwise wild-type NURR1 gene into the same vector pCMX. The positive strain was screened out and confirmed by DNA sequencing.

In some embodiments, the primers used to generate the −291-T-del mutant NURR1 genomic segment were:

5'-GGC TCC GCG GTC CCT TTG CCT TTG CCT GTC CAG CCG GCC G-3' (SEQ ID NO:23)

5'-CGG CCG GCT GGA CAG GCA AAG GGA CCG CGG AGC C-3' (SEQ ID NO:24).

In some embodiments, the primers used to generate the −245T-G-sub mutant NURR1 genomic segment were:

5'-GCT CCC TCC CTC CGT GAG GGG TCC GGG TTC CCT TTC-3' (SEQ ID NO:25).

5'-GAA GGG AAC CCG GAC CCC TCA CGG AGG GAG GGA GC-3' (SEQ ID NO:26).

HEK-293 cells were used for NURR1 gene transfection. The cells were maintained in Dulbecco's modified Eagle medium (DMEM) supplemented with 10% fetal calf serum (FCS). Transfections were performed in 60 mm dishes using the procedure described in the FuGENE™ 6 kit (Roche; Basel, Switzerland). Briefly, the day prior to transfection, cells were seeded at a density of 6×10⁵ cells/dish. Each dish was treated with 2 μg of the indicated expression vectors. The cells were harvested after 36–48 hr and the total RNA was isolated from cells using Trizol Reagent (GIBCO BRL).

cDNA synthesis was performed using the display THERMO-RT kit (PGC Scientific; Frederick, Md.). Three μl of cDNA was used for each PCR reaction. RT-PCR products were analyzed by agarose gel electrophoresis and DNA bands were quantified using Bio-Rad Quantity One quantitation software. The following primers were used to amplify GAPDH target cDNA:

5'-GGA TTT GGTCGTATTGGGCGCCTGG-3'(SEQ. ID NO:27);

5'-CCCTGCAAATGAGCCCCAGCCTTCT-3'(SEQ. ID NO:28);

The following primers were used to amplify NURR1 target cDNA:

5'-GCA GAG AAG ATC CCT GGC TTC GC-3'(SEQ. ID NO:29);

5'-CGC ATT GCA ACC TGT GCA AGA CC-3'(SEQ. ID NO:30).

The cells were cultured with D-MEM medium in a 60 mm dish and total RNA was extracted using SV total RNA isolation system. Three primer pairs were designed to amplify the sequence of exon 1–2 (144 bp), exon 1–3 (390 bp) and exon 5–7 (396 bp) of NUR Two step RT-PCR (Qiagen; Valencia, Calif.) was performed according to the manufacturer's instructions. A 540-bp fragment was amplified from β-actin and a 270-bp fragment was amplified from pSV-β-galactosidase. RT-PCR profiles were visualized by ethidium bromide staining of a 1% agarose gel, and the signal density of the amplified band was measured using Quantity One software (Bio-Rad Laboratories; Hercules, Calif.).

Genotype analysis. The genotype analysis on the polymorphism of SNPs (D2S2922, D2S7048, D2S8336) and microsatellites (D2S1353 and D2S142) were conducted using PCR-restriction fragment length polymorphism (RFLP) or PCR-HDX analysis, respectively. DNA was amplified by PCR using primers specific for those SNP and microsatellite markers (Table 1).

Cell transfection and RT-PCR. HEK293 cells or SH-5YSY cells (6×10⁶ cells/60 mm² dish) were treated with 2 μg of the expression vectors. The cells were harvested after 36 hr and the total RNA was extracted using SV total RNA isolation system. Primer targeting the sequence of NURR1 exon5–7 (396 bp; 5'-GCATTGCAACCTGTGCAAGAC-CAC-3' (SEQ ID NO:89); 5'-GTTT GCCCTCGAAAAC-CGA AGAGC-3' (SEQ ID NO:90) were designed to measure NURR1 mRNA. β-actin and β-gactactosidase were used as an internal control and transfection efficiency control, respectively.

Transcription activity assay. A luciferase reporter plasmid containing tandem NuRE sites was generated by ligating the annealed fragments upstream of the herpes simplex thymidine kinase promoter fused to luciferase gene (Provided by Dr. Roy G. Smith, BCM). Luciferase activity of the transfected cell extracts was determined by luminometer/photometer reader (TD-20/20; Promega; Madison, Wis.).

Quantitation of NURR1 mRNA levels by real-time PCR. Total RNA was extracted from lymphocytes or transfected HEK293 cells and SH5YSY cells using the SV total RNA isolation kit (Promega; Madison, Wis.). NURR1 primer (5'-aactctgctgaagccatgc-3; (SEQ ID NO:91) 5'-gagaagc-cctcttatgtcga-3' (Invitrogen; Carlsbad, Calif.) (SEQ ID NO:92) and TaqMan probe (5'FAM-ctcgcctcaaggagccagc-cccgctt-BHQ1, IDT Inc.) (SEQ ID NO:93) was synthesized based on the sequence exon 3–4 of NURR1 cDNA. The experimental reaction consisted of 40 cycles of 94° C. for 50 sec, 59.5° C. for 50 sec and was carried out in the Bio-Rad iCycler System (Bio-Rad Laboratories; Hercules, Calif.). NURR1 transcripts quantified from real-time PCR were normalized against GAPDH transcripts.

EXAMPLE 2

Detection of Mutations in PD Samples

Ten ml of peripheral blood was withdrawn from PD and control subjects. Genomic DNA was extracted from the lymphocytes using standard techniques. Nine fragments of the NURR1 gene, covering the 8 exons and part of the introns, were amplified by PCR. To detect any putative mutations in the NURR1 gene, single strand conformational polymorphism (SSCP) analysis of all of the PCR amplified fragments was performed with MDE™ Gel solution (FMC Bioproducts). The abnormal PCR products detected with heteroduplex (HDX) bands by SSCP analysis were processed for direct sequencing.

To investigate whether genetic variations of NURR1 may occur in PD, we conducted a mutation analysis from the lymphocyte-derived genomic DNA from well-documented 201 PD patients (107 fPD and 94 sPD) and 221 age-matched NC. Ten fragments of the NURR1 gene covering all 8 exons and parts of introns were amplified by PCR and the variations in the fragments were detected by heteroduplex (HDX) analysis. Although several HDX variations were detected, one HDX variation in the exon 1 and another HDX variation in the intron 6 was clearly shown association with PD. Among the 201 PD patients and 221 NC subjects, 10/107 fPD but 0/94 sPD and 0/221 NC had HDX variation in the exon 1 fragment.

Figure 2:
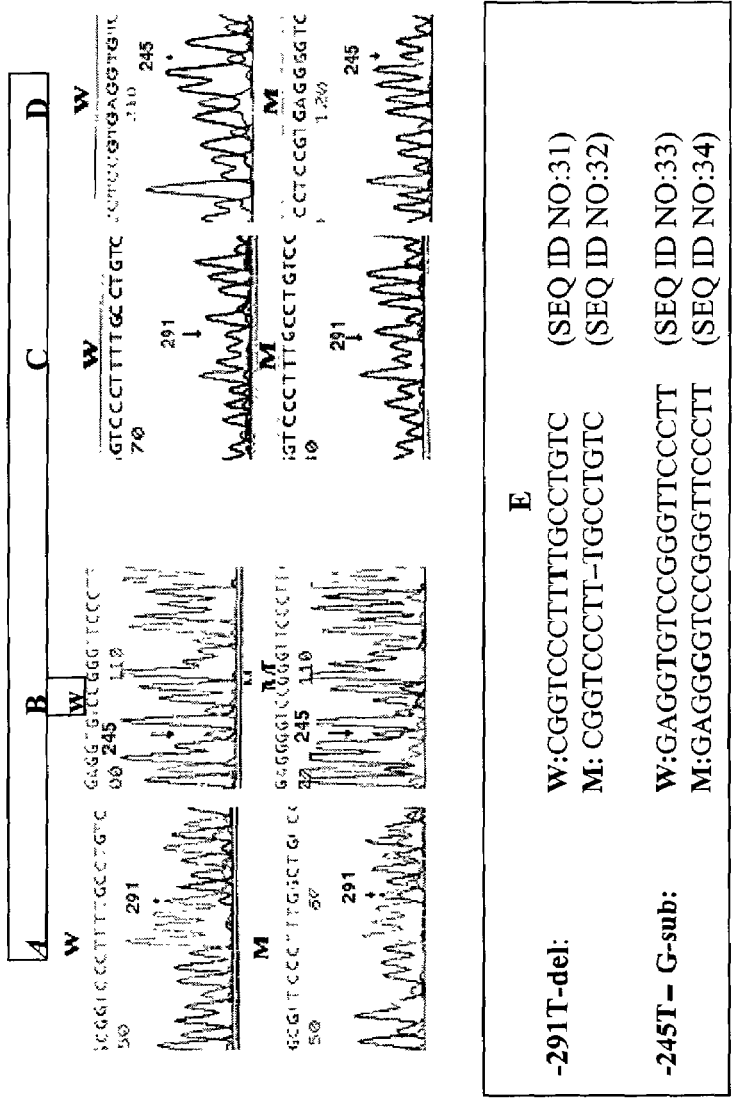
FIGS. 2A through 2E demonstrate sequencing analysis of the first exon of NURR1.

Direct sequence analyses of the PCR products from the 12 fPD specimens identified two heterozygous point mutations in exon 1 of the NURR1 gene. In FIG. 2E, the normal wild-type sequence (SEQ ID NO: 31) is shown above the −291T-del mutant sequence (SEQ ID NO. 32). Although the inventors previously referred to the first of the mutations as a T deletion located in the base pair position 1091 (previously referred to as 1091-T-del) of NURR1 gene (for example, in Accession No. BC009288; SEQ ID NO:94), to define the location more precisely the same mutation is hereafter referred to as −291-T-del, which is a T deletion at transcribed nucleotide position −291 upstream of the initiator AUG codon of NURR1. Furthermore, the second mutation was a T-G substitution located in the base pair position 1137 (previously referred to as 1137-T-G-sub) of NURR1 gene. Again, to define the location more precisely, the same mutation is now referred to as −245T-G-sub, which is a T-G substitution at transcribed nucleotide position −245 upstream of the initiator AUG codon of NURR. Again, to illustrate, one mutation, detected in 8 (7.5%) fPD patients, was a T deletion at transcribed nucleotide position −291 (−291T-del; FIG. 2A) upstream of the initiator AUG codon of NURR1 (for example, in Accession No. BC009288; SEQ ID NO:94). The second mutation detected in 2 fPD patients (1.8%), was a T to G substitution at transcribed nucleotide position −245 (−245T to G-sub; FIG. 2B). These mutations were further verified by subcloning (FIGS. 2C and 2D). A skilled artisan recognizes the sequence following the deletion in FIG. 2A of wild-type compared to the mutant is inconsistent, due to heterozygosity. In a specific embodiment, the mutation comprises SEQ ID NO:124.

TABLE 2

The frequency of two putative mutations in exon 1 of the NURR1 gene in fPD, sPD and normal controls.

| Variation location | fPD | sPD | Control |
| --- | --- | --- | --- |
| Exon 1 (-(291-T-del) | 8/107 (7.4%)** | 0/120 (0%) | 0/221 (0%) |
| Exon 1 (-245T→Gsub) | 2/107 (1.9%)* | 0/120 (0%) | 0/221 (0%) |
| Intron 4 heterozygous(5459G→Asub) | 0/107 (0%) | 1/94 (1%) | 0/221 (0%) |
| Intron 6 homozygous(7048G7049) | 10/105 (9.3)** | 5/94 (4.2)* | 2/221 (0.9%) |
| 5' frank heterozygous | 15/107 (14%) | 12/94 (12.7%) | 29/221 (13.1%) |

*p < 0.01 and **p < 0.001 vs sPD or Controls. Fisher-Exact Test.

The region of exon 1 where the −291-T-del mutation occurs is a regulatory (non-coding) region of the NURR1 gene and, therefore, may not result in a frame shift of the amino acid sequence of the gene expression product. The location of the −291-T-del mutation in a regulatory domain of the NURR1 gene suggests that the mutation has an important effect on the expression of the NURR1 gene and may be a suitable prophylactic or therapeutic target.

Thus, in FIG. 2E the normal wild-type sequence (SEQ ID NO: 33) is shown above the second variant mutation. The second variant, −245T-G-sub (SEQ ID NO. 34) that has been detected in 2 fPD patients is provided (1.9%, Table 2). No mutations were found in DNA specimens from sPD (n=94) and in normal controls (n=221) (Table 2). Sequencing analyses in these fPD patients has been repeated 2–3 times for verification.

Figure 3:
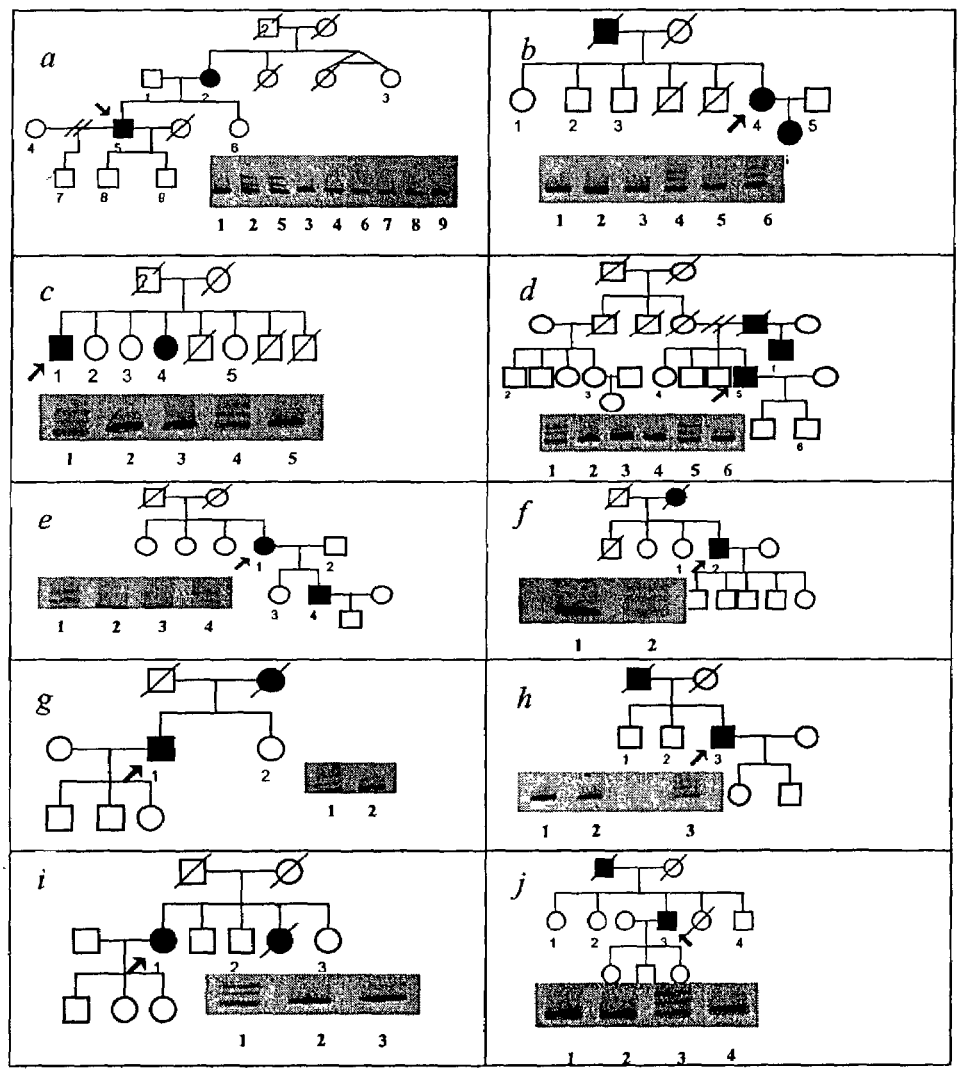
FIG. 3 shows genotype and phenotype analysis in the families (FIGS. 3A through 3J) of 10 fPD patients with identified −291-T-del or −245-T-G-sub mutations. Filled symbols represent affected individuals with PD, which correlated well with abnormal HDX bands below. Direct sequencing analysis demonstrated that PD patients with the a–h families have −291-T-del, and PD patients in the i–j families have −245-T-G sub in the first exon of the NURR1 gene.

Based on Fisher's exact test the confidence levels are p<0.00005 for fpD vs. NC and p<0.0019 for fPD vs. sPD. Therefore, these findings are highly significant. Furthermore, the mutation analysis was performed in 78 available members from the 10 fPD families. The −291T-del or −245T-G-sub mutations were found only in PD patients, clearly indicating a segregation of genotype and phenotype (FIG. 3). The onset of the disease in these 10 fpD patients ranged from 45 to 67 yrs with mean 54±7 yrs, a typical age for the onset of PD. The clinical features of these patients were no different from typical PD. The affected individuals are members of ten apparently unrelated Caucasian families of English (2), French/Hispanic (1), German/Czech (1), German/English/Irish (1), Hispanic (1), Irish/Czech (1), Norwegian/English (1), Polish/Hispanic (1), and Russian/Polish/Jewish (1) origins. Eight of the ten affected individuals (7 with −291T-del and 1 with −245T-G-sub) have clear PD family history involved in at least two generations. The other two have siblings with PD. However, their parents' PD status is unknown because they had died in their third and fourth decade of life, possibly before PD symptom(s) appeared. Thus, it could not be determined whether PD was present in these two families for more than one generation. Haplotype analysis was performed in available four pedigrees of the ten fPD families using two microsatellite markers (D2S1353, D2S142) in the distance of 50 kb from NURR1 gene, and three SNP markers (D2S2922, D2S8336 and D2S7048) inside the NURR1 gene (Table 1 and FIG. 4A; all are selected from Genehunter Website).

Figure 4:
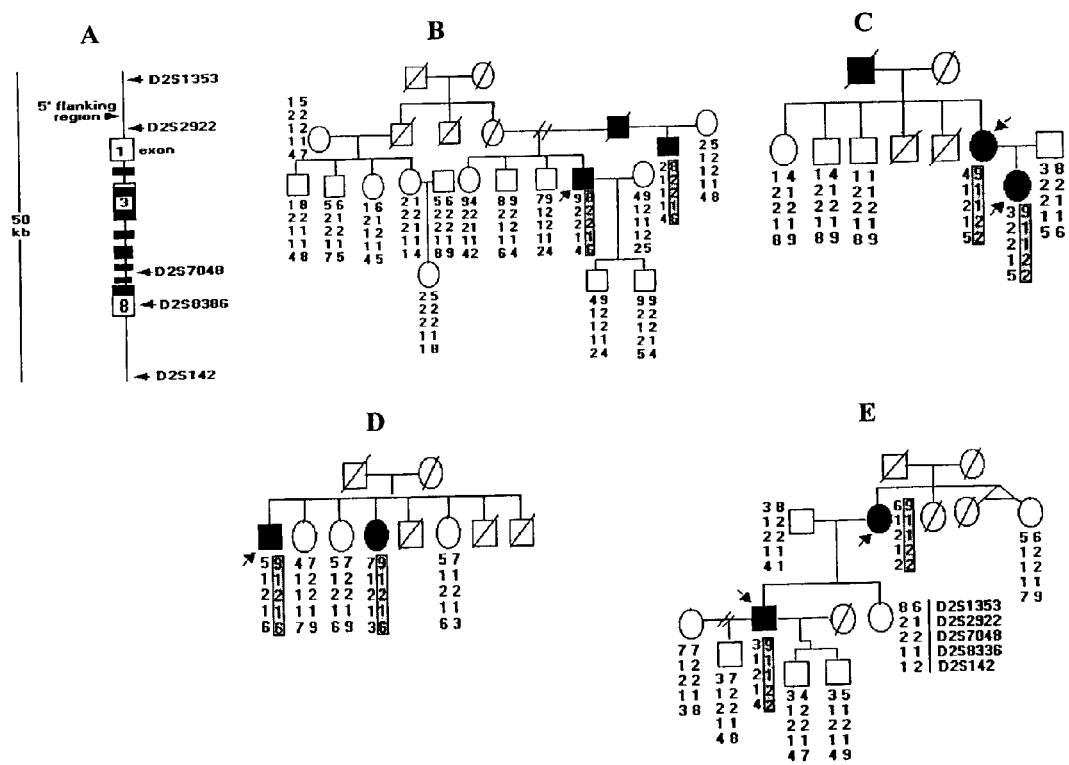
FIGS. 4A through 4E show five haplotype markers used for genotype analysis.

Two haplotypes were identified: one is (8-2-2-1-6) shared by two PD patients from one family with Caucasian-Hispanic background (FIG. 4B), and another is (9-1-1-2-2) shared by six PD patients from different three families that originally came from West European countries (FIGS. 4C, 4D and 4E).

In addition to the exon 1 mutation, a polymorphism (7048G7049 insertion) was found in intron 6 of NURR1 gene. This insertion is 18 bases downstream of the border to exon 6 and is in the region of the ligand-binding domain. The 7048G7049 polymorphism in intron 6 creates a deletion of the BseR1 recognition site. By use of a BseR1 restriction enzyme assay, it was determined that a 7048G7049 heterozygote was detected in 24 of 109 fPD (22.0%), in 25 of 120 sPD (20.8%) and in 45 of 221 normal controls. (20.3%) (Table 3).

mice develop behavioral and biochemical changes consistent with parkinsonism (Le et al., 2001).

EXAMPLE 3

Functional Assay to Characterize Mutations

Since exon 1 is fully transcribed and is in the region of the regulatory complex of the NURR1 gene (Torri et al., 1999), a functional assay was established to elucidate whether the −291-T-del and −245T-G-sub mutations affected the expression of the NURR1 polynucleotide. The −291-T-del and the −245T-G-sub were constructed in a full-length human NURR1 polynucleotide using PCR site-directed mutagenesis. After construction, transformation and re-ligation, the positive clone was screened out and confirmed by DNA sequencing.

TABLE 3

Frequency of 7048G7049 polymorphism in PD patients and in normal controls.

| | Controls | | All PD patients | | | fPD patients | | | sPD patients | | |
|---|---|---|---|---|---|---|---|---|---|---|---|
| | N | % | n | % | $\chi^2$ | n | % | $\chi^2$ | n | % | $\chi^2$ |
| Wild-type | 174 | (78.7) | 162 | (72.0) | 2.72 | 72 | (68.6) | 3.97 | 90 | (75.0) | 0.62 |
| Heterozygous | 45 | (20.3) | 48 | (21.3) | 0.06 | 23 | (22.0) | 0.10 | 25 | (20.8) | 0.10 |
| Homozygous | 2 | (0.90) | 15 | (6.7) | 10.09** | 10 | (9.5) | 14.91*** | 5 | (4.2) | 4.11* |

$\chi^2$ was analyzed in all PD (fPD + sPD), fPD and sPD as compared with normal controls.
*p < 0.05, p < 0.005, and *p < 0.001

TABLE 4

Mantel-Haenszel odds ratio estimates for the effect of homozygous 7048G7049 polymorphism on the risk of PD.

| Factor | OR | 95% CI | PValue |
|---|---|---|---|
| 7048G7049 heterozygote | 1.1 | 0.7, 1.8 | 0.36 |
| 7048G7049 homozygote | 8.4 | 1.9, 37.1 | 0.0042 |

Odds ratios for carrier and homozygote of 7048G7049 were performed in the entire samples including all PD and controls.

The frequency analysis of the 7048G7049 heterozygote in these groups suggested no significant difference ($\chi^2$ test). A 7048G7049 homozygote was detected in 10 of 109 fPD (9.1%) and in 5 of 120 sPD (4.2%) which is significantly different from normal controls (2 of 221; 0.9%) (Table 4). The patients with the homozygous 7048G7049 polymorphism do not overlap with the documented exon 1 mutations.

Thus, the third variation (7048G7049) in the NURR1 gene is located in intron 6 near the juncture of exon 6 as a part of the ligand-binding domain (Buervenich et al., 2000). The frequency of the homozygous 7048G7049 polymorphism is significantly higher in both fPD and sPD, indicating, in specific embodiments, that the homozygous polymorphism is an important genetic risk for PD. These data match previous experimental results using heterozygous NURR1 knock-down mice (NURR1+/−) that displayed low levels of striatal DA at their advanced age and were more susceptible to the effects of MPTP than were wild-type NURR1+/+ mice (Le et al., 1999b). One recent study by the present inventor suggests that with aging these NURR1+/−

Figure 5A:
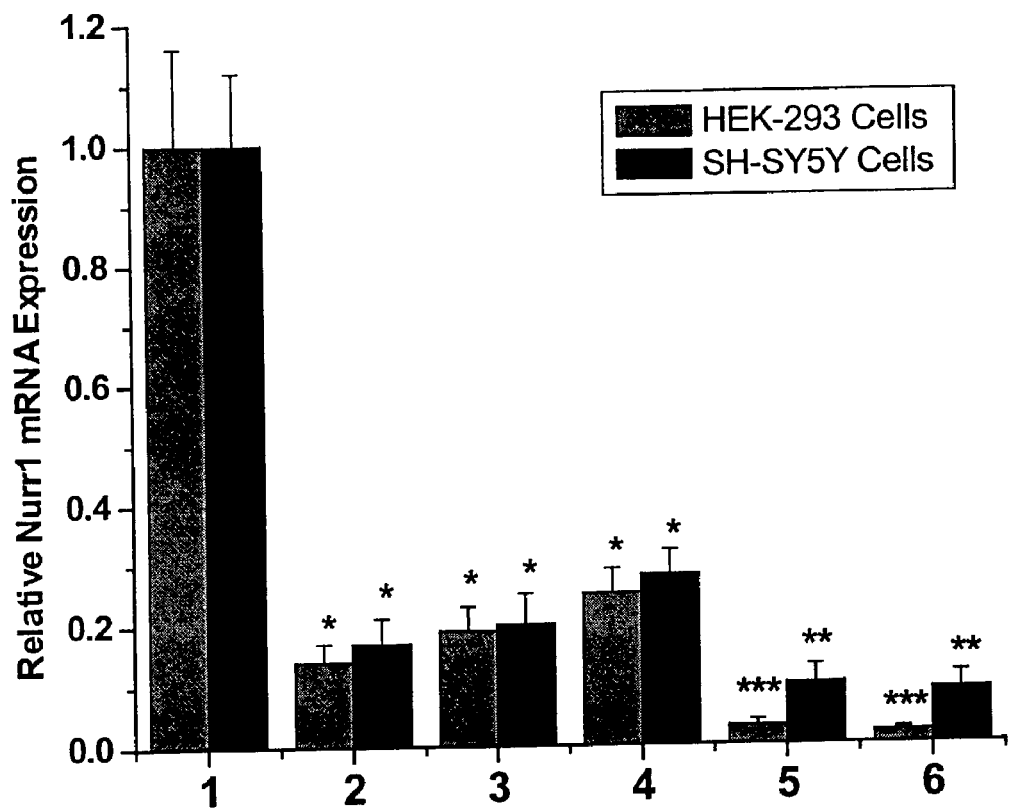
FIGS. 5A through 5F show RT-PCR and RT-coupled real-time PCR.
Figure 5B:
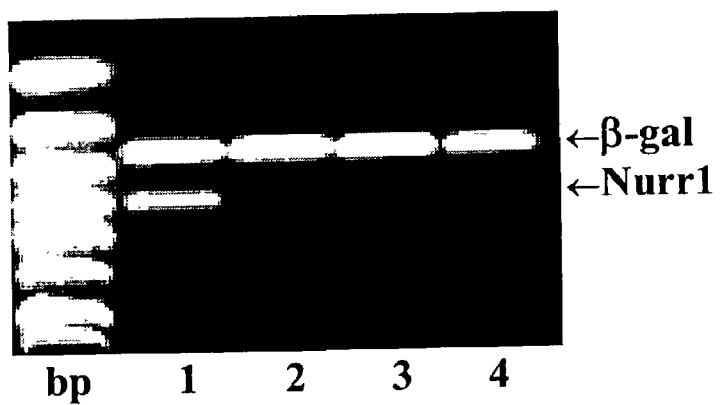
Figure 5C:
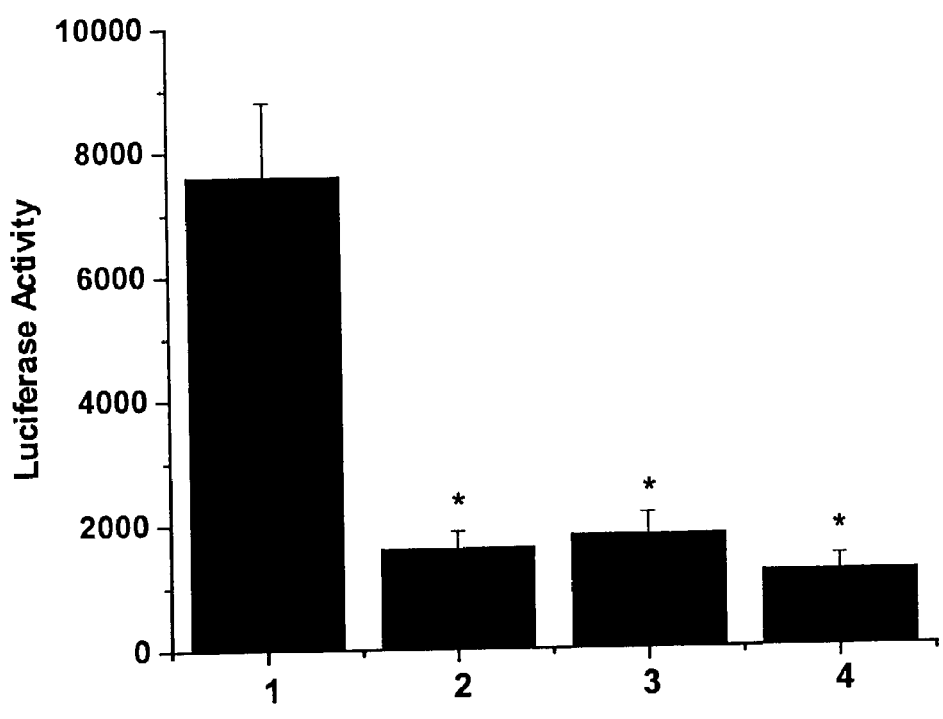
Figure 5D:
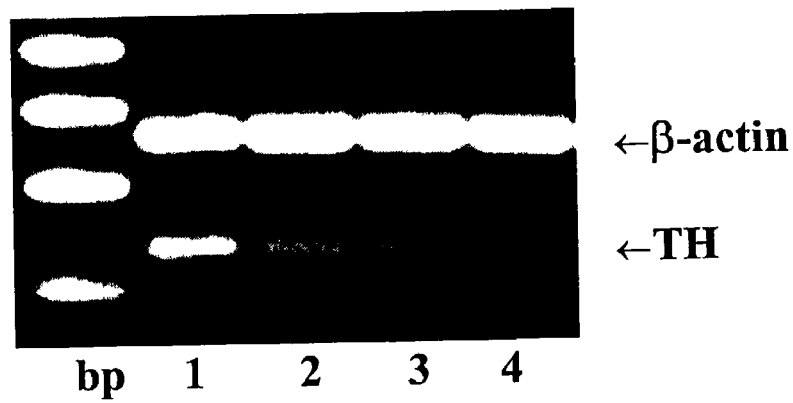

In order to determine if the NURR1 gene mutations could either cause PD or be linked to other mutations, a functional assay was established to elucidate whether the −291T-del and −245T-G-sub mutations affect NURR1 gene expression and/or DAergic function. The −291T-del or −245T-G-sub mutations were incorporated in a full-length human NURR1 gene using PCR site-directed mutagenesis. The expression vectors harboring the mutant (−291T-del or −245T-G-sub) or the wild-type NURR1 gene were transfected into the human embryonic kidney cell line HEK293 or human neuroblastoma cell line SH-5YSY. The expression levels of the transcripts arising from the transfected genes were measured by real time PCR. The cells transfected with the mutant NURR1 gene encoding the −291T-del or −245T-G-sub produced 87–95% less NURR1 mRNA as compared to the cells transfected with the wild-type NURR1 gene (FIG. 5A). Interestingly, the cells cotransfected wild-type and −291-T-del mutant gene also resulted in over 70% reduction in NURR1 expression, suggesting a negative dominant effect may play a role in dictating NURR1 expression (FIG. 5A). As a control for cell transfection efficiency, he NURR1 gene was co-transfected along with the β-galactosidase gene. The β-galactosidase mRNA were constant in all transfections while NURR1 mRNA levels were significantly low in mutant NURR1 gene transfected cells (FIG. 5B). To further verify that there were negative effects of −291T-del or −245T-G-sub mutation on NURR1 gene expression, a reporter plasmid containing tandem NuRE sites upstream of the herpes simplex thymidine kinase promoter fused to the luciferase gene was co-transfected into SH-5YSY cells. As shown in FIG. 5C, the luciferase activity was reduced by more than 75% in both mutant NURR1 genes transfected cells as compared to the wild type control. Furthermore, the TH expression was measured in the transfected HEK293 and SH-5YSY cells and found that TH mRNA in the two mutant gene transfected cells was significantly lower than in the wild-type NURR1 gene transfected cells (FIG. 5D).

Figure 5E:
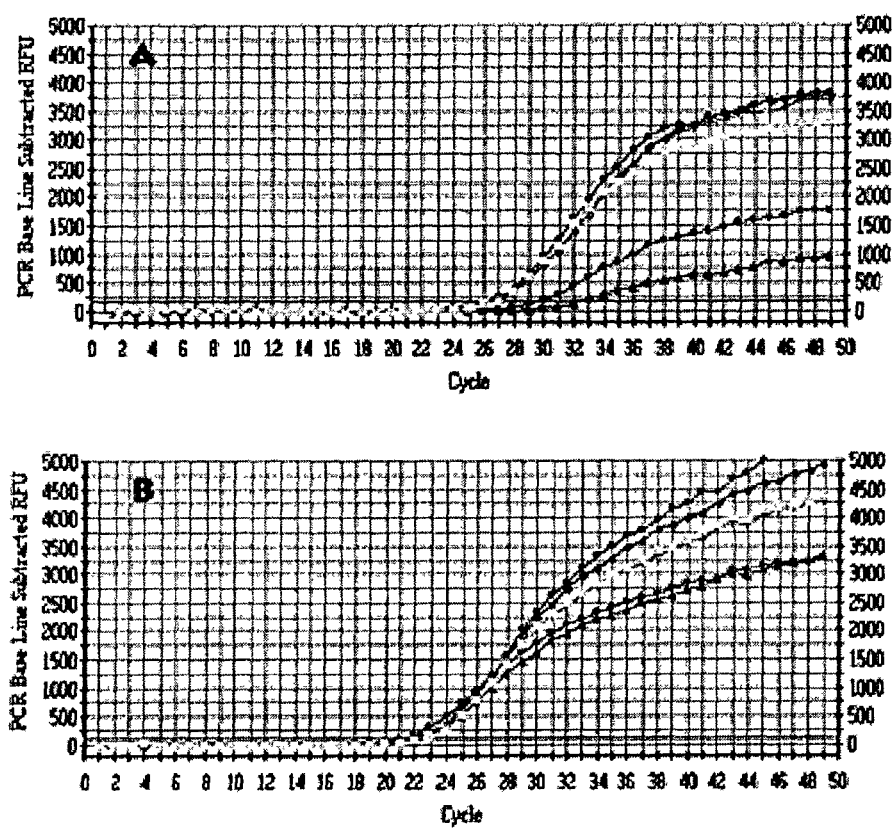
Figure 5F:
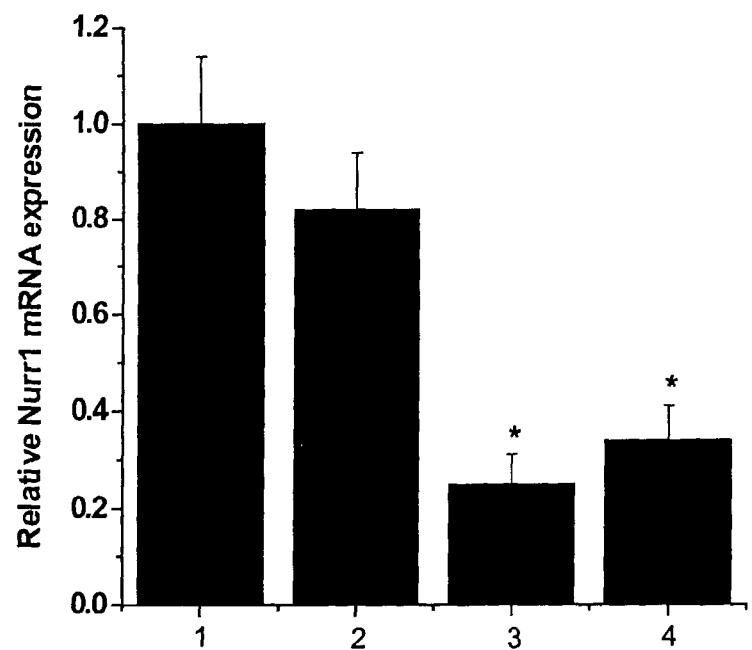

Taking advantage of the fact that NURR1 is expressed in human lymphocytes (Mages et al., 1994). It was tested whether there was an alteration in NURR1 expression in vivo due to the exon 1 mutations. The relative NURR1 mRNA levels were measured from the lymphocytes of two PD patients with −291-T-del and their three non-PD family members by real time PCR. A significant reduction of NURR1 mRNA was detected in the two PD patients as compared to their three non-PD family members (FIGS. 5E and 5F).

Figure 6:
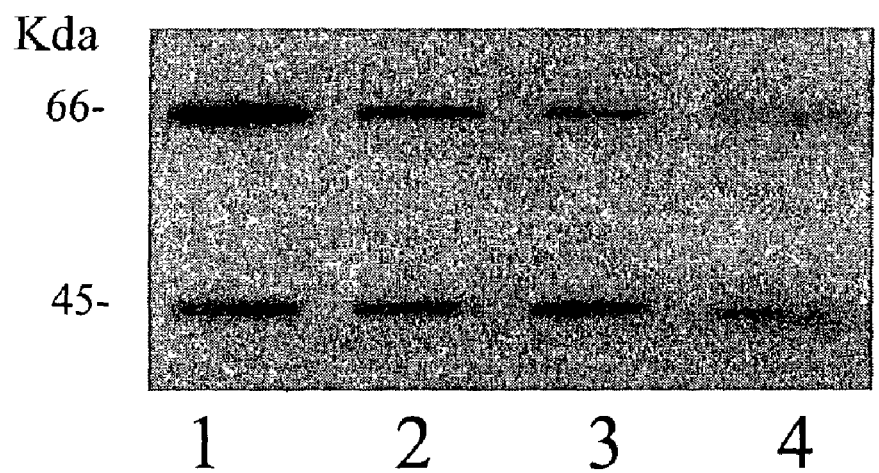
FIG. 6 demonstrates immunoblot with Nurr1 protein levels associated with the mutations. Lanes 1, 2, 3, 4 represent cells transfected with NURR1 gene encoding wild-type, −291-T-del, −245-T-G mutation, or vector alone, respectively.

FIG. 6 illustrates NURR1 protein levels in transfected SH5YSY cells harboring the mutations, by providing immunoblot with polyclonal antibody against N-terminal of NURR1 that responds to a 66-Kda band. Beta-actin was used as an internal control. Nurr1 protein levels were greatly decreased in cells transfected with each of the mutations.

Figure 7:
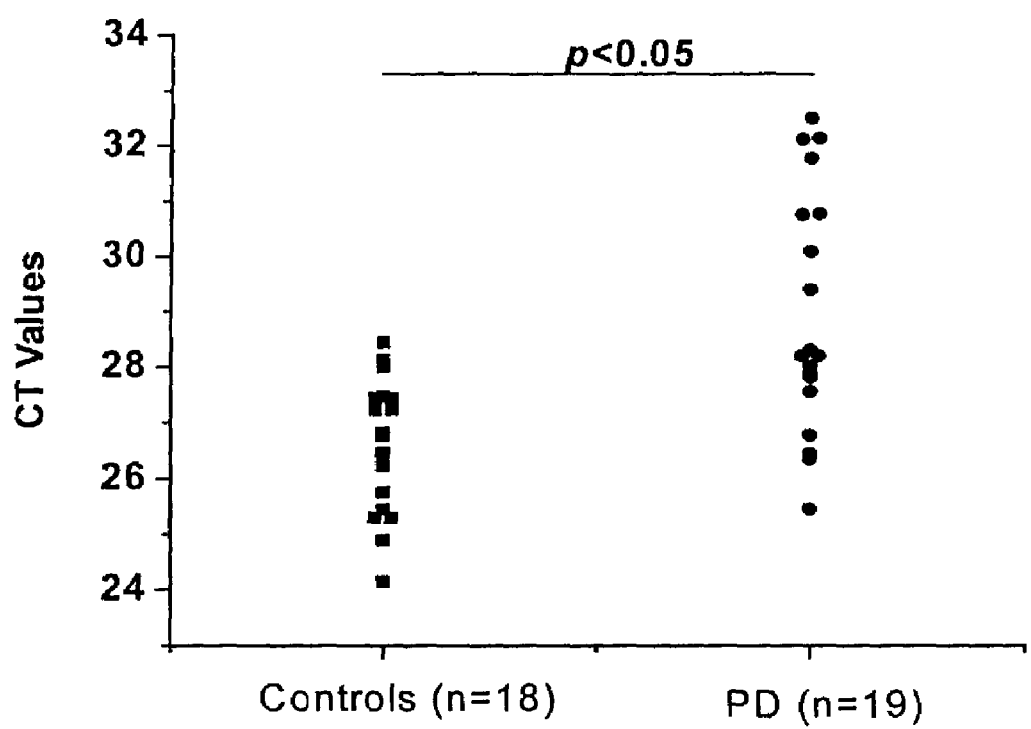
FIG. 7 provides real-time PCR measurement of NURR1 mRNA in the lymphocytes of 19 PD patients (62±9.5 yr old) and 18 NC (64±11 yr old). Higher CT (threshold cycles) values indicate lower levels of RNA.

In FIG. 7, real-time PCR measurement of NURR1 mRNA in the lymphocytes of 19 PD patients (62±9.5 yr old) and 18 NC (64±11 yr old) indicated a moderate by significant reductions of NURR1 mRNA in PD vs NC. Higher CT (threshold cycles) values indicate lower levels of mRNA. Each experiment was conducted with triplicate determinations. PBL was separated by Ficoll gradient centrifugation, and then the total RNAs were isolated from them. Real-time RT-PCR with total RNA extracted from the cells was used to analyze expression of NURR1 gene.

The identified two mutations have not been reported in the literature or in the Celera's Genomics Data-Base (PBU-HmanRefSNPs). The −291T-del and −245T-G-sub map within the first exon of NURR1 and the function of this region is unknown (Ichinose et al., 1999.) Although only two specific mutations were identified in the NURR1 gene in 10 Caucasian fPD patients, these mutations occur in other ethnic groups, in specific embodiments. Furthermore, there may be identified other PD-related variations in the NURR1 gene in a larger or different disease population. Genotyping in four complete pedigrees suggest existence of at least two distinct founders for the identified NURR1 gene mutations.

The virtual elimination of NURR1 mRNA from the affected allele due to either of these mutations in exon 1 in specific embodiments changes the stoichiometry of the NURR1 protein in relation to the cofactors forming the relevant transcription complexes. This has demonstrated effects on dopamine biosynthesis but additionally in specific embodiments it is affecting other genes whose expression is dependent upon NURR1 (Iwawaki et al., 2000). Such potential defects during the lifetime of an individual may result in neuronal degeneration and the manifestation of PD. Nevertheless, the finding that exon 1 mutations in the NURR1 gene in humans are associated with PD leads to therapeutic interventions, as well as serve as a diagnostic approach for individuals at risk of developing the disease.

EXAMPLE 4

NURR1 Splicing Variant

FIG. 8 illustrates a fourth NURR1 mutation of the present invention, which is a splicing variant of wild type NURR1 identified in human lymphocytes. RT-PCR products of the NURR1 gene exon 5–7 fragment: TCTCCCCTTCGC-CCCCGGTGAGTCTGATCAGTGCCCTCGT-CAGGGCCCATGTCGACT CCAACCCGGCTATGAC-CAGCCTGGACTATTCCAGGTTCCAGGCGAACCCT GACTA (SEQ ID NO: 35) indicate a dominant form that migrates on a gel as an upper band and a splicing variant that migrates on a gel as a lower band. Sequencing analysis of the two bands demonstrates a deletion of 75 nucleotides in the middle of exon 5 of the NURR1 gene in the splicing variant: TCTCCCCTTCGCCCCCG . . . TTCCAGGCGAACCCT-GACTA (SEQ ID NO:36).

The direct assay of NURR1 mRNA levels in PD patient lymphocytes detected altered NURR1 gene expression as a result of NURR1 gene mutations. NURR1 mRNA from the lymphocytes of PD patients with −291-T-del were assayed directly. Lymphocytes were collected by gradient centrifugation with Ficoll density from 5 ml whole blood samples from patients with PD or normal controls. Total RNA was extracted using the SV total RNA isolation system (Promega; Madison, Wis.). Three pairs of primers targeting to amplify the fragments of exon1–2 are as follows: GAGC-TACAGTTACCACTCTTCGGG-3'(SEQ ID NO: 37), 5'GGTGGACAGTGTCGTAATTC-3' (SEQ ID NO: 38), exon 1–3: 5'-GGAACTG CACTTCGGCAGAGTT-3' (SEQ ID NO: 39), 5'-GTTTGCCCTCGAAAACCGAAGAGC-3' (SEQ ID NO: 40), exon 5–7: 5'-GCATTGCAACCTGTG-CAAGACCAC-3' (SEQ ID NO: 41) and 5'-CGCATTG-CAACCTGTGCAAGACC-3' (SEQ ID NO:42). Two-step RT-PCR reaction (QIAGEN) was performed according to the manual instructions. The annealing temperature was set up at 60° C., and a 540 bp fragment was amplified from β-actin as internal control using two-step RT-PCR. RT-PCR profiles were visualized by EB staining on 1% agarose gel and the signal density of the amplified band was measured using Quantity One software (Bio-Rad Laboratories; Hercules, Calif.). Analysis of the gels revealed that, as compared to normal controls, the NURR1 mRNA detected from the exon 5–7 regions was reduced by 84% in fPD patients with −291-T-del. The NURR1 mRNA detected from the exon 1–3 and 1–2 regions was reduced by 68–80% in fPD patients with −291-T-del as compared with normals controls.

Figure 9:
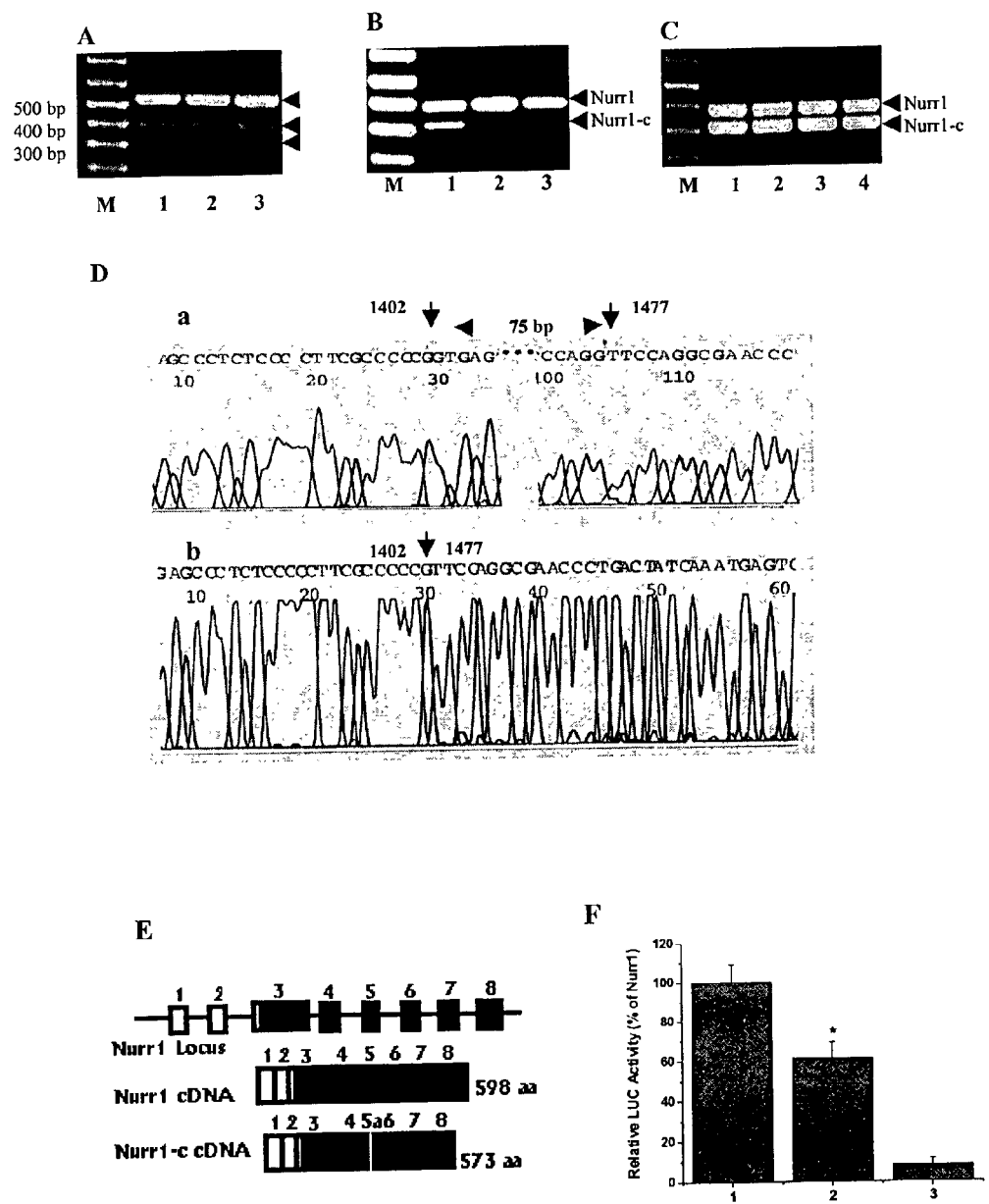
FIG. 9 illustrates sequencing analysis of the novel variant NURR1-c at the specific RT-PCR fragment (exon 5–7: 321 bp) amplified from adult human lymphocytes. Arrows in B shows an internal splicing site within exon 5, which results in a 75 bp deletion from nucleotide 1,402 to 1,476 in NURR1 mRNA. A: wild-type NURR1; B: NURR1-c.

The internal splice results in a 75 bp deletion between nucleotide 1,402 and 1,477 in NURR1 mRNA or between nucleotide 5,823 and 5,897 in NURR1 DNA. This splicing variant named NURR1-c does not cause a frame-shift, but produces a deletion of 25 amino acids from the entire length of NURR1 with 598 amino acids. FIG. 9 shows sequencing analysis of the novel variant (termed NURR1-c) at the specific RT-PCR fragment (exon 5–7: 321 bp) amplified from adult human lymphocytes. Arrows in FIG. 9B show an internal splicing site within exon 5, which results in a 75 bp deletion from nucleotide 1,402 to 1,476 in NURR1 mRNA.

EXAMPLE 5

Therapy Utilizing the Present Invention

In specific embodiments of the present invention, genetic defects in NURR1 gene exon 1 impair the expression of the gene as a result of "loss of function", leading to selective DAergic deficiency, and possibly, to neuronal degeneration in nigro-striatal pathway, thus giving rise to a phenotype of PD. In addition, a third variation in the NURR1 gene, homozygous 7048G7049 polymorphism in intron 6, is present in over 9% of fPD and 4.2% of sPD patients. Genetic analysis showed that intron 6 homozygous 704G7049 polymorphism is significantly associated with PD. Intron 6 is located in the exon encoding the ligand-binding domain.

The mutations in NURR1 exon 1, a region functioning for transcriptional regulation, in specific embodiments leads to decreased expression of NURR1 and impaired maintenance of mature nigral DAergic neurons. Thus, the mutations of the present invention in specific embodiments genetically predispose individuals to develop PD.

Thus, in accordance with the present invention, an individual suspected of developing or having Parkinson's disease or any disease related to deficient dopaminergic neurons is tested utilizing the present methods and compositions. Upon identification of at least one defect in NURR1, preferably that associates genotypically with at least one symptom of a neurological disease, the patient is then treated for the disease. For example, a sample of DNA is obtained from a potentially stricken Parkinson's disease patient, and a NURR1 region is analyzed, such as by PCR amplification and sequencing. If one of the mutations disclosed herein or another identified by standard means in the art is detected, the patient begins treatment for the disease, such as by correcting the NURR1 defect, circumventing the NURR1 defect, or pursuing other standard means in the art to treat the disease. In accordance with the present disclosure, a skilled artisan is cognizant of such standard methods and compositions.

REFERENCES

The following references, to the extent that they provide exemplary procedural or other details supplementary to those set forth herein, are specifically incorporated herein by reference.

PATENTS

U.S. Pat. No. 4,683,195
U.S. Pat. No. 4,683,202
U.S. Pat. No. 4,965,188
U.S. Pat. No. 5,840,873
U.S. Pat. No. 5,843,640
U.S. Pat. No. 5,843,651
U.S. Pat. No. 5,846,708
U.S. Pat. No. 5,846,717
U.S. Pat. No. 5,846,726
U.S. Pat. No. 5,846,729
U.S. Pat. No. 5,849,487
U.S. Pat. No. 5,853,990
U.S. Pat. No. 5,853,992
U.S. Pat. No. 5,853,993
U.S. Pat. No. 5,856,092
U.S. Pat. No. 5,861,244
U.S. Pat. No. 5,863,732
U.S. Pat. No. 5,863,753
U.S. Pat. No. 5,866,331
U.S. Pat. No. 5,905,024
U.S. Pat. No. 5,910,407
U.S. Pat. No. 5,912,124
U.S. Pat. No. 5,912,145
U.S. Pat. No. 5,919,630
U.S. Pat. No. 5,925,517
U.S. Pat. No. 5,925,565
U.S. Pat. No. 5,935,819
U.S. Pat. No. 5,928,862
U.S. Pat. No. 5,928,869
U.S. Pat. No. 5,928,906
U.S. Pat. No. 5,929,227
U.S. Pat. No. 5,932,413
U.S. Pat. No. 5,935,791
U.S. Pat. No. 6,284,539
U.S. Pat. No. 6,312,949
U.S. Pat. No. 6,395,546

PUBLICATIONS

Boshart et al., *Cell* 41:521, 1985.
Buervenich, S. et al. NURR1 mutations in cases of schizophrenia and manic-depressive disorder. *Am. J. Med. Gen.* 96, 808–813 (2000).
Castillo, S. O., Xiao, Q., Lyu, M. S., Kozak, C. A., Nikodem, V. M. Organization, sequence, chromosomal localization, and promoter identification of the mouse orphan nuclear receptor nurr1 gene. *Genomics.* 41, 250–257 (1997).
Castillo, S. O. et al. Dopamine biosynthesis is selectively abolished in substantia nigra-ventral tegmental area but not in hypothalamic neurons in mice with targeted disruption of the nurr1 gene. *Mol. Cell. Neurosci.* 11, 36–46 (1998).
Chamberlin et al *Nature* 228:227, 1970.
Chen, Y. H., Tsai, M. T., Shaw, C-K., Chen, C. H. Mutation analysis of the human NR4A2 gene, an essential gene for midbrain dopaminergic neurogenesis, in Schizophrenic patients. *Am. J. Med. Gen.* 108, 753–757 (2001).
Dijkema et al, EMBO J. 4:761, 1985.
Erlich (ed.), *PCR Technology*, Stockton Press, 1989.
Farrer, M. J. et al. A chromosome 4p haplotype segregating with Parkinson's disease and postural tremor. *Hum. Mol. Genet.* 8, 81–85 (1999).
Funayama M. et al. A new locus for Parkinson's disease (PARK8) maps to chromosome 12p11.2–q13.1. *Ann. Neurol.* 51, 296–301 (2002).
Gasser, T. et al. A susceptibility locus for Parkinson's disease maps to chromosome 2p13. *Nature. Genet.* 18, 262–265 (1998).
Gorman et al., Proc. Natl. Acad. Sci. USA 79:6777, 1982.
Ichinose, H. et al. Molecular cloning of the human NURR1 gene: characterization of the human gene and cDNA. *Gene.* 230, 233–239 (1999).
Iwawaki, T., Kohno, K., Kobayashi, K. Identification of a potential nurr1 response element that activates the tyrosine hydroxylase gene promoter in cultured cells. Biochem. Biophys. Res. Comm. 274, 590–595 (2000).
Kacian et al, Proc. Natl. Acad. Sci. USA 69:3038, 1972.
Kim et al., Gene 91:217, 1990.
Kitada, T. et al. Mutations in the parkin gene cause autosomal recessive juvenile parkinsonism. *Nature* 392, 605–608 (1998).
Langston, J. W. Epidemiology versus genetics in Parkinson's disease: progress in resolving an age-old debate. *Ann. Neurol.* Suppl, 1, S45–S52 (1998).
Law, S. W., Conneely, O. M., DeMayo, F. J., O'Malley, B. W. Identification of a new brain-specific transcription factor, nurr1. *Mol. Endocrinol.* 6, 2129–2135 (1992).
Le, W. D. et al. Selective agenesis of mesencephalic dopaminergic neurons in nurr1 deficient mice. *Exp. Neurol.* 159, 451–458 (1999a).
Le, W. D., Conneely, O. M., He, Y., Jankovic, J., Appel, S. H. Reduced nurr1 expression increases the vulnerability of mesencephalic dopamine neurons to MPTP-induced injure. *J. Neurochem.* 73, 2218–2221 (1999b).
Le, W. D., Dong, Z. J., He, Y., Conneely, O., Jankovic, J. Aged nurr1+/− mice develop behavioral and biochemical changes consistent with parkinsonism. *Parkinson. & Related Disord.* 7 (suppl), S39 (2001). Mages, H. W., Rilke, O., Bravo, R., Senger, G., Kroczek, R. A. NOT, a human immediate-early response gene closely related to the steroid/thyroid hormone receptor NAK1/TR3. *Mol. Endocrinol.* 8, 1583–1591 (1994).
Leroy, E. et al. The ubiquitin pathway in Parkinson's disease. *Nature.* 396, 451–452 (1998).

Maniatis et al., Science 236:1237, 1987.

Martin, E. D. et al. Association of single-nucleotide polymorphisms of the tau gene with late-onset Parkinson Disease. *J.A.M.A.* 286, 2239–2324 (2001).

Mizushima Lind S. Nagata, Nuc. Acids Res., 18:5322, 1990.

Nataraj, A. J., Olivos-Glander, I., Kurusawa, N., Highsmith, W. E. Jr. Single-strand conformation polymorphism and heteroduplex analysis for gel-based mutation detection. *Electrophores.* 20, 1177–1185 (1999).

Polymeropoulos, M. H. et al. Mutation in the α-synuclein gene identified in families with Parkinson's disease. *Science.* 276, 2045–2047 (1997).

Sacchetti, P., Mitchell, T. R., Grameman, J. G. Bannon, M. J. nurr1 enhances transcription of the human dopamine transporter gene through a novel mechanism. *J. Neurochem.* 76, 1565–1572 (2001).

Sambrook et al. *Molecular Cloning—A Laboratory Manual,* $2^{nd}$ ed., Cold Spring Harbor Laboratory Press, New York, 1989.

Saucedo-Cardenas, O. et al. nurr1 is essential for the induction of the dopaminergic phenotype and the survival of ventral mesencephalic late dopaminergic precursor neurons. *Proc. Natl. Acad. Sci. USA.* 95, 4013–4018 (1998).

Saucedo-Cardenas, O., Conneely, O. M. Comparative distribution of nurr1 and nur77 nuclear receptors in the mouse central nervous system. *J. Mol. Neurosci.* 7, 51–63 (1996).

Torii, T., Kawarai, S., Nakamura, H., Kawakami, H. Organization of the human orphan nuclear receptor NURR1 gene. *Gene.* 230, 225–232 (1999).

Uetsuki et al, J. Biol. Chem., 264:5791, 1989.

Valente E. M. et al. Localization of a novel locus for autosomal recessive early-onset parkinsonism, PARK6, on human chromosome 1p35–p36. *Am. J. Hum. Genet.* 68, 895–900 (2001).

Van Duijn C. M. et al, PARK7, a novel locus for autosomal recessive early-onset parkinsonism, on chromosome 1p36. *Am. J. Hum. Genet.* 69, 629–634 (2001).

Voss et al, Trends Biochem. Sci., 11:287, 1986.

Wu and R B. Wallace, Genomics 4:560, 1989.

Xu, P. Y., et al. Association of homozygous 7048G7049 variant in the intron six of NURR1 gene with Parkinson's disease. *Neurol.* 58, 881–884 (2002).

Zetterstrom R H, Williams R, Perlmann T, Olson L. Cellular expression of the immediate early transcription factors Nurr1 and NGFI-B suggests a gene regulatory role in several brain regions including the nigrostriatal dopamine system. Brain Res Mol Brain Res. 5 Sep. 1996; 41(1–2): 111–20.

Zetterström, R. H., Solomin, L., Jansson, L., Hoffer, B. J., Olson, L., Perlmann, T. Dopamine neuron agenesis in nurr1-deficient mice. *Science.* 276, 248–250 (1997).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention.

Accordingly, the appended claims are intended to include within their scope such processes, machines, manufacture, compositions of matter, means, methods, or steps.

What is claimed is:

1. A method of diagnosing Parkinson's disease in an individual comprising the steps of:
   obtaining a peripheral blood lymphocyte (PBL) sample from said individual; and
   assaying said sample for a decrease in NURR1 mRNA level, wherein said decrease indicates said individual has said Parkinson's disease and wherein the mRNA level is decreased relative to the mRNA level in a PBL normal control.

2. The method of claim 1, wherein said sample further comprises a decrease in tyrosine hydroxylase expression.

3. A method of identifying an individual at risk for Parkinson's disease comprising the steps of:
   obtaining a PBL sample from said individual; and
   assaying said sample for a decrease in NURR1 mRNA level, wherein said decrease indicates said individual is at risk for said Parkinson's disease and wherein the mRNA level is decreased relative to the mRNA level in a PBL normal control.

4. The method of claim 3, wherein said sample further comprises a decrease in tyrosine hydroxylase expression.

5. The method of claim 1, wherein said individual is further defined as having at least one symptom of Parkinson's disease.

6. The method of claim 1, wherein the Parkinson's disease is familial Parkinson's disease.

7. The method of claim 1, wherein the Parkinson's disease is sporadic Parkinson's disease.

8. The method of claim 1, wherein the assaying comprises polymerase chain reaction.

9. The method of claim 3, wherein said individual is further defined as having at least one symptom of Parkinson's disease.

10. The method of claim 3, wherein the Parkinson's disease is familial Parkinson's disease.

11. The method of claim 3, wherein the Parkinson's disease is sporadic Parkinson's disease.

12. The method of claim 3, wherein the assaying comprises polymerase chain reaction.

13. A method of diagnosing Parkinson's disease in an individual comprising assaying a sample from the individual for a decrease in NURR1 mRNA level, wherein said decrease indicates said individual has said Parkinson's disease and wherein the mRNA level is decreased relative to the mRNA level in a PBL normal control.

14. A method of identifying an individual at risk for Parkinson's disease comprising assaying a sample from an individual for a decrease in NURR1 mRNA level, wherein said decrease indicates said individual is at risk for said Parkinson's disease and wherein the mRNA level is decreased relative to the mRNA level in a PBL normal control.

* * * * *

SEQUENCE LISTING

```
<160> NUMBER OF SEQ ID NOS: 124

<210> SEQ ID NO 1
<211> LENGTH: 9824
<212> TYPE: DNA
<213> ORGANISM: Human
<220> FEATURE:
<221> NAME/KEY: misc_feature
<222> LOCATION: (1)..(9824)
<223> OTHER INFORMATION: n = unknown

<400> SEQUENCE: 1
gatcgattta ttcccttaaa actcgtggaa ggggtacgag ttggtgggca cagaggagta      60
tcgaaagtat tagagtttgc agaaggtggg aatcagagta cctttctgca gaaggcgcac     120
ctgttgcctg ctgctcggct gcattgtctg cgaaaggaaa agggcgacg cttcactctg     180 acttttgggg tttctaaaga gctgggtcac ggtcactgtc taccctctcc ccttcctctc     240
cccccccccc cgcaagcacc acgtcctcca tcgaacgtgg gcactgcatg gaaataagga     300
aacatagaaa aataagccct accccactc ccattccctt tcagatggga gtgtgggggg     360
tgggggtggg gtagagagag tgagagagag agataattag aatgaatata tgccagaaga    420
```

```
ggaggaggcc tgggacagga aaagggagta aaagggatg aaccgggtag ggaaatccca    480
cccgaactgc gtgagccctc tgagcgtctc gtgtcatggg acatctgtac gctcttccgc    540 taaggggtg acgaaggtgg gtgggagagg ttagggcgct gcaaggcaca tcccattccg    600
tgcggctcca ggtgcgtact acctggccca cgccggcctt gccttccgcc ggtgcttttg    660
ttgcaccctc cccacatgtg agcggccgag ccgctgcgcg ggcgcagggg cttcggggaa    720
agtgaagtgt cgcgacgctg cgggctgcgc agacctggga gaggtcacac ctctttcgga    780
aaaaaaaaaa gaaagaaaaa aaaacaccaa aaaccaccca agctggctac caaggtgaac    840
gcagagcggt tcccaccctta aaatcggccc tgctcgtgac gtcaggtcgg aaatatacca    900
aagcgagcgc gggccaggag tccagggagc gcggcagcgc ggcgattggg cggcgggccg    960
ctgacgcgcg ctgacgcgcg gagactttag gtgcatgttg cagcggcag cgcaagccac    1020 ataaacaaag gcacattggc ggccagggcc agtccgcccg gcggctcgcg cacggctccg    1080
cggtcccttt tgcctgtcca gccggccgcc tgtccctgct ccctccctcc gtgaggtgtc    1140
cgggttccct tcgcccagct ctcccacccc tacccgaccc cggcgccggg gctcccagag    1200
ggaactgcac ttcggcagag ttgaatgaat gaagagagac gcggagaact cctaagtgag    1260
tagatgcagc ccatgcagtt cgccttcttt tatgctttt ccttcttttg cacgtctctt    1320
ctttccactt gtgtgggaca ggttctctgg aagtgggagc cagaggcttc tagtgagagt    1380
gggaccgaag gatgggagt gcgtgcgcgc agttaccggg gggcatttgt tcgaactccg    1440
gctttggcac tagtggggag ttggctctcg acanaggttt ccaggctcct cattggtgga    1500
cgtggaaggg agactccacn gttttgggag ctgaggacta gcccgcggaa atgtgcgcaa    1560
agtttgctgt tagtgaggaa ntgattgtgg cctgtgaaca cggaaactcc aagtcctatg    1620
tatacgaggg aagctgccca caaactgaca gggagaggaa gttcttcagt ttatgcgttg    1680
cttgggaact gtgtctccgc ggctggccag cgcgcgatgt ttcccgggta ttgttgagta    1740
agggtggtgt tggtagcgtg tcctgttact aagttgcctg aaatttctgg ttttgacata    1800
tgctgtcctt gggtttgcga atgtatcaga gcgagaatat gaatatgtaa agagtacagt    1860
tatgaaactg tggagctacc aggggggttaa tatccaacac aggaatatct ctaagggctg    1920
tggggttcga gtctcctttc tgcttttttct gggtaatctt ccccccaccc ccaccaccac    1980
tatgaagcaa gattgtgggg gaggggaaag aataaaaaga gaggatactg gctttctttt    2040
ttcattagta ataagattgt ctgtgctcta gaatgtcttc caagtgggaa catctgaaaa    2100
ttactaggac acaagaatgc cttgttccag aaaggcagat tgtggaaggc attatgggga    2160
aggtgttcat cttgctgtgc tgggaaacac ttctaatatt ggtgccaata ccatataagc    2220
agtatgtccc ccctctgcaa ttgacctaag aagctcctgg naaagtagat cccctcttcc    2280
caccttgtga ccattaagcc ttgtgaccat taaagatgct gaaagacaag ttttctggaa    2340
aagtgaacat caatttatct gtagctccaa tcccagtgct ctgtcaaaag cactttagaa    2400
gtgcggatgc ttccactcaa gttgccttct cagtcaaggc ctttctaaca ttttgtaagg    2460
gggaagnttg ttttctcatt ttatattctt gacttntact ttcttcccct ctaccaaaag    2520
aaaaggcaat ttcaccacaa gaaaaaaaaa tgcaagaaa ggttccaatg ctgtatttttc    2580 atactctagt cttcatactc aggtcctgaa ttaacctaag atggaaatga cctctccacc    2640
tacactgtag caaaggggcc agttcattac atcataaatg ttaaatgagt tcatggacta    2700
gctttcctct tgcaggatnt tctctctgca aggatttaca cagtgcaatg ggtggtattt    2760
tctgttgttt caagtcattt nttttataca ttcattttaa gtgctatgtt tggtaaaggc    2820
```

```
ttcccactca tttccaatga dacaaacagg gaaggcatgg aagggcctgc ctggtgagtc    2880
tacatatgcc cagctgaatc tctgtcggga agaaaccctg aagcttcctg tgtctgtatt    2940
tcagggagga gattggacag gctggactcc ccattgcttt tctaaaaatc ttggaaactt    3000
tgtccttcat tgaattacga cactgtccac ctttaatttc ctcgaaaacg cctgtaactc    3060
ggctgaaggt tagtgcaact tcatttcttt cctttactct ccagagctcc caaacatca    3120
agaaacagga caaggcaaac cctgtaactt aaggtttgcc cgacccatcg ccttcgggaa    3180
caactttctc attgtgaaat tcaacttcat ttctagatgg tcatttctag aaagagactg    3240
ctgaatctga gcttcagaga agaggctcat ctgagtggga tgagtggggg ggtatgaggg    3300
agatgtttgg aaatacccag gagtgtagac cctcagtagc tttttagctc tgggtcttta    3360
tttggttagt cttttccacgc cctaaactgt tgttctgcag cattctctct ctcctgcctt    3420
tcctctcgcg cccctacatg ctctctgacn gccgcgggct gccggtgtag ctccaggtgt    3480
acccgagccc gggagaaagt gttcagttga cccaggctga gtgtgttatc accctgtttc    3540
atttccagcc atgccttgtg ttcaggcgca gtatgggtcc tcgcctcaag gagccagccc    3600
cgcttctcag agctacagtt accactcttc gggagaatac agctccgatt tcttaactcc    3660
agagtttgtc aagtttagca tggacctcac caacactgaa atcactgcca ccacttctct    3720
ccccagcttc agtaccttta tggacaacta cagcacaggc tacgacgtca agccaccttg    3780
cttgtaccaa atgcccctgt ccggacagca gtcctccatt aaggtagaag acattcagat    3840
gcacaactac cagcaacaca gccacctgcc cccccagtct gaggagatga tgccgcactc    3900
cgggtcggtt tactacaagc cctcctcgcc cccgacgccc accaccccgg gcttccaggt    3960
gcagcacagc cccatgtggg acgacccggg atctctccac aacttccacc agaactacgt    4020
ggccactacg cacatgatcg agcagaggaa aacgccagtc tcccgcctct ccctcttctc    4080
cttttaagcaa tcgcccccctg gcaccccggt gtctagttgc cagatgcgct tcgacgggcc    4140
cctgcacgtc cccatgaacc ggagcccgc cggcagccac cacgtggtgg acgggcagac    4200
cttcgctgtg cccaaccccca ttcgcaagcc cgcgtccatg ggcttcccgg gcctgcagat    4260
cggccacgcg tctcagctgc tcgacacgca ggtgccctca ccgccgtcgc ggggctcccc    4320
ctccaacgag gggctgtgcg ctgtgtgtgg ggacaacgcg gcctgccaac actacgcgt    4380
gcgcacctgt gagggctgca aaggcttctt taaggtgagc aaatggcggg gagcggagtt    4440
angcaggtag ggagcccnta ntgcccggga cctcggantg tgccctctgc cttggtgcca    4500
gtagcccagc cccagctctc ccgggactgc ccagctctcc ggggtccgcc gaagctgccc    4560
tgcaggagac catgggctgc ggcggggact tcccggggtgt ctgagaaagg gaagcagaaa    4620
gactgggagg cccagggtcg catccccccct cgcattcagc cgacccggct tggcccccccg    4680
cccgaagttg ctggagccgg agttggaaga gggtcatttg catgtgnata ggagctgtct    4740
tccctgttca agaatgaaat tggttaggac agagaaccgt gtctgagcta accaagtgga    4800
acagaattcc ctatggtcaa attaagtgat ctctttattt cgccatcctg attgaataat    4860
cttatcattt taaatagaga aggtctccaa ggaatgtaaa taatatgaat gcccacggat    4920
ttgtatttac tgagcgtctc cttctccttc tcttggcata taaaacacag caaggagcgg    4980
caaggttagc tcaaatgtta acgctatcaa ttttcttctg ttaaatgccc tggggagga    5040
aaaaagaaaa gaaagaaaga aaggaagag aaaaaaataa aatggaattg tgtgtatgtg    5100
tttgtttgtg gggaggaatc gtagaccca gtcacataac agaaatttc tccgagttgc    5160
```

```
ctgattttca aaagaanaaa aaaaatgttg gtctatattg tctccttttg cagcgcacag    5220
tgcaaaaaaa tgcaaaatac gtgtgtttag caaataaaaa ctgcccagtg acaagcgtc     5280 gccggaatcg ctgtcagtac tgccgatttc agaagtgcct ggctgttggg atggtcaaag    5340
aaggtaggct gagggagct gccgaccctc cagtttgcgc ctttaggaaa ccactgctca     5400
tactccagca tcacgttcca cttcccggtg ctgggatct ccgactcccc ctcagtatgg     5460
cctccaggac cctgcagctg cctgcttgcc cggccttccc tagagaaagc cgccaggccc    5520
ttctctcctt taactatacg acccatttgg aggaagacat aaaataaccc cgcatttttt    5580
aatgcttcta gtcagtgaag ctttacaag cantgggggc cntcagccgc tcagcntggt     5640
gccccgcggn tgcggccttc cccggggagg accgaggca gcagctgggc ctgggctcgg     5700
aaaagcggcg ctaacagggc tcttcctttg cagtggttcg cacagacagt ttaaaaggcc    5760
ggagaggtcg tttgccctcg aaaccgaaga gcccacagga gccctctccc ccttcgcccc    5820
cggtgagtct gatcagtgcc ctcgtcaggg cccatgtcga ctccaacccg gctatgacca    5880
gcctggacta ttccagggta agaagctggc gggggggata tcatgtggac aaaccgacag    5940
atgggcagga cccctcccca catccgtcat taactctcag attcaacggg ggtaaagaag    6000
gcaagcaagg ctgtatatgc ctcgcagctc tggccagggc ctcaagattc agatcttcag    6060
acaatccatg tagctggggg catagacatg aggacaggat ggaggaagga ggagagggac    6120
acnccacagg gttgaagct gtgtgaattc ccactacccc actaccccat cgcccctcct     6180
cttccatata caccagtgcc tctaccatga aatccagggg ctgtgcaaac tctcccccttt    6240 cccaatctac tttattccca gtcctccata gagatagatg ctttaatcct catccttcct    6300
ggcactgtgc tggggaagga tgtgggggcc tgtctggggg tcaggaagg gaaggagagg     6360 gtgtaaagaa tgccagtggg gtgggggatc aagtggtcag atcctttta ctccagctgt     6420 gaaaaatatg cgggctttaa ttggaggaag tatgttgagc aaacctggta gggactgcaa    6480
ttttattaag atttgcaaaa gggcgtctca gctcgaggcc cactctggga ctagcatgaa    6540
tactaacatg tcaattgttt tgtggagata agagtgaacg tttcccaggg ctggatggca    6600
ctgtatttag tctgtatgga aatgacaatt tacatattta aagcagcgac ctcgtagcac    6660
catccctaat tgaattaatt gccccggaac atctaatttc cttactggtc agagagaggt    6720
ttaattgtta taaaaacctg gctccccctat tagaaacggg gttagcaatt tcacgggtta    6780
tatattttag agancctcat taagtgcttt ttaaaatgaa attccagttc caggcgaacc    6840
ctgactatca aatgagtgga gatgacaccc agcatatcca gcaattctat gatctcctga    6900
ctggctccat ggagatcatc cggggctggg cagagaagat ccctggcttc gcagacctgc    6960
ccaaagccga ccaagacctg ctttttgaat cagctttctt agaactgttt gtccttcgat    7020
tagcatacag gtaataaggg agggaggaga cnatccangg aggctgtgag agaaatcnag    7080
aaaggaaaag aaagggagga agggaaacca tagggtgggg tagagaaaaa gacagaatag    7140
gaaatggaag tcggagaaag gaagaaaaag aaagaaaaca aaaaagacg agaagaagcg     7200 agcccagaag ccttggatga atggaatgga ggtgggatag ggggcgttct tgattgttat    7260
gaaattaaac cctttcaagg tccactggtc tacattttat taactcttca gtaattaggt    7320
gactcttaaa tccctcattt attgctcttc aagtaattag ttgtttagct tttctctctc    7380 tcttttttctc ccctctctct ctttggtatt aattgcaggt ccaacccagt ggagggtaaa    7440
ctcatctttt gcaatgggt ggtccttcac aggttgcaat gcgttcgtgg ctttggggaa     7500
tggattgatt ccattgttga attctcctcc aacttgcaga atatgaacat cgacatttct    7560
```

-continued

```
gccttctcct gcattgctgc cctggctatg gtcacaggtc agtactgcag gcgcagggcg      7620
cttcccctcc agaactgcct agcaggattt gtcctgagtt tcccttgtca cagattctcc      7680
ttggttttgc caactagcta actgtcttgt acattcttct tttgtttctg attatgtttt      7740
ctgcagagag acacgggctc aaggaaccca agagagtgga agaactgcaa aacaagattg      7800
taaattgtct caaagaccac gtgactttca caatgggggg gttgaaccgc cccaattatt      7860
tgtccaaact gttggggaag ctcccagaac ttcgtaccct ttgcacacag gggctacagc      7920
gcattttcta cctgaaattg gaagacttgg tgccaccgcc agcaataatt gacaaacttt      7980
tcctggacac tttacctttc taagacctcc tcccaagcac ttcaaaggaa ctggaatgat      8040
aatggaaact gtcaagaggg ggcaagtcac atgggcagag atagccgtgt gagcagtctc      8100
agctcaagct gcccccccatt tctgtaaccc tcctagcccc cttgatccct aaagaaaaca      8160
aacaaacaaa caaaaactgt tgctatttcc taacctgcag gcagaacctg aaagggcatt      8220
ttggctccgg ggcatcctgg atttagaaca tggactacac acaatacagt ggtataaact      8280
ttttattctc agtttaaaaa tcagtttgtt gttcagaaga aagattgcta taaggtataa      8340
tgggaaatgt ttggccatgc ttggttgttg cagttcagac aaatgtaaca cacacacaca      8400
tacacacaca cacacacaca gagacacatc ttaaggggac ccacaagtat tgcccttttaa     8460 caagacttca aagttttctg ctgtaaagaa agctgtaata tatagtaaaa ctaaatgttg      8520
cgtgggtggc atgagttgaa gaaggcaaag gcttgtaaat ttacccaatg cagtttggct      8580
ttttaaatta ttttgtgcct atttatgaat aaatattaca aattctaaaa gataagtgtg      8640
tttgcaaaaa aaagaaaat aaatacataa aaagggaca agcatgttga ttctaggttg       8700
aaaatgttat aggcacttgc tacttcagta atgtctatat tatataaata gtatttcaga      8760
cactatgtag tctgttagat tttataaaga ttggtagtta tctgagctta aacatttttct     8820 caattgtaaa ataggtgggc acaagtatta cacatcagaa atcctgaca aaagggacac       8880 atagtgtttg taacaccgtc caacattcct tgtttgtaag tgttgtatgt accgttgatg      8940
ttgataaaaa gaaagtttat atcttgatta ttttgttgtc taaagctaaa caaaacttgc      9000
atgcagcagc ttttgactgt ttccagagtg cttataatat acataactcc ctggaaataa     9060
ctgagcactt tgaattttttt ttatgtctaa aattgtcagt taatttatta ttttgtttga     9120
gtaagaattt taatattgcc atattctgta gtatttttct ttgtatattt ctagtatggc      9180
acatgatatg agtcactgcc ttttttttcta tggtgtatga cagttagaga tgctgatttt     9240
ttttctgata aattctttct ttgagaaaga caatttaat gtttacaaca ataaaccatg       9300
taaatgaaca gaattttgtc ttcttttttgg gtcagaaaaa ataatgacta aacagcaaca     9360
taacatacac agttggagat taatttggga taggtcactt attcaatatc tgaattttaa      9420
acagcctaaa tctattctgg caaaagaaat caggtgaacc agaataatta tccagataat      9480
tcagtaaaat atttttttcctt aaccagaatt ttccagtctg gtgaccaata tttattagga    9540
tcaatttaga atatctcaat tcttctgtta acttttgcaag taagtgtagc tttcaggaga     9600
gaagttctgg agacccaaaa gcttttgaac ttgagcaagg tcagagtcta gtcaagtact      9660
tgtcttgcac agtgattagg aagtatcttt ttaagactca agaagtcaac atggatttga     9720
ggagtgttgt atgtaatctc cgattttcca atttctcaat ttacaactgt tgggtcatgg      9780
agaaagggca agcagttca ggcccttttgg gccttgggtc actt                       9824
```

<210> SEQ ID NO 2

<211> LENGTH: 598
<212> TYPE: PRT
<213> ORGANISM: Human

<400> SEQUENCE: 2

```
Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
        35                  40                  45

Thr Glu Ile Thr Ala Thr Thr Ser Leu Pro Ser Phe Ser Thr Phe Met
    50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125

Thr Pro Thr Thr Pro Gly Phe Gln Val Gln His Ser Pro Met Trp Asp
    130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
        195                 200                 205

Ser His His Val Val Asp Gly Gln Thr Phe Ala Val Pro Asn Pro Ile
    210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Ser Arg Gly Ser
                245                 250                 255

Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
        275                 280                 285

Arg Thr Val Gln Lys Asn Ala Lys Tyr Val Cys Leu Ala Asn Lys Asn
    290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
                325                 330                 335

Ser Leu Lys Gly Arg Arg Gly Arg Leu Pro Ser Lys Pro Lys Ser Pro
            340                 345                 350

Gln Glu Pro Ser Pro Pro Ser Pro Val Ser Leu Ile Ser Ala Leu
        355                 360                 365

Val Arg Ala His Val Asp Ser Asn Pro Ala Met Thr Ser Leu Asp Tyr
    370                 375                 380

Ser Arg Phe Gln Ala Asn Pro Asp Tyr Gln Met Ser Gly Asp Asp Thr
```

-continued

```
                385                 390                 395                 400
Gln His Ile Gln Gln Phe Tyr Asp Leu Leu Thr Gly Ser Met Glu Ile
                    405                 410                 415
Ile Arg Gly Trp Ala Glu Lys Ile Pro Gly Phe Ala Asp Leu Pro Lys
                420                 425                 430
Ala Asp Gln Asp Leu Leu Phe Glu Ser Ala Phe Leu Glu Leu Phe Val
            435                 440                 445
Leu Arg Leu Ala Tyr Arg Ser Asn Pro Val Glu Gly Lys Leu Ile Phe
        450                 455                 460
Cys Asn Gly Val Val Leu His Arg Leu Gln Cys Val Arg Gly Phe Gly
465                 470                 475                 480
Glu Trp Ile Asp Ser Ile Val Glu Phe Ser Ser Asn Leu Gln Asn Met
                485                 490                 495
Asn Ile Asp Ile Ser Ala Phe Ser Cys Ile Ala Ala Leu Ala Met Val
                500                 505                 510
Thr Glu Arg His Gly Leu Lys Glu Pro Lys Arg Val Glu Glu Leu Gln
            515                 520                 525
Asn Lys Ile Val Asn Cys Leu Lys Asp His Val Thr Phe Asn Asn Gly
        530                 535                 540
Gly Leu Asn Arg Pro Asn Tyr Leu Ser Lys Leu Leu Gly Lys Leu Pro
545                 550                 555                 560
Glu Leu Arg Thr Leu Cys Thr Gln Gly Leu Gln Arg Ile Phe Tyr Leu
                565                 570                 575
Lys Leu Glu Asp Leu Val Pro Pro Ala Ile Ile Asp Lys Leu Phe
            580                 585                 590
Leu Asp Thr Leu Pro Phe
        595

<210> SEQ ID NO 3
<211> LENGTH: 21
<212> TYPE: DNA
<213> ORGANISM: Human

<400> SEQUENCE: 3
aaatcccacc cgaactgcgt g                                            21

<210> SEQ ID NO 4
<211> LENGTH: 21
<212> TYPE: DNA
<213> ORGANISM: Human

<400> SEQUENCE: 4
gacacttcac tttccccgaa g                                            21

<210> SEQ ID NO 5
<211> LENGTH: 19
<212> TYPE: DNA
<213> ORGANISM: human

<400> SEQUENCE: 5
gcaagccaca taaacaagg                                               19

<210> SEQ ID NO 6
<211> LENGTH: 21
<212> TYPE: DNA
<213> ORGANISM: human

<400> SEQUENCE: 6
```

```
actgcatggg ctgcatctac t                              21
```

<210> SEQ ID NO 7
<211> LENGTH: 21
<212> TYPE: DNA
<213> ORGANISM: Human

<400> SEQUENCE: 7

```
gcttcctgtg tctgtatttc a                              21
```

<210> SEQ ID NO 8
<211> LENGTH: 21
<212> TYPE: DNA
<213> ORGANISM: Human

<400> SEQUENCE: 8

```
ctaccttcag ccgagttaca g                              21
```

<210> SEQ ID NO 9
<211> LENGTH: 21
<212> TYPE: DNA
<213> ORGANISM: human

<400> SEQUENCE: 9

```
acccaggctg agtgtgttat c                              21
```

<210> SEQ ID NO 10
<211> LENGTH: 21
<212> TYPE: DNA
<213> ORGANISM: human

<400> SEQUENCE: 10

```
tgcttccctt tctcagacac c                              21
```

<210> SEQ ID NO 11
<211> LENGTH: 21
<212> TYPE: DNA
<213> ORGANISM: human

<400> SEQUENCE: 11

```
cgtagacccc agtcacataa c                              21
```

<210> SEQ ID NO 12
<211> LENGTH: 21
<212> TYPE: DNA
<213> ORGANISM: Human

<400> SEQUENCE: 12

```
tgtcttcctc caaatgggtc g                              21
```

<210> SEQ ID NO 13
<211> LENGTH: 21
<212> TYPE: DNA
<213> ORGANISM: Human

<400> SEQUENCE: 13

```
atgcttctag tcagtgaagg c                              21
```

<210> SEQ ID NO 14
<211> LENGTH: 21
<212> TYPE: DNA
<213> ORGANISM: Human

<400> SEQUENCE: 14

-continued ccagcttctt accctggaat a                                    21

<210> SEQ ID NO 15
<211> LENGTH: 21
<212> TYPE: DNA
<213> ORGANISM: Human

<400> SEQUENCE: 15
ttccagttcc aggcgaaccc t                                    21

<210> SEQ ID NO 16
<211> LENGTH: 22
<212> TYPE: DNA
<213> ORGANISM: Human

<400> SEQUENCE: 16
gtctcctccc tcccttatta cc                                   22

<210> SEQ ID NO 17
<211> LENGTH: 20
<212> TYPE: DNA
<213> ORGANISM: Human

<400> SEQUENCE: 17
attgcaggtc caacccagtg                                      20

<210> SEQ ID NO 18
<211> LENGTH: 20
<212> TYPE: DNA
<213> ORGANISM: Human

<400> SEQUENCE: 18
gcagtactga cctgtgacca                                      20

<210> SEQ ID NO 19
<211> LENGTH: 20
<212> TYPE: DNA
<213> ORGANISM: Human

<400> SEQUENCE: 19
gtcaccagac tggaaaattc                                      20

<210> SEQ ID NO 20
<211> LENGTH: 20
<212> TYPE: DNA
<213> ORGANISM: Human

<400> SEQUENCE: 20
taacaccgtc caacattcct                                      20

<210> SEQ ID NO 21
<211> LENGTH: 21
<212> TYPE: DNA
<213> ORGANISM: Human

<400> SEQUENCE: 21
gggatatcat gtggacaaac c                                    21

<210> SEQ ID NO 22
<211> LENGTH: 21
<212> TYPE: DNA
<213> ORGANISM: Human

```
<400> SEQUENCE: 22
gaagcatggg aaacgtgtgt c                                          21

<210> SEQ ID NO 23
<211> LENGTH: 40
<212> TYPE: DNA
<213> ORGANISM: Human

<400> SEQUENCE: 23
ggctccgcgg tcccttgcc tttgcctgtc cagccggccg                       40

<210> SEQ ID NO 24
<211> LENGTH: 34
<212> TYPE: DNA
<213> ORGANISM: Human

<400> SEQUENCE: 24
cggccggctg gacaggcaaa gggaccgcgg agcc                            34

<210> SEQ ID NO 25
<211> LENGTH: 36
<212> TYPE: DNA
<213> ORGANISM: Human

<400> SEQUENCE: 25
gctccctccc tccgtgaggg gtccgggttc cctttc                          36

<210> SEQ ID NO 26
<211> LENGTH: 35
<212> TYPE: DNA
<213> ORGANISM: Human

<400> SEQUENCE: 26
gaagggaacc cggaccctc acggagggag ggagc                            35

<210> SEQ ID NO 27
<211> LENGTH: 25
<212> TYPE: DNA
<213> ORGANISM: Human

<400> SEQUENCE: 27
ggatttggtc gtattgggcg cctgg                                      25

<210> SEQ ID NO 28
<211> LENGTH: 25
<212> TYPE: DNA
<213> ORGANISM: Human

<400> SEQUENCE: 28
ccctgcaaat gagccccagc cttct                                      25

<210> SEQ ID NO 29
<211> LENGTH: 23
<212> TYPE: DNA
<213> ORGANISM: Human

<400> SEQUENCE: 29
gcagagaaga tccctggctt cgc                                        23

<210> SEQ ID NO 30
<211> LENGTH: 23
<212> TYPE: DNA
<213> ORGANISM: Human
```

```
<400> SEQUENCE: 30
cgcattgcaa cctgtgcaag acc                                              23

<210> SEQ ID NO 31
<211> LENGTH: 18
<212> TYPE: DNA
<213> ORGANISM: Human

<400> SEQUENCE: 31
cggtcccttt tgcctgtc                                                    18

<210> SEQ ID NO 32
<211> LENGTH: 17
<212> TYPE: DNA
<213> ORGANISM: Human

<400> SEQUENCE: 32
cggtcccttt gcctgtc                                                     17

<210> SEQ ID NO 33
<211> LENGTH: 19
<212> TYPE: DNA
<213> ORGANISM: Human

<400> SEQUENCE: 33
gaggtgtccg ggttccctt                                                   19

<210> SEQ ID NO 34
<211> LENGTH: 19
<212> TYPE: DNA
<213> ORGANISM: Human

<400> SEQUENCE: 34
gaggggtccg ggttccctt                                                   19

<210> SEQ ID NO 35
<211> LENGTH: 112
<212> TYPE: DNA
<213> ORGANISM: Human

<400> SEQUENCE: 35 tctcccttc gccccggtg agtctgatca gtgccctcgt cagggcccat gtcgactcca        60
acccggctat gaccagcctg gactattcca ggttccaggc gaaccctgac ta             112

<210> SEQ ID NO 36
<211> LENGTH: 112
<212> TYPE: DNA
<213> ORGANISM: Human
<220> FEATURE:
<221> NAME/KEY: misc_feature
<222> LOCATION: (1)..(112)
<223> OTHER INFORMATION: n = deleted nucleotide

<400> SEQUENCE: 36 tctcccttc gccccgnnn nnnnnnnnn nnnnnnnnn nnnnnnnnn nnnnnnnnn            60 nnnnnnnnnn nnnnnnnnnn nnnnnnnnnn nnttccaggc gaaccctgac ta            112

<210> SEQ ID NO 37
<211> LENGTH: 24
<212> TYPE: DNA
<213> ORGANISM: Human
```

```
<400> SEQUENCE: 37
gagctacagt taccactctt cggg                                              24

<210> SEQ ID NO 38
<211> LENGTH: 20
<212> TYPE: DNA
<213> ORGANISM: Human

<400> SEQUENCE: 38
ggtggacagt gtcgtaattc                                                   20

<210> SEQ ID NO 39
<211> LENGTH: 22
<212> TYPE: DNA
<213> ORGANISM: Human

<400> SEQUENCE: 39
ggaactgcac ttcggcagag tt                                                22

<210> SEQ ID NO 40
<211> LENGTH: 24
<212> TYPE: DNA
<213> ORGANISM: Human

<400> SEQUENCE: 40
gtttgccctc gaaaccgaa gagc                                               24

<210> SEQ ID NO 41
<211> LENGTH: 24
<212> TYPE: DNA
<213> ORGANISM: Human

<400> SEQUENCE: 41
gcattgcaac ctgtgcaaga ccac                                              24

<210> SEQ ID NO 42
<211> LENGTH: 23
<212> TYPE: DNA
<213> ORGANISM: Human

<400> SEQUENCE: 42
cgcattgcaa cctgtgcaag acc                                               23

<210> SEQ ID NO 43
<211> LENGTH: 9824
<212> TYPE: DNA
<213> ORGANISM: Human
<220> FEATURE:
<221> NAME/KEY: misc_feature
<222> LOCATION: (1)..(9824)
<223> OTHER INFORMATION: n = unknown

<400> SEQUENCE: 43
gatcgattta ttcccttaaa actcgtggaa ggggtacgag ttggtgggca cagaggagta       60
tcgaaagtat tagagtttgc agaaggtggg aatcagagta cctttctgca gaaggcgcac      120
ctgttgcctg ctgctcggct gcattgtctg cgaaaggaaa aggggcgacg cttcactctg      180
acttttgggg tttctaaaga gctgggtcac ggtcactgtc taccctctcc ccttcctctc      240
cccccccccc cgcaagcacc acgtcctcca tcgaacgtgg gcactgcatg gaaataagga      300
aacatagaaa aataagccct accccccactc ccattccctt tcagatggga gtgtgggggg      360
tgggggtggg gtagagagag tgagagagag agataattag aatgaatata tgccagaaga      420
```

-continued

```
ggaggaggcc tgggacagga aaagggagta aaaggggatg aaccgggtag ggaaatccca    480
cccgaactgc gtgagccctc tgagcgtctc gtgtcatggg acatctgtac gctcttccgc    540
taagggggtg acgaaggtgg gtgggagagg ttagggcgct gcaaggcaca tcccattccg    600
tgcggctcca ggtgcgtact acctggccca cgccggcctt gccttccgcc ggtgcttttg    660
ttgcaccctc cccacatgtg agcggccgag ccgctgcgcg ggcgcagggg cttcggggaa    720
agtgaagtgt cgcgacgctg cgggctgcgc agacctggga gaggtcacac ctctttcgga    780
aaaaaaaaaa gaaagaaaaa aaacaccaa aaccaccca agctggctac caaggtgaac    840
gcagagcggt tcccacctta aaatcggccc tgctcgtgac gtcaggtcgg aaatatacca    900
aagcgagcgc gggccaggag tccagggagc gcggcagcgc ggcgattggg cggcgggccg    960
ctgacgcgcg ctgacgcgcg gagactttag gtgcatgttg gcagcggcag cgcaagccac   1020
ataaacaaag gcacattggc ggccagggcc agtccgcccg gcggctcgcg cacggctccg   1080
cggtcccttt tgcctgtcca gccggccgcc tgtccctgct ccctccctcc gtgaggtgtc   1140
cgggttccct tcgcccagct ctcccacccc tacccgaccc cggcgccggg gctcccagag   1200
ggaactgcac ttcggcagag ttgaatgaat gaagagagac gcggagaact cctaagtgag   1260
tagatgcagc ccatgcagtt cgccttcttt tatgcttttt ccttcttttg cacgtctctt   1320
cttttccactt gtgtgggaca ggttctctgg aagtgggagc cagaggcttc tagtgagagt   1380
gggaccgaag gatggggagt gcgtgcgcgc agttaccggg gggcatttgt tcgaactccg   1440
gctttggcac tagtggggag ttggctctcg acanaggttt ccaggctcct cattggtgga   1500
cgtggaaggg agactccacn gttttgggag ctgaggacta gccgcggaa atgtgcgcaa   1560
agtttgctgt tagtgaggaa ntgattgtgg cctgtgaaca cggaaactcc aagtcctatg   1620
tatacgaggg aagctgccca caaactgaca gggagaggaa gttcttcagt ttatgcgttg   1680
cttgggaact gtgtctccgc ggctggccag cgcgcgatgt ttcccgggta ttgttgagta   1740
agggtggtgt tggtagcgtg tcctgttact aagttgcctg aaatttctgg ttttgacata   1800
tgctgtcctt gggtttgcga atgtatcaga gcgagaatat gaatatgtaa agagtacagt   1860
tatgaaactg tggagctacc aggggggttaa tatccaacac aggaatatct ctaagggctg   1920
tggggttcga gtctcctttc tgcttttttct gggtaatctt ccccccaccc ccaccaccac   1980
tatgaagcaa gattgtgggg gagggaaag aataaaaaga gaggatactg ctttctttt   2040
ttcattagta ataagattgt ctgtgctcta aatgtcttc caagtgggaa catctgaaaa   2100
ttactaggac acaagaatgc cttgttccag aaaggcagat tgtggaaggc attatgggga   2160
aggtgttcat cttgctgtgc tgggaaacac ttctaatatt ggtgccaata ccatataagc   2220
agtatgtccc ccctctgcaa ttgacctaag aagctcctgg naaagtagat cccctcttcc   2280
caccttgtga ccattaagcc ttgtgaccat taaagatgct gaaagacaag ttttctggaa   2340
aagtgaacat caatttatct gtagctccaa tcccagtgct ctgtcaaaag cactttagaa   2400
gtgcggatgc ttccactcaa gttgccttct cagtcaaggc cttttctaaca tttttgtaagg   2460
gggaagnttg ttttctcatt ttatattctt gacttntact ttcttcccct ctaccaaaag   2520
aaaaggcaat ttcaccacaa gaaaaaaaa tgcaagagaa ggttccaatg ctgtattttc   2580
atactctagt cttcatactc aggtcctgaa ttaacctaag atggaaatga cctctccacc   2640
tacactgtag caaaggggcc agttcattac atcataaatg ttaaatgagt tcatggacta   2700
gctttcctct tgcaggatnt tctctctgca aggatttaca cagtgcaatg ggtggtattt   2760
```

| | |
|---|---|
| tctgttgttt caagtcattt nttttataca ttcattttaa gtgctatgtt tggtaaaggc | 2820 |
| ttcccactca tttccaatga gacaaacagg gaaggcatgg aagggcctgc ctggtgagtc | 2880 |
| tacatatgcc cagctgaatc tctgtcggga agaaaccctg aagcttcctg tgtctgtatt | 2940 |
| tcaggagga gattggacag gctggactcc ccattgcttt tctaaaaatc ttggaaactt | 3000 |
| tgtccttcat tgaattacga cactgtccac ctttaatttc ctcgaaaacg cctgtaactc | 3060 |
| ggctgaaggt tagtgcaact tcatttcttt cctttactct ccagagctcc ccaaacatca | 3120 |
| agaaacagga caaggcaaac cctgtaactt aaggtttgcc cgacccatcg ccttcgggaa | 3180 |
| caactttctc attgtgaaat tcaacttcat ttctagatgg tcatttctag aaagagactg | 3240 |
| ctgaatctga gcttcagaga agaggctcat ctgagtggga tgagtggggg ggtatgaggg | 3300 |
| agatgtttgg aaatacccag gagtgtagac cctcagtagc ttttttagctc tgggtcttta | 3360 |
| tttggttagt cttttccacgc cctaaactgt tgttctgcag cattctctct ctcctgcctt | 3420 |
| tcctctcgcg cccctacatg ctctctgacn gccgcgggct gccggtgtag ctccaggtgt | 3480 |
| acccgagccc gggagaaagt gttcagttga cccaggctga gtgtgttatc accctgtttc | 3540 |
| atttccagcc atgccttgtg ttcaggcgca gtatgggtcc tcgcctcaag gagccagccc | 3600 |
| cgcttctcag agctacagtt accactcttc gggagaatac agctccgatt tcttaactcc | 3660 |
| agagtttgtc aagtttagca tggacctcac caacactgaa atcactgcca ccacttctct | 3720 |
| ccccagcttc agtacccttta tggacaacta cagcacaggc tacgacgtca agccaccttg | 3780 |
| cttgtaccaa atgcccctgt ccggacagca gtcctccatt aaggtagaag acattcagat | 3840 |
| gcacaactac cagcaacaca gccacctgcc ccccagtct gaggagatga tgccgcactc | 3900 |
| cgggtcggtt tactacaagc cctcctcgcc cccgacgccc accaccccgg gcttccaggt | 3960 |
| gcagcacagc cccatgtggg acgacccggg atctctccac aacttccacc agaactacgt | 4020 |
| ggccactacg cacatgatcg agcagaggaa aacgccagtc tcccgcctct ccctcttctc | 4080 |
| ctttaagcaa tcgcccccctg gcaccccggt gtctagttgc cagatgcgct tcgacgggcc | 4140 |
| cctgcacgtc cccatgaacc cggagcccgc cggcagccac cacgtggtgg acgggcagac | 4200 |
| cttcgctgtg cccaaccca ttcgcaagcc cgcgtccatg ggcttcccgg gcctgcagat | 4260 |
| cggccacgcg tctcagctgc tcgacacgca ggtgccctca ccgccgtcgc ggggctcccc | 4320 |
| ctccaacgag gggctgtgcg ctgtgtgtgg ggacaacgcg gcctgccaac actacggcgt | 4380 |
| gcgcacctgt gagggctgca aaggcttctt taaggtgagc aaatggcggg gagcggagtt | 4440 |
| angcaggtag ggagcccnta ntgcccggga cctcggantg tgccctctgc cttggtgcca | 4500 |
| gtagcccagc cccagctctc ccgggactgc ccagctctcc ggggtccgcc gaagctgccc | 4560 |
| tgcaggagac catgggctgc ggcggggact tcccgggtgt ctgagaaagg gaagcagaaa | 4620 |
| gactgggagg cccagggtcg catcccccct cgcattcagc cgacccggct tggcccccg | 4680 |
| cccgaagttg ctggagccgg agttggaaga gggtcatttg catgtgnata ggagctgtct | 4740 |
| tccctgttca agaatgaaat tggttaggac agagaaccgt gtctgagcta accaagtgga | 4800 |
| acagaattcc ctatggtcaa attaagtgat ctctttattt cgccatcctg attgaataat | 4860 |
| cttatcattt taaatagaga aggtctccaa ggaatgtaaa taatatgaat gcccacggat | 4920 |
| ttgtatttac tgagcgtctc cttctccttc tcttggcata taaacacag caaggagcgg | 4980 |
| caaggttagc tcaaatgtta acgctatcaa ttttcttctg ttaaatgccc tggggagga | 5040 |
| aaaaagaaaa gaaagaaaga aaggaagag aaaaaaataa aatggaattg tgtgtatgtg | 5100 |
| tttgtttgtg gggaggaatc gtagaccccca gtcacataac agaaattttc tccgagttgc | 5160 |

```
ctgattttca aaagaanaaa aaaatgttg gtctatattg tctccttttg cagcgcacag    5220
tgcaaaaaaa tgcaaaatac gtgtgtttag caaataaaaa ctgcccagtg acaagcgtc    5280 gccggaatcg ctgtcagtac tgccgatttc agaagtgcct ggctgttggg atggtcaaag    5340
aaggtaggct gagggagct gccgaccctc cagtttgcgc ctttaggaaa ccactgctca    5400
tactccagca tcacgttcca cttcccggtg ctggggatct ccgactcccc ctcagtatgg    5460
cctccaggac cctgcagctg cctgcttgcc cggccttccc tagagaaagc cgccaggccc    5520
ttctctcctt taactatacg acccatttgg aggaagacat aaaataaccc cgcattttt    5580 aatgcttcta gtcagtgaag ctttacaag cantggggc cntcagccgc tcagcntggt     5640
gccccgcggn tgcggccttc ccggggagg accgaggca gcagctgggc ctgggctcgg     5700
aaaagcggcg ctaacagggc tcttcctttg cagtggttcg cacagacagt ttaaaaggcc    5760
ggagaggtcg tttgccctcg aaaccgaaga gcccacagga gccctctccc ccttcgcccc    5820
cggtgagtct gatcagtgcc ctcgtcaggg cccatgtcga ctccaacccg gctatgacca    5880
gcctggacta ttccagggta agaagctggg gggggggata tcatgtggac aaaccgacag    5940
atgggcagga cccctcccca catccgtcat taactctcag attcaacggg ggtaaagaag    6000
gcaagcaagg ctgtatatgc ctcgcagctc tggccagggc ctcaagattc agatcttcag    6060
acaatccatg tagctggggg catagacatg aggacaggat ggaggaagga ggagagggac    6120
acnccacagg gtttgaagct gtgtgaattc ccactacccc actacccat cgcccctcct     6180 cttccatata caccagtgcc tctaccatga aatccagggg ctgtgcaaac tctcccccctt    6240 cccaatctac tttattccca gtcctccata gagatagatg ctttaatcct catccttcct    6300
ggcactgtgc tggggaagga tgtgggggcc tgtctggggg tcaggaagg gaaggagagg     6360 gtgtaaagaa tgccagtggg gtgggggatc aagtggtcag atccttttta ctccagctgt    6420
gaaaaatatg cgggctttaa ttggaggaag tatgttgagc aaacctggta gggactgcaa    6480
ttttattaag atttgcaaaa gggcgtctca gctcgaggcc cactctggga ctagcatgaa    6540
tactaacatg tcaattgttt tgtggagata agagtgaacg tttcccaggg ctggatggca    6600
ctgtatttag tctgtatgga aatgacaatt tacatattta aagcagcgac ctcgtagcac    6660
catccctaat tgaattaatt gccccggaac atctaatttc cttactggtc agagagaggt    6720
ttaattgtta taaaaacctg gctcccctat tagaaacggg gttagcaatt tcacgggtta    6780
tatattttag agancctcat taagtgcttt ttaaaatgaa attccagttc caggcgaacc    6840
ctgactatca aatgagtgga gatgacaccc agcatatcca gcaattctat gatctcctga    6900
ctggctccat ggagatcatc cggggctggg cagagaagat ccctggcttc gcagacctgc    6960
ccaaagccga ccaagacctg ctttttgaat cagctttctt agaactgttt gtccttcgat    7020
tagcatacag gtaataaggg agggaggaga cnatccangg aggctgtgag agaaatcnag    7080
aaaggaaaag aaagggagga agggaaacca tagggtgggg tagagaaaaa gacagaatag    7140
gaaatggaag tcggagaaag gaagaaaaag aaagaaaaca aaaaaagacg agaagaagcg    7200
agcccagaag ccttggatga atggaatgga ggtgggatag gggcgttct tgattgttat     7260 gaaattaaac ccttttcaagg tccactggtc tacattttat taactcttca gtaattaggt    7320
gactcttaaa tccctcattt attgctcttc aagtaattag ttgtttagct tttctctctc    7380 tcttttctc ccctctctct ctttggtatt aattgcaggt ccaacccagt ggagggtaaa    7440
ctcatctttt gcaatggggt ggtcttgcac aggttgcaat gcgttcgtgg ctttggggaa    7500
```

```
tggattgatt ccattgttga attctcctcc aacttgcaga atatgaacat cgacatttct    7560
gccttctcct gcattgctgc cctggctatg gtcacaggtc agtactgcag gcgcagggcg    7620
cttcccctcc agaactgcct agcaggattt gtcctgagtt tcccttgtca cagattctcc    7680
ttggttttgc caactagcta actgtcttgt acattcttct tttgtttctg attatgtttt    7740
ctgcagagag acacgggctc aaggaaccca agagagtgga agaactgcaa aacaagattg    7800
taaattgtct caaagaccac gtgactttca acaatggggg gttgaaccgc cccaattatt    7860
tgtccaaact gttggggaag ctcccagaac ttcgtaccct ttgcacacag gggctacagc    7920
gcattttcta cctgaaattg gaagacttgg tgccaccgcc agcaataatt gacaaacttt    7980
tcctggacac tttacctttc taagacctcc tcccaagcac ttcaaaggaa ctggaatgat    8040
aatgaaaact gtcaagaggg ggcaagtcac atgggcagag atagccgtgt gagcagtctc    8100
agctcaagct gccccccatt tctgtaaccc tcctagcccc cttgatccct aaagaaaaca    8160
aacaaacaaa caaaaactgt tgctatttcc taacctgcag gcagaacctg aaagggcatt    8220
ttggctccgg ggcatcctgg atttagaaca tggactacac acaatacagt ggtataaact    8280
ttttattctc agtttaaaaa tcagtttgtt gttcagaaga aagattgcta taaggtataa    8340
tgggaaatgt ttggccatgc ttggttgttg cagttcagac aaatgtaaca cacacaca     8400 tacacacaca cacacacaca gagacacatc ttaaggggac ccacaagtat tgccctttaa    8460
caagacttca aagttttctg ctgtaaagaa agctgtaata tatagtaaaa ctaaatgttg    8520
cgtgggtggc atgagttgaa gaaggcaaag gcttgtaaat ttacccaatg cagtttggct    8580
ttttaaatta ttttgtgcct atttatgaat aaatattaca aattctaaaa gataagtgtg    8640
tttgcaaaaa aaagaaaat aaatacataa aaaagggaca agcatgttga ttctaggttg     8700
aaaatgttat aggcacttgc tacttcagta atgtctatat tatataaata gtatttcaga    8760
cactatgtag tctgttagat tttataaaga ttggtagtta tctgagctta aacattttct    8820
caattgtaaa ataggtgggc acaagtatta cacatcagaa aatcctgaca aaagggacac    8880
atagtgtttg taacaccgtc caacattcct tgtttgtaag tgttgtatgt accgttgatg    8940
ttgataaaaa gaaagtttat atcttgatta tttttgttgtc taaagctaaa caaaacttgc   9000
atgcagcagc ttttgactgt ttccagagtg cttataatat acataactcc ctggaaataa    9060
ctgagcactt tgaattttt ttatgtctaa aattgtcagt taatttatta ttttgtttga     9120
gtaagaattt taatattgcc atattctgta gtattttct ttgtatattt ctagtatggc     9180
acatgatatg agtcactgcc ttttttcta tggtgtatga cagttagaga tgctgatttt     9240
ttttctgata aattctttct ttgagaaaga caattttaat gtttacaaca ataaaccatg    9300
taaatgaaca gaattttgtc ttcttttgg gtcagaaaaa ataatgacta aacagcaaca     9360
taacatacac agttggagat taatttggga taggtcactt attcaatatc tgaattttaa    9420
acagcctaaa tctattctgg caaaagaaat caggtgaacc agaataatta tccagataat    9480
tcagtaaaat attttttctt aaccagaatt ttccagtctg gtgaccaata tttattagga    9540
tcaatttaga atatctcaat tcttctgtta actttgcaag taagtgtagc tttcaggaga    9600
gaagttctgg agacccaaaa gcttttgaac ttgagcaagg tcagagtcta gtcaagtact    9660
tgtcttgcac agtgattagg aagtatcttt ttaagactca agaagtcaac atggatttga    9720
ggagtgttgt atgtaatctc cgattttcca atttctcaat ttacaactgt tgggtcatgg    9780
agaaagggca agcagttca ggccctttgg gccttgggtc actt                      9824
```

-continued

<210> SEQ ID NO 44
<211> LENGTH: 2666
<212> TYPE: DNA
<213> ORGANISM: Oryzias latipes

<400> SEQUENCE: 44

| | | | | | |
|---|---|---|---|---|---|
| atgccctgcg | ttcaggctca | gtatggatca | tcacctcaag | gagccagtcc | tgcttcccag | 60 |
| agctacagct | accacaccgc | aggagagtac | agctgcgact | tcctaacacc | cgagtttgta | 120 |
| aagtttagca | tggacttgac | caacaccgag | atcacagcca | ccacttctct | cccgagtttc | 180 |
| agcacattca | tggacaacta | taacaccggt | tacgacgtga | aaccgccctg | tctgtatcag | 240 |
| atgccccact | ctggagaaca | atcctccatc | aaggtggagg | acgtccagat | gcacagctac | 300 |
| catcagcaga | gccacctgcc | gcctcagtca | gaggaaatga | tcgctcacac | tgggcccatg | 360 |
| tacttcaagc | cctcatcacc | tcacgccccg | agtacaccaa | acttccaagt | tcagcctaat | 420 |
| catatgtggg | aggaccctgg | ctccctccac | agtttccacc | agaactatgt | tgcagccaca | 480 |
| tctcacatga | tggagcagcg | caaaactccg | gtgtcgagac | tttcgctgtt | ctctttcaag | 540 |
| cagtccccgc | ctggcacgcc | tgtctccagc | tgccaaatgc | gctttgacgg | gccgctgcac | 600 |
| gtctccatga | cgcacgacaa | cccgggtgcg | caccgtggcc | tggacggtca | gagctttgcc | 660 |
| gtgcccagcg | ccataaggaa | acaggcgggt | ctggcttttc | cccactccct | gcaactcagc | 720 |
| cacgggcacc | agctggtgga | cagccaagtg | ccgtcgcccc | cgtcccgagg | atctccgtca | 780 |
| aacgagggtc | tgtgtgcggt | gtgtggagac | aacgcagcct | gccagcatta | tggagtgaga | 840 |
| acctgcgagg | gctgcaaagg | attttttcaag | cgcacggttc | agaaaaatgc | caaatacgtg | 900 |
| tgtttagcga | ataaaaactg | tcctgttgac | aaacgccgaa | gaaatcgttg | tcagttctgc | 960 |
| cgtttccaga | agtgccttgt | ggtcggcatg | gtaagagaag | gtacgtccaa | atcatgcttg | 1020 |
| aaaaagattt | cagaagtgtg | cgtaaaagca | atgttcacg | tgtgcatatg | aagttctctg | 1080 |
| cagaagcgtg | tgtggatcat | gtccattttc | catccatgca | gttgtccgaa | cggataattt | 1140 |
| gaaaggacga | cgagggcgcc | tgccatccaa | acccaaaagt | cctcaggagc | cctccccacc | 1200 |
| ttcgccgccg | gtgagcctca | taagcgcact | tgttagggcc | catgtggact | ccaatccctc | 1260 |
| catgtctgcg | ctggattatt | caagagtaag | acaaatatgt | tcggaaataa | atctcactca | 1320 |
| gacaacatct | aagagagagg | aagaaaaaac | aaaccatgat | tgaaagcttt | tattaactca | 1380 |
| atttctgcca | gacgcttgaa | ctggccgttt | ttattaacac | gacgcacatt | tttaaacttt | 1440 |
| gtcgagcttt | taatgcggca | cattttaagt | caataacttt | gaaatgcaga | atttaataaa | 1500 |
| aaagaagaca | tgaatttcat | agtgagtagt | tctcactctg | tcttagaaat | ggccatttgc | 1560 |
| aatttcacgg | attatatatt | ttaaaggacc | tcattaaggc | gctgtttaaa | ttaaattcca | 1620 |
| gttccaggca | aaccctgact | accaaatgac | tggagacaac | actcagcaca | ttcagcaatt | 1680 |
| ctatgatctc | ctgacgggct | ccatggagat | catccggggc | tgggcagaga | agattccggg | 1740 |
| cttctctgat | ctgccgaagc | aagatcaaga | tctcctcttt | gaatccgcct | tcctggagct | 1800 |
| cttcgtcctg | cggctggcat | acaggtccaa | tccagtggaa | gggaaactta | ttttttgcaa | 1860 |
| tggggtggtg | ttacacagac | tacaatgcgt | ccgcgggttt | ggagagtggg | tggatgcaat | 1920 |
| cgtggagttt | tcttctaact | tacagagctt | ggatatagac | atctcagctt | tctcctgcat | 1980 |
| cgcagctcta | gcgatggtaa | cagaacggca | cgggcttaag | gaacctaaga | gagttgagga | 2040 |
| tcttcaaaac | aagatagtga | actgcctcaa | agatcaagta | acgtttaata | gcggtggctt | 2100 |
| gaatcgtccc | aactacctat | caaaactcct | ggggaagctc | cccgaactgc | gcacgctctg | 2160 |

| | |
|---|---|
| tacccaaggt ctgcagcgta tcttttacct aaagctggaa gaccttgtcc ccccaccagc | 2220 |
| aataattgac aaacttttcc ttgacaccct acccttctga gttttacgca ctagccaaac | 2280 |
| ttcaaagaac ttccaaaaag actgagacaa acttatcaga ttacagtttc taattttttt | 2340 |
| tttgtcttt ttgcaagctc cgtaagctat tagaacaact tataaggatt taggcaacat | 2400 |
| caaaagtaac ggaagaaact gagtttttatc gctgcaggcc ttttatttta catttttctt | 2460 |
| tttgttctat ttttattctg tgcgaattag gtggatgttt tttttagca gaaatctctt | 2520 |
| tcaagccctt cttgtttatt gaacgtcggc tctgctgaat cactaagttg taatatattc | 2580 |
| catttatata aacagtatat ataaagtac acgcacacaa accctgtata ttataatgat | 2640 |
| agaaaatggg atgcatccag cgcatc | 2666 |

<210> SEQ ID NO 45
<211> LENGTH: 2458
<212> TYPE: DNA
<213> ORGANISM: Mouse

<400> SEQUENCE: 45

| | |
|---|---|
| acgtgtgagg acgcaaggtc tggggcgggg gaggggcagg tggagcgtag catcaccacg | 60 |
| gacttcacgg acctggggttg cagaagtcac acttctttcg gaaaaaaaaa aatccaccca | 120 |
| agtgggctac caaggtgaac cgttcccacc ttaaaatcag ccccagtcgt gacgtcaggt | 180 |
| cggaaatata ccaaagcgag cgcgggccag gagtccgggg agcgcggcgg ctcggcgatt | 240 |
| ggaccgcggg ccgctgacgc gggctgacgc gcgcagactt taggtgcatg ttggcagcag | 300 |
| cagctcgagc cacataaaca aaggcacatt ggcggccagg gccagtccgc ccgcggctc | 360 |
| cgcacagctc cgcgtccctc tctccggccc cgctggctgc ctccctctcc tgcgccgggg | 420 |
| ctggctgcgt gtggctctcc gcgccccgct tccgcagcgc tcccgcggac ccgggctcct | 480 |
| ctgctcccgg agggaactgc acttcggcgg agttgaatga atgaagagag cggacaagga | 540 |
| gatctgacgg gctggattcc caatagctct ttttaaaat cttggaaact ttgtccttcg | 600 |
| ctgaattacg acactgtcca cctttaattt cctcgaaaac tccataact ctgctgaagc | 660 |
| catgccttgt gttcaggcgc agtatgggtc ctcgcctcaa ggagccagcc ccgcttctca | 720 |
| gagctacagt taccactctt cgggagaata cagctccgat ttcttaactc cagagtttgt | 780 |
| caagtttagc atggacctca ccaacactga aattactgcc accacttctc tccccagctt | 840 |
| cagtaccttt atgacaaact acagcacagg ctacgacgtc aagccacctt gcttgtacca | 900 |
| aatgcccctg tccggacagc agtcctccat taaggtagaa gacattcaga tgcacaacta | 960 |
| ccagcaacac agcccacctgc cccctcagtc cgaggagatg atgccacaca gcgggtcggt | 1020 |
| ttactacaag ccctcttcgc ccccgacacc cagcacccccg agcttccagg tgcagcatag | 1080 |
| cccgatgtgg gacgatccgg gctcccttca caacttccac cagaactacg tggccactac | 1140 |
| gcatatgatc gagcagagga agacacctgt ctcccgcctg tcactcttct cctttaagca | 1200 |
| gtcgccccg ggcactcctg tgtctagctg ccagatgcgc ttcgacgggc tctgcacgt | 1260 |
| ccccatgaac ccggagcccg cgggcagcca ccacgtagtg gatgggcaga ccttcgccgt | 1320 |
| gcccaacccc attcgcaagc cggcatccat gggcttcccg ggcctgcaga tcggccacgc | 1380 |
| atcgcagttg cttgacacgc aggtgccctc gccgccgtcc cggggctctc cctccaatga | 1440 |
| gggtctgtgc gctgtttgcg gtgacaacgc ggcctgtcag cactacggtg ttcgcacttg | 1500 |
| tgagggctgc aaaggtttct ttaagcgcac ggtgcaaaaa aacgcgaaat atgtgtgttt | 1560 |
| agcaaataaa aactgcccag tggacaagcg ccgccgaaat cgttgtcagt actgtcggtt | 1620 |

-continued

```
tcagaagtgc ctagctgttg ggatggttaa agaagtggtt cgcacggaca gtttaaaagg    1680
ccggagaggt cgtttaccct cgaagccgaa gagcccacag gatccctctc ccccctcacc    1740
tccggtgagt ctgatcagtg ccctcgtcag agcccacgtc gattccaatc cggcaatgac    1800
cagcctggac tattccaggt tccaggcaaa ccctgactat cagatgagtg gagatgatac    1860
ccaacatatc cagcagttct acgatctcct gaccggctct atggagatca tcagagggtg    1920
ggcagagaag atccctggct ttgctgacct gcccaaagcc gaccaggacc tgcttttgga    1980
atcagctttc ttagaattat ttgttctgcg cttagcatac aggtccaacc cagtggaggg    2040
taaactcatc ttttgcaatg gggtggtctt gcacaggttg caatgcgtgc gtggctttgg    2100
ggaatggatt gattccattg ttgaattctc ctccaacttg cagaatatga acatcgacat    2160
ttctgccttc tcctgcattg ctgccctggc tatggtcaca gagagacacg ggctcaagga    2220
acccaagaga gtggaagagc tacaaaacaa aattgtaaat tgtcttaaag accatgtgac    2280
tttcaataat gggggtttga accgacccaa ctacctgtct aaactgttgg ggaagctgcc    2340
agaactccgc accctttgca cagggcct ccagcgcatt ttctacctga aattggaaga    2400
cttggtacca ccaccagcaa taattgacaa acttttcctg gacaccttac ctttctaa     2458
```

<210> SEQ ID NO 46
<211> LENGTH: 3427
<212> TYPE: DNA
<213> ORGANISM: Human

<400> SEQUENCE: 46

```
gctcgcgcac ggctccgcgg tcccttttgc ctgtccagcc ggccgcctgt ccctgctccc      60
tccctccgtg agtgtccggg ttcccttcgc ccagctctcc caccCctacc cgaccccggc     120
gcccgggctc ccagagggaa ctgcacttcg gcagagttga atgaatgaag agagacgcgg     180
agaactccta aggaggagat tggacaggct ggactcccca ttgcttttct aaaaatcttg     240
gaaactttgt ccttcattga attacgacac tgtccacctt taatttcctc gaaaacgcct     300
gtaactcggc tgaagccatg ccttgtgttc aggcgcagta tgggtcctcg cctcaaggag     360
ccagccccgc ttctcagagc tacagttacc actcttcggg agaatacagc tccgatttct     420
taactccaga gtttgtcaag tttagcatgg acctcaccaa cactgaaatc actgccacca     480
cttctctccc cagcttcagt accttatgg acaactacag cacaggctac gacgtcaagc     540
caccttgctt gtaccaaatg cccctgtccg gacagcagtc ctccattaag gtagaagaca     600
ttcagatgca caactaccag caacacagcc acctgccccc ccagtctgag gagatgatgc     660
cgcactccgg gtcggtttac tacaagccct cctcgcccccc gacgccacc accccgggct     720 tccaggtgca gcacagcccc atgtgggacg acccgggatc tctccacaac ttccaccaga     780
actacgtggc cactacgcac atgatcgagc gaggaaaac gccagtctcc cgcctctccc     840
tcttctcctt taagcaatcg cccctggca ccccggtgtc tagttgccag atgcgcttcg     900
acggccccct gcacgtcccc atgaacccgg agccgccgg cagccaccac gtggtggacg     960
ggcagacctt cgctgtgccc aacccccattc gcaagcccgc gtccatgggc ttcccgggcc    1020
tgcagatcgg ccacgcgtct cagctgctcg cacgcaggt gccctcaccg ccgtcgcggg    1080
gctccccctc caacgagggg ctgtgcgctg tgtgtgggga caacgcggcc tgccaacact    1140
acggcgtgcg cacctgtgag ggctgcaaag gcttctttaa gcgcacagtg caaaaaaatg    1200
caaaatacgt gtgtttagca aataaaaact gcccagtgga caagcgtcgc cggaatcgct    1260
```

```
gtcagtactg ccgatttcag aagtgcctgg ctgttgggat ggtcaaagaa gtggttcgca    1320
cagacagttt aaaaggccgg agaggtcgtt tgccctcgaa accgaagagc ccacaggagc    1380
cctctccccc ttcgccccg gtgagtctga tcagtgccct cgtcagggcc catgtcgact     1440
ccaacccggc tatgaccagc ctggactatt ccaggttcca ggcgaaccct gactatcaaa    1500
tgagtggaga tgacacccag catatccagc aattctatga tctcctgact ggctccatgg    1560
agatcatccg gggctgggca gagaagatcc ctggcttcgc agacctgccc aaagccgacc    1620
aagacctgct tttgaatca gctttcttag aactgtttgt ccttcgatta gcatacaggt     1680
ccaacccagt ggagggtaaa ctcatctttt gcaatgggt ggtcttgcac aggttgcaat     1740
gcgttcgtgg ctttgggaa tggattgatt ccattgttga attctcctcc aacttgcaga     1800
atatgaacat cgacatttct gccttctcct gcattgctgc cctggctatg gtcacagaga    1860
gacacgggct caaggaaccc aagagagtgg aagaactgca aaacaagatt gtaaattgtc    1920
tcaaagacca cgtgactttc aacaatgggg ggttgaaccg ccccaattat ttgtccaaac    1980
tgttggggaa gctcccagaa cttcgtaccc tttgcacaca ggggctacag cgcattttct    2040
acctgaaatt ggaagacttg gtgccaccgc cagcaataat tgacaaactt ttcctggaca    2100
cttttacctt ctaagacctc ctcccaagca cttcaaagga actggaatga taatggaaac    2160
tgtcaagagg gggcaagtca catgggcaga gatagccgtg tgagcagtct cagctcaagc    2220
tgccccccat ttctgtaacc ctcctagccc ccttgatccc taaagaaaac aaacaaacaa    2280
acaaaaactg ttgctatttc ctaacctgca ggcagaacct gaaagggcat tttggctccg    2340
gggcatcctg gatttagaac atggactaca cacaatacag tggtataaac ttttttattct   2400 cagtttaaaa atcagtttgt tgttcagaag aaagattgct ataaggtata atgggaaatg    2460
tttggccatg cttggttgtt gcagttcaga caaatgtaac acacacacac atacacacac    2520
acacacacac agagacacat cttaagggga cccacaagta ttgccctta caagacttc      2580 aaagttttct gctgtaaaga aagctgtaat atatagtaaa actaaatgtt gcgtgggtgg    2640
catgagttga agaaggcaaa ggcttgtaaa tttacccaat gcagtttggc tttttaaatt    2700
attttgtgcc tatttatgaa taaatattac aaattctaaa agataagtgt gtttgcaaaa    2760
aaaaagaaaa taaatacata aaaagggac aagcatgttg attctaggtt gaaaatgtta    2820
taggcacttg ctacttcagt aatgtctata ttatataaat agtatttcag acactatgta    2880
gtctgttaga ttttataaag attggtagtt atctgagctt aaacattttc tcaattgtaa    2940
aataggtggg cacaagtatt acacatcaga aaatcctgac aaaagggaca catagtgttt    3000
gtaacaccgt ccaacattcc ttgtttgtaa gtgttgtatg taccgttgat gttgataaaa    3060
agaaagttta tatcttgatt attttgttgt ctaaagctaa acaaaacttg catgcagcag    3120
cttttgactg tttccagagt gcttataata tacataactc cctggaaata actgagcact    3180
ttgaattttt tttatgtcta aaattgtcag ttaatttatt attttgtttg agtaagaatt    3240
ttaatattgc catattctgt agtattttc tttgtatatt tctagtatgg cacatgatat     3300
gagtcactgc cttttttttct atggtgtatg acagttagag atgctgattt tttttctgat   3360
aaattctttc tttgagaaag acaatttaa tgtttacaac aataaaccat gtaaatgaaa    3420
aaaaaaa                                                             3427
```

<210> SEQ ID NO 47
<211> LENGTH: 276
<212> TYPE: DNA
<213> ORGANISM: Mouse

```
<400> SEQUENCE: 47
gctcactgaa ccccagagaa tgggagagct acctcacgaa attgtgaatt gttttccaga    60
ccatgtgatt ttcaataaag ggggtttgaa ccgacccaac taccagttta aactgttggg   120
gaagctgcca gaaatccgca ccctttgcac acagggcctc cagcgcattt tttacctgaa   180
attggaagac ttggtaccac caccaccaat aattgacaaa cttttcctgg acaccttacc   240
tttctaagac cttttcccaa gcacgtcaaa gaaccg                             276

<210> SEQ ID NO 48
<211> LENGTH: 310
<212> TYPE: DNA
<213> ORGANISM: Mouse

<400> SEQUENCE: 48
ccgcttccct ctttctcctc ctcaaatata gacacttcct ctccaaccct agacatacgt    60
aattttacaa tacaaaatat aaacattctt aaaaaccatc tgactttcaa ttattgtgtt   120
tgaacccacc caactacctg tcttaactgt tggggaatct cccagaactc cccaccctct   180
ccacacacgt cctccagccc attttttacc tgaaattgga agacttggta ccaccaccag   240
caataattga ccaacttttc ctggacacct tacctttcta agaccttctc ccaagcacgt   300
caaagaactg                                                          310

<210> SEQ ID NO 49
<211> LENGTH: 208
<212> TYPE: DNA
<213> ORGANISM: Mouse
<220> FEATURE:
<221> NAME/KEY: misc_feature
<222> LOCATION: (1)..(208)
<223> OTHER INFORMATION: n = unknown

<400> SEQUENCE: 49
ttcttggagn gagtttgaac cgacccaact acctgtctaa actgttgcgg aacccgccag    60
aactccccac cctttccaca caggccctcc accccatttt ctacctgaaa ttggaagact   120
tggtaccacc accagcaata attgacaaac ttttcctgga caccttacct ttctaagacc   180
ttttcccaag cacttcaaag aactggaa                                      208

<210> SEQ ID NO 50
<211> LENGTH: 169
<212> TYPE: DNA
<213> ORGANISM: Mouse

<400> SEQUENCE: 50
atcaatcgtt ggggttgctg ccacgactcc gcacccttc cacaccggtc ctcctgcgca     60
ttttctacct gaaattggaa gacttggtac caccaccagc aattattgac caacttttcc   120
ttgacacctt acctttctaa gaccttctcc caagcacgtc aaagaactg                169

<210> SEQ ID NO 51
<211> LENGTH: 289
<212> TYPE: DNA
<213> ORGANISM: Mouse

<400> SEQUENCE: 51
cacatacaca ccggctctag gaaccccaga gagtcgaaga cccacaacac actattgtaa    60
attttcttaa agaccatttg actttccatc acggggggttt gaacccaccc aacaaccgt   120
```

```
ctatactgtt ggggaagctc ccagaactcc ccacccttt cacacaggcc ctccagcgca      180
ttttctacct gaaattggaa gacttggtac caccaccagc aataattgac aaacttttcc      240
tggacacctt acctttctta gaccttctcc caagcacgtc aaagaactg                  289
```

<210> SEQ ID NO 52
<211> LENGTH: 263
<212> TYPE: DNA
<213> ORGANISM: Mouse

<400> SEQUENCE: 52

```
gattggaaga catacccca tggattccca tccttttaat gaccatgtga ctttccataa       60
agggggtttg aactgaccca accacctgtc taaactgtcg gggcacctgc cagaactccc     120 cacccttttgc acacaggccc tccacccat tttctacctg aaattggaag acttggtacc    180
accaccagca ataattgaca aacttttcct ggacaccta cctttctaag acctttccc      240 aagcacttca aagaactgga tag                                              263
```

<210> SEQ ID NO 53
<211> LENGTH: 172
<212> TYPE: DNA
<213> ORGANISM: Mouse

<400> SEQUENCE: 53

```
gtctaaactc ttcgggaagc agccagaact ccccacccct tgcacacagg gcctccagcg       60
cattttttac ctgaaattgg aagacttggt accaccacca gcaataattg acaaactttt     120
cctggacacc ttacctttct aagaccttat cccaagcacg tcaaagaact gg              172
```

<210> SEQ ID NO 54
<211> LENGTH: 210
<212> TYPE: DNA
<213> ORGANISM: Mouse

<400> SEQUENCE: 54

```
gactttctcc aatgcggtta gaaccgaccc aattacccct ttaaactgtt ggggaagatc       60
ccagaattcc gcacccttttg cacacagggc ttccagcgca ttttttacct gaaattggaa    120
gacttggtac caccaccagc aataattgac aaacttttcc tggacacctt acctttctaa    180
gaccttttcc caagcacgtc aaagaactgg                                       210
```

<210> SEQ ID NO 55
<211> LENGTH: 10883
<212> TYPE: DNA
<213> ORGANISM: Human

<400> SEQUENCE: 55

```
ttccccgtgg ccgcgccctg ctccctcgcg gaagggggaag ggaacccggg agggcgcctc      60
tgagctggag ttgctgctat tttgggccca gcctggccgg tgcgtcaatg cctgcgcccc     120
tgcgtcaccg ccaccccac ccccttcctt ctccccagct ctccaaactc tcacttttc      180 cctttcgttc gcatggaatc gcttctgccc acggggcgct gacgctaccg agctcatgct    240
aatatgctat tcttcgccct cccctcctca tccccctact cacacaccct cacccgccac    300
cacaacccgc ccccccacc cacttcctgg ttttattttt tttctcgcgc ccgctagggc    360
atcgccgagc agcggcggcg gcggcggcag cagcagcggc agccgcaaca tctgggggaa    420
acttaaggtg gtcacgtagg tttccccgag gctgcggcgc aaaagagccc gcggcttcct    480
ggggcagccg cagggcatct gatggcaacg cctccccagc cgccggcgag ctgggggcag    540
```

-continued

```
cagggagtag gcaaaggcgg ggctgcagat tagggttgag cagcccggga tcccgaatag    600
ttccacggag ccatcggccg gtactgagaa cacgagtagg ggggcaagtt gcaaaagggt    660
cccggctgcc tggaaacgag ccacaccgag aaaggagggg cggctgggac gctctgcgcg    720
agtagaaaag cggggcggc  tccgaactct ccctcccaag gcccagccgc tggaagcccc    780 gcggagaag  ccctaggaag ccctcccagc tccggccggg agacggggag ggggcttgcc    840
ctccggagct gcggcgtttc ctttgctaga aagctccctg cgctctcggc gtggctaggg    900
gaaatgactt gcaaagcaga agcggcggcg acttggacgg ccgcgggggt gggacacgct    960
cccacagcca gctcgggccc ctctcctggc tgggctgtag gctcacacct tacgctttgc   1020
ggagacgctg cccccaatcc ccacccgctt cgcttttctt gtccagtctt tctgggctct   1080
aagattgagg ctgtgataga ccttgtgttt caaacgaaga tcgatttatt cccttaaaac   1140
tcgtggaagg ggtacgagtt ggtgggcaca gaggagtatc gaaagtatta agagtttgca   1200
agaaaggtgg ggaatcaaga gtacctttct tgcagaaggc gcacctgttg cctgctgctc   1260
ggcttgcatt gtctgcgaaa ggaaaagggg cgacgcttca ctctgacttt tgggttttct   1320
aaagagctgg gtcacggtca ctggctacct tttcccttct tatcccccc  ccccgcaag    1380 caccacgtcc tccatcgaac gtgggcactg catggaaata aggaaacata gaaaataag    1440 ccctaccccc actcccattc cctttcagat gggagtgtgg ggggtggggg tgggtagag    1500 agagtgagag agagagataa ttagaatgaa tatatgccag aagaggagga ggcctgggac   1560
aggaaaaggg agtaaaaggg gatgaaccgg gtagggaaat cccacccgaa ctgcgtgagc   1620
cctctgagcg tctcgtgtca tgggacatct gtacgctctt ccgctaaggg ggtgacgaag   1680
gtgggtggga gaggttaggg cgctgcaagg cacatcccat tccgtgcggc tccaggtgcg   1740
tactacctgg cccacgccgg ccttgccttc cgccggtgct tttgttgcac cctccccaca   1800
tgtgagcggc cgagccgctg cgcgggcgca ggggcttcgg ggaaagtgaa gtgtcgcgac   1860
gctgcgggct gcgcagacct gggagaggtc acacctcttt cggaaaaaaa aaaagaaaag   1920
aaaaaaaaca ccaaaaacca cccaagctgg ctaccaaggt gaacgcagag cggttcccac   1980
cttaaaatcg gccctgctcg tgacgtcagg tcggaaatat accaaagcga gcgcgggcca   2040
ggagtccagg gagcgcggca gcgcggcgat tgggcggcgg gccgctgacg cgcgctgacg   2100
cgcggagact ttaggtgcat gttggcagcg gcagcgcaag ccacataaac aaaggcacat   2160
tggcggccag ggccagtccg cccggcggct cgcgcacggc tccgcggtcc cttttgcctg   2220
tccagccggc cgcctgtccc tgctccctcc ctccgtgagt gtccgggttc ccttcgccca   2280
gctctcccac ccctacccga ccccggcgcc cgggctccca gagggaactg cacttcggca   2340
gagttgaatg aatgaagaga gacgcggaga actcctaagt gagtagatgc agcccatgca   2400
gttcggccct tcttttatgc ttttttcctt ttttgcacgt ctcttctttc ccacttgtgt   2460
gggacaggtt ctctggaaag tgggagccag aggcttccta gtgagagtgg gaccgaagga   2520
tggggagtgc gtgcgcgcag ttaccggggg gcatttgttc gaactccggc tttggcacta   2580
gtggggagtt ggctctcgac agaggtttcc aggctcctca ttggtggacg tggaagggag   2640
actccacagt ttgggagctg aggactagcc cgcggaaatg tgcgcaaagt ttggctgtta   2700
gtgaggaatt gattgtggcc tgtgaacacg gagactccaa gtcctatgta tacgagggaa   2760
gctgcccaca aactgacagg gagagggaagt tcttcagttt atgcgttgct tgggaactgt   2820
gtctccgcgg ctggccagcg cgcgatgttt cccgggtatt gttgagtaag ggtggtgttg   2880
```

-continued

```
gtagccgtgt cctgttacta agttgcctga aatttctggt tttgacatat gctgtccttg    2940
ggtttgcgaa tgtatcagag cgagaatatg aatatgtaaa gagtcagtta tgaaactgtg    3000
gagctaccag ggggttaata tccaacacag gaatatctct aagggctgtg gggttcgagt    3060
ctcctttctg cttttctggg gtaatcttcc ccccaccccc accaccacta tgaagcaaga    3120
ttgtggggga gggaaagaa  taaaaagaga ggatactggc tttctttttt cattagtaat    3180
aagattgtct gtgctctaga atgtcttcca agtgggaaca tctgaaaatt actaggacac    3240
aagaatgcct tgttccagaa aggcagattg tggaaggcat tatggggaag gtgttcatct    3300
tgctgtgctg ggaaacactt ctaatattgg tgccaatacc atataagcag tatgtccccc    3360
ctctgcaatt gacctaagaa gctcctggaa aagtagatcc cctcttccca ccttgtgacc    3420
attaaagcct tgtgaccatt aaagatgctg aaagacaagt tttctggaaa agtgaacatc    3480
aatttatctg tagctccaat cccagtgctc tgtcaaaagc actttagaag tgcggatgct    3540
tccactcaac ttgccttctc agtcaaggcc tttctaacat tttgtaaggg gaagattgt     3600
tttctcattt tatattcttg acttctactt tcttcccctc taccaaaaga aaaggcaatt    3660
tcaccacaag aaaaaaaaat gcaagagaag gttccaatgc tgtattttca tactctagtc    3720
ttcatactca ggtcctgaat taacctaaga tggaaatgac ctctccacct acactgtagc    3780
aaagggccca gttcattaca tcataaatgt taaatgagtt catggactag ctttcctctt    3840
gcaggatctt ctctctgcaa ggatttacac agtgcaatgg gtggtatttt ctgttgtttc    3900
aagtcatttc ttttatacat tcattttaag tgctatgttt ggtaaaggct tcccactcat    3960
ttccaatgag acaaacaggg aaggcatgga agggcctgcc tggtgagtct acatatgccc    4020
agctgaatct ctgtcgggaa gaaaccctga agcttcctgt gtctgtattt cagggaggag    4080
attggacagg ctggactccc cattgctttt ctaaaaatct tggaaacttt gtccttcatt    4140
gaattacgac actgtccacc tttaatttcc tcgaaaacgc ctgtaactcg gctgaaggtt    4200
agtgcaactt catttctttc ctttactctc cagagctccc caaacatcaa gaaacaggac    4260
aaggcaaacc ctgtaactta aggttttgccc gacccatcgc cttcgggaac aactttctca    4320
ttgtgaaatt caacttcatt tctagatggt catttctaga aagagactgc tgaatctgag    4380
cttcagagaa gaggctcatc tgagtgggat gagtgggggg gtatgaggga gatgtttgga    4440
aatacccagg agtgtagacc ctcagtagct ttttagctct gggtctttat ttggttagtc    4500
tttccacgcc ctaaactgtt gttctgcagc attctctctc tcctgccttt cctctcgcgc    4560
ccctacatgc tctctgactg ccgcgggctg ccggtgtagc tccaggtgta cccgagcccg    4620
ggagaaagtg ttcagttgac caggctgagt gtgttatcac cctgtttcat ttccagccat    4680
gccttgtgtt caggcgcagt atgggtcctc gcctcaagga gccagcccg  cttctcagag    4740
ctacagttac cactcttcgg gagaatacag ctccgatttc ttaactccag agtttgtcaa    4800
gtttagcatg gacctcacca acactgaaat cactgccacc acttctctcc ccagcttcag    4860
tacctttatg gacaactaca gcacaggcta cgacgtcaag ccaccttgct tgtaccaaat    4920
gcccctgtcc ggacagcagt cctccattaa ggtagaagac attcagatgc acaactacca    4980
gcaacacagc cacctgcccc cccagtctga ggagatgatg ccgcactccg ggtcggttta    5040
ctacaagccc tcctcgcccc cgacgcccac caccccgggc ttccaggtgc agcacagccc    5100
catgtgggac gacccgggat ctctccacaa cttccaccag aactacgtgg ccactacgca    5160
catgatcgag cagaggaaaa cgccagtctc ccgcctctcc ctcttctcct ttaagcaatc    5220
gccccctggc accccggtgt ctagttgcca gatgcgcttc gacgggcccc tgcacgtccc    5280
```

-continued

```
catgaacccg gagcccgccg gcagccacca cgtggtggac gggcagacct tcgctgtgcc    5340
caacccatt cgcaagcccg cgtccatggg cttcccgggc ctgcagatcg ccacgcgtc      5400
tcagctgctc gacacgcagg tgccctcacc gccgtcgcgg ggctccccct ccaacgaggg    5460
gctgtgcgct gtgtgtgggg acaacgcggc ctgccaacac tacggcgtgc gcacctgtga    5520
gggctgcaaa ggcttcttta aggtgagcaa tggcgggagc ggagtaggca ggtagggagc    5580
ccctagtgcc cgggacctcg gagtgtgccc tctgccttgg tgccagtagc ccagcccag    5640
ctctcccggg actgcccagc tctccggggt ccgccgaagc tgccctgcag agaccatgg    5700
gctgcggcgg ggacttccgg gtgtctgaga aagggaagca gaaagactgg gaggccaggg    5760
tcgcatcccc ctcgcattca gccgacccgg ctggcccccg cccgaagttg ctggagccgg    5820
agttggaaga gggtcatttg catgtgctag gagctgtctt ccctgttcag aatgaaattg    5880
gttaggacag agaaccgtgt ctgagctaac caagtggaac agaattccct atggtcaaat    5940
taagtgatct ctttatttcg ccatcctgat tgaataatct tatcatttta aatagagaag    6000
gtctccaagg aaatgtaaat aatatgaatg cccacggatt tgtatttact gagcgtctcc    6060
ttctccttct cttggcatat aaaacacagc aaggagcggc aaggttagct caaatgttaa    6120
cgctatcaat tttcttctgt taaatgccct gggggaggaa aaaagaaaag aaagaaagaa    6180
aaggaagaga aaaaataaa atggaattgt gtgtatgtgt ttgtttgtgg ggaggaatcg    6240
tagaccccag tcacataaca gaaattttct ccgagttgcc tgattttcaa agaagaaaa    6300
aaaatgttgg tctatattgt ctccttttgc agcgcacagt gcaaaaaat gcaaaatacg    6360
tgtgtttagc aaataaaaac tgcccagtgg acaagcgtcg ccggaatcgc tgtcagtact    6420
gccgatttca gaagtgcctg gctgttggga tggtcaaaga aggtaggctg aggggagctg    6480
ccgaccctcc agtttgcgcc tttaggaaac cactgctcat actccagcat cacgttccac    6540
ttcccggtgc tggggatctc cgactccccc tcagtatggc ctccaggacc ctgcagctgc    6600
ctgcttgccc ggccttccct agagaaagcc gccaggccct tctctccttt aactatacga    6660
cccatttgga ggaagacata aaataacccc gcattttta atgcttctag tcagtgaagg    6720
ctttacaagc actggggccc tcagccgctc agcctggtgc cccgcggctg cggccttccc    6780
cggggaggga ccgaggcagc agctgggcct gggctcggaa aagcggcgct aacagggctc    6840
ttccttttgca gtggttcgca cagacagttt aaaaggccgg agaggtcgtt tgccctcgaa    6900
accgaagagc ccacaggagc cctctccccc ttcgcccccg gtgagtctga tcagtgccct    6960
cgtcagggcc catgtcgact ccaacccggc tatgaccagc ctggactatt ccagggtaag    7020
aagctggcgg gggggatatc atgtggacaa accgacagat gggcaggacc cctcccaca    7080
tccgtcatta actctcagat tcaacggggg taaagaaagg caagcaaggc tgtatatgcc    7140
tcgcagctct ggccagggcc tcaagattca gatcttcaga caaatccatg tagctggggg    7200
catagacatg aggacaggat ggaggaagga ggagagggac acgccacagg gtttgaagct    7260
gtgtgaattc ccactacccc actacccat cgcccctcct cttccatata caccagtgcc    7320
tctaccatga aatccagggg ctgtgcaaac tctccccctt cccaatctac tttattccca    7380
gtcctccata gagatagatg ctttaatcct catccttcct ggcactgtgc tgggaagga    7440
tgtgggggct gtctgggggt cagggaaggg aaggagaggg tgtaaagatg ccagtggggt    7500
gggggatcaa gtggtcagat ccttttactc cagctgtgaa aaatatgcgg gctttaattg    7560
gaggaagtat gttgagcaaa cctggtaggg actgcaattt tattaagatt tgcaaaaggg    7620
```

```
cgtctcagct cgaggcccac tctgggacta gcatgaatac taacatgtca attgttttgt      7680
ggagataaga gtgaacgttt cccagggctg gatggcactg tatttagtct gtatggaaat      7740
gacaatttac atatttaaag cagcgacctc gtagcaccat ccctaattga attaattgcc      7800
ccggaacatc taatttcctt actggtcaga gagaggttta attgttataa aaacctggct      7860
cccctattag aaacgggtt agcaatttca cgggttatat attttagaga acctcattaa      7920
gtgcttttta aaatgaaatt ccagttccag gcgaaccctg actatcaaat gagtggagat      7980
gacacccagc atatccagca attctatgat ctcctgactg gctccatgga gatcatccgg      8040
ggctgggcag agaagatccc tggcttcgca gacctgccca agccgacca agacctgctt       8100 tttgaatcag ctttcttaga actgtttgtc cttcgattag catacaggta ataagggagg      8160
gaggagacaa tccagggagg ctgtgagaga atcaagaaa ggaaagaaa gggaggaagg        8220 gaaaccagag ggtggggtag agaaaaagac agaataggaa atggaagtcg gagaaaggaa      8280
gaaaaagaaa gaaaacaaaa aaagacgaga agaagcgagc ccagaagcct tggatgaatg      8340
gaatggaggt gggatagggg gcgttcttga ttgttatgaa attaaaccct ttcaaggtcc      8400
actggatcta cattttaatt aactcttcag taattaggtg actcttaaat ccctcattta      8460
ttgctcttca gtaattagt tgtttagctt ttctctctct cttttctcc cctctctctc        8520 tttggtatta attgcaggtc caacccagtg gagggtaaac tcatcttttg caatggggtg      8580
gtcttgcaca ggttgcaatg cgttcgtggc tttggggaat ggattgattc cattgttgaa      8640
ttctcctcca acttgcagaa tatgaacatc gacatttctg ccttctcctg cattgctgcc      8700
ctggctatgg tcacaggtca gtactgcagg cgcagggcgc ttcccctcca gaactgccta      8760
gcaggatttg tcctgagttt cccttgtcac agaattctcc ttggttttgc caactagcta      8820
actgtcttgt acattcttct tttgtttctg attatgtttt ctgcagagag acacgggctc      8880
aaggaaccca agagagtgga agaactgcaa aacaagattg taaattgtct caaagaccac      8940
gtgactttca acaatggggg gttgaaccgc cccaattatt tgtccaaact gttggggaag      9000
ctcccagaac ttcgtacccct ttgcacacag gggctacagc gcattttcta cctgaaattg      9060
gaagacttgg tgccaccgcc agcaataatt gacaaacttt tcctggacac tttacctttc      9120
taagacctcc tcccaagcac ttcaaaggaa ctgaatgat aatggaaact gtcaagaggg       9180
ggcaagtcac atgggcagag atagccgtgt gagcagtctc agctcaagct gcccccccatt     9240 tctgtaaccc tcctagcccc cttgatccct aaagaaaaca aacaaacaaa caaaaactgt      9300
tgctatttcc taacctgcag gcagaacctg aaagggcatt ttggctccgg ggcatcctgg      9360
atttagaaca tggactacac acaatacagt ggtataaact ttttattctc agtttaaaaa      9420
tcagtttgtt gttcagaaga aagattgcta taaggtataa tgggaaatgt ttggccatgc      9480
ttggttgttg cagttcagac aaatgtaaca cacacacaca tacacacaca cacacacaca      9540
gagacacatc ttaaggggac ccacaagtat tgcccttaa caagacttca agttttctg        9600 ctgtaaagaa agctgtaata tatagtaaaa ctaaatgttg cgtgggtggc atgagttgaa      9660
gaaggcaaag gcttgtaaat ttacccaatg cagtttggct ttttaaatta ttttgtgcct      9720
atttatgaat aaatattaca aattctaaaa gataagtgtg tttgcaaaaa aaagaaaat      9780 aaatacataa aaagggaca agcatgttga ttctaggttg aaaatgttat aggcacttgc       9840
tacttcagta atgtctatat tatataaata gtatttcaga cactatgtag tctgttagat      9900
tttataaaga ttggtagtta tctgagctta aacattttct caattgtaaa ataggtgggc      9960
acaagtatta cacatcagaa aatcctgcca aaagggccac atagtgtttg taacaccgtc     10020
```

```
caacattcct tgtttgtaag tgttgtatgt accgttgatg ttgataaaaa gaaagtttat    10080
atcttgatta ttttgttgtc taaagctaaa caaaacttgc atgcagcagc ttttgactgt    10140
ttccagagtg cttataatat acataactcc ctggaaataa ctgagcactt tgaattttt     10200 ttatgtctaa aattgtcagt taatttatta ttttgtttga gtaagaattt taatattgcc    10260
atattctgta gtattttct ttgtatattt ctagtatggc acatgatatg agtcactgcc     10320 ttttttcta tggtgtatga cagttagaga tgctgatttt ttttctgata aattctttct    10380
ttgagaaaga caattttaat gtttacaaca ataaaccatg taaatgatac agaattttgt    10440 cttcttttg ggtcagaaaa aataatgact aaacagcaac ataacataca cagttggaga    10500
ttaatttggg ataggtcact tattcaatat ctgaatttta aacagcctaa atctattctg    10560
gcaaaagaaa tcaggtgaac cagaataatt atccagataa ttcagtaaaa tatttttct    10620 taaccagaat tttccagtct ggtgaccaat atttattagg atcaatttag aatatctcaa    10680
ttcttctgtt aactttgcaa gtaagtgtag ctttcaggag agaagttctg gagacccaaa    10740
agcttttgaa cttgagcaag gtcagagtct agtcaagtac ttgtcttgca cagtgattag    10800
gaagtatctt tttaagactc aagaagtcaa catggatttg aggagtgttg tatgtaatct    10860
ccgattttcc aatttctcaa ttt                                            10883

<210> SEQ ID NO 56
<211> LENGTH: 3421
<212> TYPE: DNA
<213> ORGANISM: Human

<400> SEQUENCE: 56
gctcgcgcac ggctccgcgg tccctttgc ctgtccagcc ggccgcctgt ccctgctccc       60
tccctccgtg aggtgtccgg gttcccttcg cccagctctc ccaccctac ccgaccccgg      120 cgcccgggct cccagaggga actgcacttc ggcagagttg aatgaatgaa acagacgcg      180 gagaactcct aaggaggaga ttggacaggc tggactcccc attgcttttc taaaaatctt     240 ggaactttg tccttcattg aattacgaca ctgtccacct ttaatttcct cgaaaacgcc      300
tgtaactcgg ctgaagccat gccttgtgtt caggcgcagt atgggtcctc gcctcaagga     360
gccagccccg cttctcagag ctacagttac cactcttcgg gagaatacag ctccgatttc     420
ttaactccag agtttgtcaa gtttagcatg gacctcacca acactgaaat cactgccacc     480
acttctctcc ccagcttcag tacctttatg gacaactaca gcacaggcta cgacgtcaag     540
ccaccttgct tgtaccaaat gccctgtcc ggacagcagt cctccattaa ggtagaagac      600
attcagatgc acaactacca gcaacacagc cacctgcccc ccagtctga ggagatgatg     660 ccgcactccg ggtcggttta ctacaagccc tcctcgcccc cgacgccac cacccgggc      720 ttccaggtgc agcacagccc catgtgggac gacccgggat ctctccacaa cttccaccag    780
aactacgtgg ccactacgca catgatcgag cagaggaaaa cgccagtctc ccgcctctcc    840
ctcttctcct ttaagcaatc gccccctggc acccggtgt ctagttgcca gatgcgcttc     900
gacgggcccc tgcacgtccc catgaaccg gagcccgccg gcagccacca cgtggtggac    960
gggcagacct tcgctgtgcc caaccccatt cgcaagcccg cgtccatggg cttcccgggc   1020
ctgcagatcg ccacgcgtc tcagctgctc gacacgcagg tgccctcacc gccgtcgcgg   1080 ggctcccccct ccaacgaggg gctgtgcgct gtgtgtgggg acaacgcggc ctgccaacac   1140
tacggcgtgc gcacctgtga gggctgcaaa ggcttcttta agcgcacagt gcaaaaaaat   1200
```

-continued

```
gcaaaatacg tgtgtttagc aaataaaaac tgcccagtgg acaagcgtcg ccggaatcgc    1260
tgtcagtact gccgatttca gaagtgcctg gctgttggga tggtcaaaga agtggttcgc    1320
acagacagtt taaaaggccg gagaggtcgt ttgccctcga aaccgaagag cccacaggag    1380
ccctctcccc cttcgccccc ggtgagtctg atcagtgccc tcgtcagggc ccatgtcgac    1440
tccaacccgg ctatgaccag cctggactat tccaggttcc aggcgaaccc tgactatcaa    1500
atgagtggag atgacaccca gcatatccag caattctatg atctcctgac tggctccatg    1560
gagatcatcc ggggctgggc agagaagatc cctggcttcg cagacctgcc caaagccgac    1620
caagacctgc ttttttgaatc agcttttctta gaactgtttg tccttcgatt agcatacagg    1680
tccaacccag tggagggtaa actcatcttt tgcaatgggg tggtcttgca caggttgcaa    1740
tgcgttcgtg gctttgggga atggattgat tccattgttg aattctcctc caacttgcag    1800
aatatgaaca tcgacatttc tgccttctcc tgcattgctg ccctggctat ggtcacagag    1860
agacacgggc tcaaggaacc caagagagtg gaagaactgc aaaacaagat tgtaaattgt    1920
ctcaaagacc acgtgacttt caacaatggg gggttgaacc gccccaatta tttgtccaaa    1980
ctgttgggga agctcccaga acttcgtacc ctttgcacac aggggctaca gcgcattttc    2040
tacctgaaat tggaagactt ggtgccaccg ccagcaataa ttgacaaact tttcctggac    2100
actttacctt tctaagacct cctcccaagc acttcaaagg aactgaatg ataatggaaa    2160 ctgtcaagag ggggcaagtc acatgggcag agatagccgt gtgagcagtc tcagctcaag    2220 ctgccccca tttctgtaac cctcctagcc cccttgatcc ctaaagaaaa caaacaaaca    2280
aacaaaaact gttgctattt cctaacctgc aggcagaacc tgaaagggca ttttggctcc    2340
ggggcatcct ggatttagaa catggactac acacaataca gtggtataaa cttttttattc    2400 tcagtttaaa aatcagtttg ttgttcagaa gaaagattgc tataatgtat aatgggaaat    2460
gtttggccat gcttggttgt tgcagttcag acaaatgtaa cacacacaca catacacaca    2520
cacacacaca cacagagaca catcttaagg ggacccacaa gtattgccct ttaacaagac    2580
ttcaaagttt tctgctgtaa agaaagctgt aatatatagt aaaactaaat gttgcgtggg    2640
tggcatgagt tgaagaaggc aaaggcttgt aaatttaccc aatgcagttt ggcttttttaa    2700 attattttgt gcctatttat gaataaatat tacaaattct aaaagataag tgtgtttgca    2760 aaaaaaaga aaataaatac ataaaaaagg gacaagcatg ttgattctag gttgaaaatg    2820
ttataggcac ttgctacttc agtaatgtct atattatata aatagtattt cagacactat    2880
gtagtctgtt agatttttata aagattggta gttatctgag cttaaacatt ttctcaattg    2940
taaaataggt gggcacaagt attacacatc agaaaatcct gacaaagggg acacatagtg    3000
tttgtaacac cgtccaacat tccttgtttg taagtgttgt atgtaccgtt gatgttgata    3060 aaagaaagt ttatatcttg attattttgt tgtctaaagc taaacaaaac ttgcatgcag    3120
cagcttttga ctgtttccag agtgcttata atatacataa ctccctggaa ataactgagc    3180
actttgaatt ttttttatgt ctaaaattgt cagttaattt attattttgt ttgagtaaga    3240
attttaatat tgccatattc tgtagtattt ttctttgtat atttctagta tggcacatga    3300
tatgagtcac tgcctttttt tctatggtgt atgacagtta gagatgctga ttttttttct    3360
gataaattct ttctttgaga aagacgaatt ttaatgttta caacaataaa ccatgtaaat    3420
g                                                                    3421
```

<210> SEQ ID NO 57
<211> LENGTH: 239

<212> TYPE: DNA
<213> ORGANISM: Mouse

<400> SEQUENCE: 57

| | | | | | |
|---|---|---|---|---|---|
| ttctcttcta | tttctaaaat | tttcaatcaa | tatattattt | tatgtttgag | taagaattttt | 60 |
| aatattgcca | tattctctag | tattttcttt | ctatattttt | aataccgcac | atgagatgat | 120 |
| tcactgcctt | ttttttatg | gtgtacgaca | gttagagatg | ctgatttttt | tttcctgata | 180 |
| aattttttt | ttaagaaaga | caatttaat | gtttacaaca | ataaaccacc | taaatgagc | 239 |

<210> SEQ ID NO 58
<211> LENGTH: 241
<212> TYPE: DNA
<213> ORGANISM: Mouse

<400> SEQUENCE: 58

| | | | | | |
|---|---|---|---|---|---|
| ttttgttttt | tatgtctaaa | attgtcagtc | aatatattat | tttatgtttg | agtaagaatt | 60 |
| ttaatattgc | catattctgt | agtattttct | ttgtatattt | ttagtacggc | aaatgagatg | 120 |
| attcactccc | tttttttta | tggtgtacga | cagttagaga | tgctgatttt | tttttcctga | 180 |
| taaatttttt | ctttaagaaa | gacaattta | atgtttacaa | cataaaccca | cgtaaatgag | 240 |
| c | | | | | | 241 |

<210> SEQ ID NO 59
<211> LENGTH: 239
<212> TYPE: DNA
<213> ORGANISM: Mouse

<400> SEQUENCE: 59

| | | | | | |
|---|---|---|---|---|---|
| ttgtttttta | tgtctaaaat | tttcagtcca | tatattattt | tatgtttgac | taaggattttt | 60 |
| aatattccca | tattttgtag | tattttcttt | gtatatttct | agtacggcac | atgagatgag | 120 |
| tcactcccctt | ttttctatgg | tgtacgacag | ttagagatgc | tgatttttt | ttcctgataa | 180 |
| attctttttt | taagaaagac | aatttaatg | tttacaacaa | taaaccacgt | agatgaatt | 239 |

<210> SEQ ID NO 60
<211> LENGTH: 253
<212> TYPE: DNA
<213> ORGANISM: Mouse

<400> SEQUENCE: 60

| | | | | | |
|---|---|---|---|---|---|
| cactttgaac | tttttttgttt | ttgtttttta | tgtctaaaat | tctcactcaa | catattattt | 60 |
| tatgtttgag | taaggattttt | catattccca | tattttgtag | tattttcttt | gtatatttct | 120 |
| agtacggcac | atgagatgac | tcactgcctt | tttttttatg | gtgtacgaca | gttagagatg | 180 |
| ctgatttttt | tttcctgata | aattcttttt | ttaagaaaga | caattttaat | gtttacaaca | 240 |
| ataaaccacg | taa | | | | | 253 |

<210> SEQ ID NO 61
<211> LENGTH: 270
<212> TYPE: DNA
<213> ORGANISM: Mouse

<400> SEQUENCE: 61

| | | | | | |
|---|---|---|---|---|---|
| tggaaattac | ctgaccactt | tgaatttttt | tgtttttgt | ttttatgtc | tagaattgtc | 60 |
| agtcaatata | tattttatg | tttgagtaag | aatttaata | ttgccatatt | ctgtagtatt | 120 |
| ttctttgtat | atttctagta | cggcacatga | gatgagtcac | tgcctttttt | ttctatggtg | 180 |

```
tacgacagtt agagatgctg attttttttt cctgataaat tctttcttta agaaagacaa    240
ttttaatgtt tacaacaata aaccacgtaa                                     270

<210> SEQ ID NO 62
<211> LENGTH: 239
<212> TYPE: DNA
<213> ORGANISM: Mouse

<400> SEQUENCE: 62
taattctaaa ttctcttaat gaccatctga ctttcaataa tgggcatctg aaccgaccca    60
actacctctt taaactgttg gggaagctgc caggattccg caccctttgc acacagggcc   120
tccagcgcat tttttacctg aaattggaag acttggtacc accaccagca ataattgaca   180
aacttttcct ggacacctta cctttctaag accttttccc aagcacttca agaactgg    239

<210> SEQ ID NO 63
<211> LENGTH: 253
<212> TYPE: DNA
<213> ORGANISM: Mouse

<400> SEQUENCE: 63
gaattccttt gttttcttc tttacgtcta aaattgtcag tcaaatatat attctaagtc     60
tgagtaagaa ttttaatatt gccatattca gtagtatttt cttcgaatat ttctagtacg   120
gcacatgaga tgagtcactg ccttttttt tatggtgtac gacagttaga gatgctgatt    180
tttttttcct gataaattct ttctttaaga agacaatttt aatgtttac aacataaac     240 cacgtaaatg aac                                                       253

<210> SEQ ID NO 64
<211> LENGTH: 262
<212> TYPE: DNA
<213> ORGANISM: Mouse

<400> SEQUENCE: 64
cataaattca tattcctatc cctctatttt tcattacct acaaaattca ccagtccaaa     60
tcataaactt acgttgagta agaatcttta atatcgctat attctctagt attttctttg   120
tatatttcaa gtacggaaca tgagatgagt cactgctttt ttttttatgg tgtaggacag   180
ttagagatgc tgattttttt ttcctgataa atttttttctt taagaaagac aattttaatg   240
tttacaacaa taaacaacgt aa                                            262

<210> SEQ ID NO 65
<211> LENGTH: 2353
<212> TYPE: DNA
<213> ORGANISM: Mouse

<400> SEQUENCE: 65
gcgcgcccgg actgcaggac gagctggagc tgggctgctc gaccactccg cgcccgggga    60
ctcggcgacc tggggccggg agcgctgggc agggagatct gacgggctgg attcccaata   120
gctctttttt aaaatcttgg aaactttgtc cttcgctgaa ttcgacact gtccaccttt    180 aatttcctcg aaaactccaa taactctgct gaagcttcag tacctttatg gacaactaca   240
gcacaggcta cgacgtcaag ccaccttgct tgtaccaaat gccccgtgtcc ggacagcagt   300 cctccattaa ggtagaagac attcagatgc acaactacca gcaacacagc cacctgcccc   360
ctcagtccga gggagatgatg ccacacgcg ggtcggttta ctacaagccc tcttcgcccc   420
cgacacccag caccccgagc ttccaggtgc agcatagccc gatgtgggac gatccgggct   480
```

| | |
|---|---|
| cccttcacaa cttccaccag aactacgtgg ccactacgca tatgatcgag cagaggaaga | 540 |
| cacctgtctc ccgcctgtca ctcttctcct ttaagcagtc gcccccgggc actcctgtgt | 600 |
| ctagctgcca gatgcgcttc gacgggcctc tgcacgtccc catgaacccg agcccgcgg | 660 |
| gcagccacca cgtagtggat gggcagacct tcgccgtgcc caaccccatt cgcaagccgg | 720 |
| catccatggg cttcccgggc ctgcagatcg gccacgcatc gcagttgctt gacacgcagg | 780 |
| tgccctcgcc gccgtcccgg ggctctccct ccaatgaggg tctgtgcgct gtttgcggtg | 840 |
| acaacgcggc ctgtcagcac tacggtgttc gcacttgtga gggctgcaaa ggtttctta | 900 |
| agcgcacggt gcaaaaaaac gcgaaatatg tgtgtttagc aaataaaaac tgcccagtgg | 960 |
| acaagcgccg ccgaaatcgt tgtcagtact gtcggtttca gaagtgccta gctgttggga | 1020 |
| tggttaaaga gtggttcgc acggacagtt taaaaggccg gagaggtcgt ttaccctcga | 1080 |
| agccgaagag cccacaggat ccctctcccc cctcacctcc ggtgagtctg atcagtgccc | 1140 |
| tcgtcagagc ccacgtcgat tccaatccgg caatgaccag cctggactat tccaggttcc | 1200 |
| aggcaaaccc tgactatcag atgagtggag atgatcccca acatatccag cagttctacg | 1260 |
| atctcctgac cggctctatg gagatcatca gagggtgggc agagaagatc cctggctttg | 1320 |
| ctgacctgcc caaagccgac caggacctgc tttttgaatc agctttctta gaattatttg | 1380 |
| ttctgcgctt agcatacaga atatgaacat cgacatttct gccttctcct gcattgctgc | 1440 |
| cctggctatg gtcacagaga gacacggggct caaggaaccc aagagagtgg aagagctaca | 1500 |
| aaacaaaatt gtaaattgtc ttaaagacca tgtgactttc aataatgggg gtttgaaccg | 1560 |
| acccaactac ctgtctaaac tgttggggaa gctgccagaa ctccgcaccc tttgcacaca | 1620 |
| gggcctccag cgcatttct acctgaaatt ggaagacttg gtaccaccac cagcaataat | 1680 |
| tgacaaactt ttcctggaca ccttaccttt ctaagacctt ctcccaagca cgtcaaagaa | 1740 |
| ctggaaagaa aaaaaaaata acatccagag ggggctggtc acatgggcag agagctggtt | 1800 |
| gaagtgtcca gttcacctta tctcccttct gtagacccct agccctcacc ccttaagtaa | 1860 |
| acaaacaaac aaacaaacca caataaaaaa ctgtcgctat ttcctaacct gcaggcagaa | 1920 |
| cctgaagggg cattttggct ccggggcatc ctggatttag aaaacggaca gcacacagta | 1980 |
| cagtggtata aactttttat tatcagttca aaatcagttt gttgttcaga gaaagattg | 2040 |
| ctaatgtatg atgggaaatg tttggccatg cttgcttgtt gcagttaaga caaatgtgac | 2100 |
| acacacacac acacacacac acacacacac acacacacac cttaatggga ccctcctatt | 2160 |
| ttgccctta acaagacttc aaagtttcct gctgtaaaga aagctgtaat atatagtaaa | 2220 |
| actaaatgtt gcgtgggtgg catgaattga aggcagaggc ttgtaaattt atccaatgca | 2280 |
| gtttggcttt ttaaattatt ttgtgcctat ttatgaataa atattacaaa ttctaaaaag | 2340 |
| taagtgtgtt tgc | 2353 |

<210> SEQ ID NO 66
<211> LENGTH: 2154
<212> TYPE: DNA
<213> ORGANISM: Rat

<400> SEQUENCE: 66

| | |
|---|---|
| cggcacgagc cagggccagt ccgccccgcg ctccgcacgg ctctgcgtcc ctctctcctg | 60 |
| cccagccggc tgcctccctc tcctgcggcc gggctggctg cgtgtggctc tccgcgcccc | 120 |
| gctcccgcag cgctccagcg gaccccggct cctctgctcc cggaggaact gcacttcggc | 180 |

-continued

```
ggagttgaat gaatgaagag agcggagaag gagatctgac gggctggatc cccaaattgc    240
tttttaaaaa atatcttgga aactttgtcc tttgctgaat tacgacactg tccacctttta   300 atttcctcga aaactccaat cactcggctg aagccatgcc ttgtgttcag gcgcagtatg    360
ggtcctcgcc tcaaggagcc agcccgctt ctcagagcta cagttaccac tcttcgggag     420
aatacagctc cgatttctta actccagagt tgtcaagtt tagcatggac ctcaccaaca     480
ctgaaattac tgccaccact tctctcccca gcttcagtac ctttatggac aactacagca    540
caggctacga cgtcaagcca ccttgcttgt accaaatgcc cctgtccgga cagcagtcct    600
ccattaaggt agaagacatt cagatgcaca actaccagca cacagccac ctgcccctc      660 agtccgagga gatgatgcca cacagcgggt cggtttacta caagccctct tcgcccccga    720
cacccagcac cccgggcttc caggtacagc atagcccgat gtgggacgat ccgggctccc    780
ttcacaactt ccaccagaac tacgtggcca ctacgcatat gatcgagcag aggaagacac    840
ctgtctcccg cctttcactc ttctccttta agcagtcgcc cccgggcact cctgtgtcta    900
gctgccagat gcgctttgac gggcctctgc acgtccccat gaacccggag cccgcgggca    960 gccaccacg agtggatggg cagaccttcg ccgtgcccaa tcccattcgc aagccggcat    1020
ccatgggctt cccgggcctg cagatcggcc acgcgtcgca gttgcttgac acgcaggtgc   1080
cctcgccgcc gtcccggggc tctccctcca atgagggtct gtgcgctgtt tgcggtgaca   1140
acgcggcctg tcagcattac ggtgttcgca cttgtgaggg ctgcaaaggt ttctttaagc   1200
gcacggtgca aaaaaacgcg aaatatgtgt gtttagcaaa taaaaattgc ccagtggata   1260
agcgccgccg aaatcgttgt cagtactgtc ggtttcagaa gtgcctggct gttgggatgg   1320
ttaaagaagt ggttcgcacg gacagtttaa aaggccggag aggtcgtcta ccctcaaaac   1380
cgaagagccc acaggatccc tctccccct cacctccggt gagtctgatc agtgccctcg    1440
tcagagccca cgtcgactcc aatccggcaa tgaccagcct ggactattcc aggttccagg   1500
caaaccctga ctatcagatg agtggagatg atactcaaca tatccagcag ttctacgatc   1560
tcctgactgg ctctatggag atcatcagag ggtgggcaga aagattcct ggctttgctg    1620 acctgcccaa agccgatcag gacctgcttt ttgaatcagc tttcttagaa ttatttgttc   1680
tacgcttagc atacaggtcc aacccagtgg agggtaaact catcttttgc aatgggggtgg  1740 tcctgcacag gttgcaatgc gtgcgtggct ttggggaatg gattgattcc attgttgaat   1800
tctcctccaa cttgcagaat atgaacatcg acatttctgc cttctcctgc attgctgccc   1860
tggctatggt cacagagaga cacgggctca aggaacccaa gagagtggaa gagctacaaa   1920
acaaaattgt aaattgtctt aaagaccatg tgactttcaa taatgggggga ttgaaccgac   1980 ccaactacct gtccaaactg ttggggaagc tcccagaact tcgcacccctt tgcacacagg   2040 ggctccagcg cattttctac ctgaaattgg aagacttggt accaccacca gcaataattg   2100
acaaactttt cctggacacc ttacctttct aagactttct cccatgcacg tcaa           2154
```

<210> SEQ ID NO 67
<211> LENGTH: 9822
<212> TYPE: DNA
<213> ORGANISM: Mouse

<400> SEQUENCE: 67

```
gaattccaac acaatatgaa catttgggcc tgcagacttt tctcccgagg cttagttagc     60
ctaagtagta aatagctaag tgtgtgtgtg tgtgtgtgtg tgtgtgtgtg tgtgtgtgtg    120
tgtgtgtgtg tgtgtgaagc acgcgtgctt gtgtgtgtgt gtgggagatt gtctcttgaa    180
```

-continued

```
cattgtggag tcaggccccc tactgacaag atcagtcaat tgcagacctt gtctttgctc      240
ctgcagcttc gtcccttcca atcaagtgtg tgtgtgtggg ggggggggg ggcgggggaa       300 cgggacagcg gactgaggtt ttgatcatgg ccctttaaa ctttccgatg tgtgcaccta       360
gagcacatgc cagactccaa ccgtagaata gtcccagcca agaattactt taaatgagtt      420
tatgaatctt tcctcagtcg tagtaacatc cagggaagct gaacgcaaat ttgaaaagag      480
ggaaaactca cacttggatg aaaaaaagtc ttcacttcct ctcatttaca tattataatt      540
accctattct cacttactat tgtagtaaac tgctaagacc tctgccttt gatcttgggt       600 ataacaagcc ttgagcaaag gcttttctta tcaggaaacc aagcactgga ggttgctaaa      660
gaaaaaccct cgttactgtg cttgctcctt ggtgttcagt ataagaactc caggccctct      720
ttcctcactc taggagagca tttttaaaat gtccccagac tcaactcaac ctaaactgaa      780
tgtgttttta atgactcggg gagagaagct tgcagagggc aacatatcta cttagccgct      840
tttgtgtagg gaggtctgtg gctacgacct taaactcctg atacccgctc tcctggaact      900
gtattaaaaa ataataactt ccaccccagt gtcgctaagc ttgggtttcc gactgtctga      960
agatagctgc cgggaaacct ggcccaccgc gaggatcaag gaaagctcct ggtgaccgca     1020
ccctgctccc tcacggaagg ggaagggaac ccgggagggc gcctgtgagc tggagttgct     1080 tctatttgg gcccagcctg gccggtgcgt caatgcctgc gcccctgcgt caccgccacc     1140 cccaccccctt ccttctccat tgctctccaa actctcactt ttcccttc gttcgcgtgg      1200 aatcgctcct gcccacgggg cgctgacgct gccgagctca cactaataag ttgttttca     1260 ccctgccccc ctcttgcacc cccacttcct ggatctttt ttttttttt ttcctcgcgc      1320 ccactagggc accgctgagc cgtagcggca gcagctggag aggcagccgc aacatctggg    1380
ggaaacttaa ggtggtcacg taggtttccc ggaggccgat gcacagtgga gcccgcggct    1440
tgtctgggca gccgcaggc acccgatggc aacgcctctg cagccacagg ctcgctcagc    1500
ttggagctgg caaaggcgga ggtgcaggct aggaatgagc aaccccacaa ccccgagagt    1560
tccgcggtgt tctcccgggg tgttaggatc accgagaggg ggccgaggtg tatattgcac    1620
acacacacac acacacacac acacacacac acacacacac acacacacgc acgcgcgcac    1680
acacacacac acacacacac acacacacac acacacacac acacaccgct cgcccgggta    1740
gcttgggagc gagccaacgc tcgggagaag gggaggagga gcgctgtcct gggagaagaa    1800
ggggacccta caaagtcgct ctcccttggc ctcagtccct tcctggtctt gagagaaacc    1860
cgaagaggcc tgtctggcca gcttcacggg ggtactggga gtagggttag ccctctggag    1920
gatctgcgat tcctttgcta gaaagatcca gcgcgttggg aggaggggga gcggattgtc    1980
ttgcagagcg gagctggagg cgattgagag gaacgcgggg gtagggcacg ctcccacagt    2040
tcacccggac cctgggctgg ggcaatgggc acatactctc cgttttgggc gagacccacc    2100
ccgcctcgag ctccactccc cttgctgctt ctccctccat gctttcttct tggttgcagg    2160
cacgacagcc cctgcgtttc agaaacctgt gaaagggact gaagggcttg gtgggcacag    2220
cgaaatgtca actctgtcaa gagttgaccg agggcttgg gggcgatggt tcagatcacc    2280
tctgggctgg aggcgcacct gttgccggat cctttaatgt attgtctgcg agagaaagct    2340
ggcaacagtt cactcctact tgtggggtcc tctaagactt ggctcactgt ctaccctcct    2400
tcctcccaca ttgctttaga tagtacgtct ttttagtttc tgtaaagaag gggaaagggc    2460
ctgacctctc atccttcgaa gcgggaggaa gagtgggttt ttaaaaaggg agaaggggga    2520
```

```
tgcacggact aggggaatcc catctaacgc ccaagtctttt ggagagttac gagccacggg    2580
acaactgtct ccacttctgc taaagggtgt gaggagggta tgttggggag ctgcaaggca    2640
cacctctgcc ctctcggccc aggtgctagc tacctggccc acgcgagtgt tcttttccgt    2700
tcaagctttt gttgcaccct ccccacgtgt gaggacgcaa ggtctgggc ggggaggg      2760 caggtggagc gtagcatcac cacgacttc acggacctgg gttgcagaag tcacacttct    2820
ttcggaaaaa aaaaaatcca cccaagtggg ctaccaaggt gaaccgttcc caccttaaaa    2880
tcagccccag tcgtgacgtc aggtcggaaa tataccaaag cgagcgcggg ccaggagtcc    2940
ggggagcgcg gcggctcggc gattggaccg cgggccgctg acgcgggctg acgcgcgcag    3000
actttaggtg catgttggca gcagcagctc gagccacata acaaaggca cattggcggc    3060 cagggccagt ccgccccgcg gctccgcaca gctccgcgtc cctctctccg gccccgctgg    3120
ctgcctccct ctcctgcggc cgggctggct gcgtgtggct ctccgcgccc cgcttccgca    3180
gcgctcccgc ggaccgggc tcctctgctc ccggagggaa ctgcacttcg gcggagttga    3240
atgaatgaag agagcggaca agtgagtagc tgcggcgggg ccgcccgcgg tcacgcgtcc    3300
tcccggtctc cgcgtaccag gggaacgggt tctctgcaag tggtcgcccg agccgcggag    3360
cgcgaagggg ctggggaagg gggatggcga gtgggcgcgc gcagctccgc cgagcctctg    3420
ctggaactcc ggtgctagcg taaaggggg ggagttggct gccggcagag gtttccaggc    3480
ttctcattgg tggatgtggc aagggactc ccacagtttt aggagaagcg gacttgccgg    3540
tggagatgtg cgcaaagttt gctcttggtg tgaaattgat tgtggcttga ggaggctcca    3600
tctcgcgaac atgtgggaaa cagtccggga gagaaagttt acgtgttgct gggaacagt    3660 gtcgctcggc tcgcccgctg gtggaggttt cccggatatc gtcgagtaag ggtagtgtcg    3720
gtagagggtc ctgtagcgaa gttgcctgaa atgactggtt ttgatatatg ttgtccttgg    3780
atagtgtgtc agtgtgtgcg tgaggtaaag aatacggtta tgaaactgtg acatagccac    3840
gggttaatat ccagaacaga catattttca agggcggcgg cggatggggg tggggagata    3900
aagcaaaagt cctctggttt gtcttgttaa ccttctccgc tcctgaagca agcaagatt    3960 gtggaagaag tggggggggg gggcggagag gggagggagc aaaggagagg gtgttcaggt    4020
ttctttactt tatcaacaag atcgtctatg ctgtagaatg ccttgcaagt gggaacatct    4080
gaaaaaaaaa aatacctagg acacaagaat cggttgtccc agcaagtagg cagcctgtgg    4140
aaagcattgt ggagaaggtg tccagttttcc tgttctgaga agtgcttcta actttggtgc    4200
caatatcata tgcgtaacat ttcttttccct ctgcagttga cccaagatac tcctggtaaa    4260
gtagagatct ctctcatcac ctctgggcca ttaaagatgt tgaaaatcca gttctctgga    4320
ggaacaccaa ttcgcttgtc ccttaagatc ctgtgttgaa cccaaagcaa ttactaaagc    4380
tacacacttg ctcccacatt ggctgtttgg ttgtccaggc cttgctaacg tttcctaagg    4440
gttggatctg tatttttttt tttcacggtt tactctcgag ttcttttaac tttctttctc    4500
cttctaagag aaaagtccac tggactctaa gagagatatt aagaggaagc tttgatgctg    4560 tgttttttcct ttacccagac ttcttaggtt tgacataaag tagaatgaca aaggcccttc    4620
catctacagc aaaggggcca attcattata ttgatcagta tctggtagac tcatgggata    4680
atttccccac aggatgcttt tctgcaggg attacactgg gagatgagcg gcattatctg    4740
ctgtttagcc accttgtctc tgcacatttc attttaagat gctgttgggt aaagtcttca    4800
cactcatttc caaggaagca cttgaagggc ctgctgagtg agtctgcatc tgcccagccc    4860
aagtctcggt gggaagacat cctgaaactt cctgtgtctg tatttcaggg agatctgacg    4920
```

```
ggctggattc  ccaatagctc  tttttttaaaa  tcttggaaac  tttgtccttc  gctgaattac      4980
gacactgtcc  acctttaatt  tcctcgaaaa  ctccaataac  tctgctgaag  gtcagtgagc      5040
tttatctttc  attaccttc   ctgagttccc  ccatacctc   agaaaaacaa  aacaaaacag      5100
ggcaacagga  tctttccagg  ccaaccctgt  gcctatagtc  acagaggaca  actttcttat      5160
tgtgcaattc  aactcatttc  tagagcatgg  cttctagaaa  tccgtcgacc  ctgagcttca      5220
aagaagaagc  tcatcagagt  gggactgtct  gcgggaaggg  ggtggagcgc  ggggggggg       5280 gcgtttggaa  atgagtgtag  accctcaaca  gctttccagc  tctgggtcgt  cccgggatca      5340
gccctttcct  ttcttcatcg  ctgttccacc  tcttttgccc  ttcccctgc   atccctaaac      5400 ccccatcctc  tccccgcctc  cctccacccc  caacccgacg  ccgcgggctg  ccggtgtagc      5460
cccgggtgta  gaccgagccc  ggaagaaagt  gttcagttga  ccaggctgag  tgtatatcac      5520
cctgtttcgt  ttccagccat  gccttgtgtt  caggcgcagt  atgggtcctc  gcctcaagga      5580
gccagccccg  cttctcagag  ctacagttac  cactcttcgg  gagaatacag  ctccgatttc      5640
ttaactccag  agtttgtcaa  gtttagcatg  gacctcacca  acactgaaat  tactgccacc      5700
acttctctcc  ccagcttcag  tacctttatg  gacaactaca  gcacaggcta  cgacgtcaag      5760
ccaccttgct  tgtaccaaat  gcccctgtcc  ggacagcagt  cctccattaa  ggtagaagac      5820
attcagatgc  acaactacca  gcaacacagc  cacctgcccc  ctcagtccga  ggagatgatg      5880
ccacacagcg  ggtcggttta  ctacaagccc  tcttcgcccc  cgacacccag  caccccgagc      5940
ttccaggtgc  agcatagccc  gatgtgggac  gatccgggct  cccttcacaa  cttccaccag      6000
aactacgtgg  ccactacgca  tatgatcgag  cagaggaaga  cacctgtctc  ccgcctgtca      6060
ctcttctcct  ttaagcagtc  gccccgggc   actcctgtgt  ctagctgcca  gatgcgcttc      6120
gacgggcctc  tgcacgtccc  catgaacccg  gagcccgcgg  gcagccacca  cgtagtggat      6180
gggcagacct  tcgccgtgcc  caaccccatt  cgcaagccgg  catccatggg  cttcccgggc      6240
ctgcagatcg  gccacgcatc  gcagttgctt  gacacgcagg  tgccctcgcc  gccgtcccgg      6300
ggctctccct  ccaatgaggg  tctgtgcgct  gtttgcggtg  acaacgcggc  ctgtcagcac      6360
tacggtgttc  gcacttgtga  gggctgcaaa  ggtttcttta  aggtgagcaa  gacagggcgg      6420
aggtggcagg  tagcggtcct  tatacctgag  acccagcagt  gtaccctcac  ttccggtcgg      6480
cagccccgct  cgagttccct  gcagctactc  acaggctgtg  gaagaggctt  tggggtgtc       6540 taaggaaaga  aatcagaaag  actggtagag  tcagggtttc  atccccccgc  ccccgcgcc      6600 ccacagcaac  ctgcggcccc  ggcctccagc  ccgaaattgc  tggagccaga  gttggaagag      6660
ggctattgca  tgtgttaggc  gctgtcttcc  ttgttcagat  tgaaattggt  taggacagag      6720
aaccgtgtct  gagctaacca  agtggaacag  aattccctat  ggtcaaatta  gtgatctctt      6780
tatttcgcca  tcctgattga  ataatcttat  catttttaaat agagaaggtc  tccaaggaat      6840
gtaaataata  tgaatgccca  cggatttgta  tttactgagc  gtctcctgcc  ccttctcctg      6900
gcatataaaa  cacagcaagg  agcggtaagg  ttagctcaaa  tgttaacgct  atcaattttc      6960
ttctggtaaa  tgccctgggg  aggaaaagga  aggaaatag   gaagaaaaga  aaagaaaag       7020 gaaagaaaga  aagaaagaaa  gaaagaaaga  agaaagaaa   gaaagaaaga  aagaagaaa       7080 ttgaaggagt  agtgtttatg  tttgtaggga  aggaatgcag  atccaagcca  tttttttaaaa     7140 aaatgtgtcc  agtttgctgg  actttgagtg  aaaaaataat  catttggggc  cctacattct      7200
ctccctctac  agcgcacggt  gcaaaaaaac  gcgaaatatg  tgtgtttagc  aaataaaaac      7260
```

```
tgcccagtgg acaagcgccg ccgaaatcgt tgtcagtact gtcggtttca gaagtgccta   7320
gctgttggga tggttaaaga aggtaggtcg aggcaagttg ttgaccttcc atttcacgcc   7380
cctgaaagtc caccagctgc ttgtggactc cggtccctgc cttactcccc acgcccttga   7440
ctccaggatt ccactgctaa atgccctcct ctaaagaaag ccccccggcc ctccttttct   7500
ttaagtatag gacccagttg gaggaagta taaaataacc cgccatttat taatgcttct   7560
cgtcagtaaa gtctttaaaa tcagaggagc cctggaccac caggttgggc ttcttccact   7620
gttccctcgg ggaggaggcc gtgagacagc tgagtctggg ctcaagggaa cagcgttaac   7680
ccttgagtaa ttccttttaca gtggttcgca cggacagttt aaaaggccgg agaggtcgtt   7740
taccctcgaa gccgaagagc ccacaggatc cctctccccc ctcacctccg gtgagtctga   7800
tcagtgccct cgtcagagcc cacgtcgatt ccaatccggc aatgaccagc ctggactatt   7860
ccagggtaag aagccggtgg tgggggaata tcaatcatgt ggacaagcca ataaatgggc   7920
aggaccctct ccctataccc agctttagca ccccccaaact caagggtaaa ggaggaacag   7980
cagaatacat acttcacaac tttgggcagg ttttcaggag acaggtggtg ctgctcaaag   8040
tacagaccgg agaacacacc ggaggggttg aatctttgtg aaccattatt gtccgacagt   8100
ccctccagct gcggtctgga aggcaaaacc tagacagtct agccttcctt cccaagtcta   8160
ctttacgaag ttactagaat acattcccct cccccttgac ttgtctgggg ccagggagtg   8220
aaagaggggg tggaagggat gtcaatgggg gggggggttg tccccgggtc agggatcaag   8280
tggtgcaatt cttcttttac tccagctgtg aaaatgtgca ggctttgggc agagggagtg   8340
tgcccaaacc tagtagcgac tgcaatatta ttaagctttc caaaaggcgc ctccgtgcaa   8400
gacccactct gggattagca tgaatactac cgtgtcaatt gttttgtggc gataagactg   8460
aacgtttccc agggctggat ggcactgtat ttagtctgta tggaaatggt aatttacata   8520
tttaaagcag cgacctcata gcaccgtccc taattgaatt aattgccccg gaagcatcta   8580
atttccttac tggtcagaga gaggtttaat tgttataaaa acctggctcc cctactagaa   8640
acggggttag caatttcacg ggttatatat tttagagaac ctcattaagt gcttttttaaa   8700 atgaaattcc agttccaggc aaaccctgac tatcagatga gtggagatga tacccaacat   8760
atccagcagt tctacgatct cctgaccggc tctatggaga tcatcagagg gtgggcagag   8820
aagatccctg gctttgctga cctgcccaaa gccgaccagg acctgctttt tgaatcagct   8880
ttcttagaat tatttgttct gcgcttagca tacaggtaat gaatgaggcc tggaggaggg   8940
atcagaagta aggaaagga agagaaaagg gttgggttg gaggcaagat aaaaacaaag   9000
caaaggtgaa gaagggaagg agtgagccca gagccttggg tgaccggagt ggtggtggga   9060 tagggagtt cttgattgtt atgaaattaa acccctttcaa ggtccactgg tctacatttt   9120
attaactctt cagtaattag gtgcctctta aatccctcat ttattgctct tcaagtaatt   9180
agttgtttag cttctctctc tctcttttc tcccctctct ctttggtatt aattgcaggt   9240
ccaacccagt ggagggtaaa ctcatctttt gcaatgggt ggtcttgcac aggttgcaat   9300
gcgtgcgtgg ctttggggaa tggattgatt ccattgttga attctcctcc aacttgcaga   9360
atatgaacat cgacatttct gccttctcct gcattgctgc cctggctatg gtcacaggtc   9420
agtactgctg gtgcaggaca cttccccttc cgaacttcct ctggtgggac cggtcatggc   9480
tttccctaat cgcagattct ttctgattct gccatctgac taactcccct ctgcattctt   9540
ttgtttctgg ttgcatttc tgcagagaga cacgggctca aggaacccaa gagagtggaa   9600
gagctacaaa acaaaattgt aaattgtctt aaagaccatg tgactttcaa taatgggggt   9660
```

-continued

| | |
|---|---|
| ttgaaccgac ccaactacct gtctaaactg ttggggaagc tgccagaact ccgcacccctt | 9720 |
| tgcacacagg gcctccagcg cattttctac ctgaaattgg aagacttggt accaccacca | 9780 |
| gcaataattg acaaactttt cctggacacc ttacctttct aa | 9822 |

<210> SEQ ID NO 68
<211> LENGTH: 820
<212> TYPE: DNA
<213> ORGANISM: Mouse

<400> SEQUENCE: 68

| | |
|---|---|
| aaagttaccg aagccacgga caactgtctc cacttctgct aaagggtgtg aggagggtat | 60 |
| gttggggagc tgcaaggcac acctctgccc tctcggccca ggtgctagct acctggccca | 120 |
| cgcgagtgtt cttttccgtt caagcttttg ttgcaccctc cccacgtgtg aggacgcaag | 180 |
| gtctggggac gtgggggagg ggcaggtgga gcgtagcatc accacggact tcacggacct | 240 |
| gggttgcaga agtcacactt ctttcggaaa aaaaaaaatc cacccaagtg ggctaccaag | 300 |
| gtgaaccgtt cccaccttaa aatcagcccc agtcgtgacg tcaggtcgga aatataccaa | 360 |
| agcgagcgcg ggccaggagt ccggggagcg cggcggctcg gcgattggac cgcgggctga | 420 |
| cgcggctgac gcgcgcagac tttaggtgca tgttggcagc agcagctcga gccacataaa | 480 |
| caaggcacat tggcgccagg gccagtacgc cccgccgtgg cgcacagctc cgcgtccctc | 540 |
| tctccggccc cgctggcttg cctccctctc ctgcggccgg gctggctgcg tgtggctctc | 600 |
| cgcgccccgc ttccgcagcg ctcccgcgga cccgggctcc tctgctcccg gagggaactg | 660 |
| cacttcggcg gagttgaatg aatgaagaga gcggacaagg agatctgacg ggctggattc | 720 |
| ccaatagctc ttttttaaaa tcttggaaac tttgtccttc gctgaattac gacactgtcc | 780 |
| acctttaatt tcctcgaaaa ctccaataac tctgctgaag | 820 |

<210> SEQ ID NO 69
<211> LENGTH: 125
<212> TYPE: DNA
<213> ORGANISM: Zebrafish

<400> SEQUENCE: 69

| | |
|---|---|
| gtacaaaagg gttcgaagta tgtgtgttta gccaataaaa actgtcctgt ggataaacgt | 60 |
| cggagaaaca gatgtcagta ttgcagattt cagaagtgcc tggtggtcgg catggtcaaa | 120 |
| gaaat | 125 |

<210> SEQ ID NO 70
<211> LENGTH: 125
<212> TYPE: DNA
<213> ORGANISM: Sea lamprey

<400> SEQUENCE: 70

| | |
|---|---|
| gtgcagaagg gttcgaaata cgtgtgtctc gccaacaaga actgtcccat cgacaagcgc | 60 |
| cgccggaacc gctgccagta ctgtcgcttt cagaagtgtc tcgtggtcgg catggtcaaa | 120 |
| gaagt | 125 |

<210> SEQ ID NO 71
<211> LENGTH: 2247
<212> TYPE: DNA
<213> ORGANISM: Mouse

<400> SEQUENCE: 71

```
ggcacgaggg ccagggccag tccgccccgc ggctccgcac agctccgcgt ccctctctcc      60
ggccccgctg gctgcctccc tctcctgcgg ccgggctggc tgcgtgtggc tctccgcgcc     120
ccgcttccgc agcgctcccg cggacccggg ctcctctgct cccggaggga actgcacttc     180
ggcggagttg aatgaatgaa gagagcggac aaggagatct gacgggctgg attcccaata     240
gctctttttt aaaatcttgg aaactttgtc cttcgctgaa ttacgacact gtccaccttt     300
aatttcctcg aaaactccaa taactctgct gaagccatgc cttgtgttca ggcgcagtat     360
gggtcctcgc ctcaaggagc cagccccgct tctcagagct acagttacca ctcttcggga     420
gaatacagct ccgatttctt aactccagag tttgtcaagt ttagcatgga cctcaccaac     480
actgaaatta ctgccaccac ttctctcccc agcttcagta cctttatgga caactacagc     540
acaggctacg acgtcaagcc accttgcttg taccaaatgc ccctgtccgg acagcagtcc     600
tccattaagg tagaagacat tcagatgcac aactaccagc aacacagcca cctgccccct     660
cagtccgagg agatgatgcc acacagcggg tcggtttact acaagccctc ttcgcccccg     720
acacccagca ccccgagctt ccaggtgcag catagcccga tgtgggacga tccgggctcc     780
cttcacaact tccaccagaa ctacgtggcc actacgcata tgatcgagca gaggaagaca     840
cctgtctccc gcctgtcact cttctccttt aagcagtcgc ccccgggcac tcctgtgtct     900
agctgccaga tgcgcttcga cgggcctctg cacgtcccca tgaacccgga gcccgcgggc     960
agccaccacg tagtggatgg gcagaccttc gccgtgccca cccccattcg caagccggca    1020
tccatgggct tccgggcct gcagatcggc cacgcatcgc agttgcttga cacgcaggtg    1080
ccctcgccgc cgtcccgggg ctctccctcc aatgagggtc tgtgcgctgt ttgcggtgac    1140
aacgcggcct gtcagcacta cggtgttcgc acttgtgagg gctgcaaagg tttctttaag    1200
cgcacggtgc aaaaaaacgc gaaatatgtg tgtttagcaa ataaaaactg cccagtggac    1260
aagcgccgcc gaaatcgttg tcagtactgt cggtttcaga agtgcctagc tgttgggatg    1320
gttaaagaag tggttcgcac ggacagttta aaaggccgga gaggtcgttt accctcgaag    1380
ccgaagagcc cacaggatcc ctctccccc tcacctccgg tgagtctgat cagtgccctc    1440
gtcagagccc acgtcgattc caatccggca atgaccagcc tggactattc caggttccag    1500
gcaaaccctg actatcagat gagtggagat gatacccaac atatccagca gttctacgat    1560
ctcctgaccg gctctatgga gatcatcaga gggtgggcag agaagatccc tggctttgct    1620
gacctgccca agccgaccga ggacctgctt tttgaatcag ctttcttaga attatttgtt    1680
ctgcgcttag catacaggtc caacccagtg gagggtaaac tcatcttttg caatggggtg    1740
gtcttgcaca ggttgcaatg cgtgcgtggc tttgggggaat ggattgattc cattgttgaa    1800
ttctcctcca acttgcagaa tatgaacatc gacatttctg ccttctcctg cattgctgcc    1860
ctggctatgg tcacagagag acacgggctc aaggaaccca agagagtgga agagctacaa    1920
aacaaaattg taaattgtct taaagaccat gtgactttca ataatggggg tttgaaccga    1980
cccaactacc tgtctaaact gttggggaag ctgccagaac tccgcaccct ttgcacacag    2040
ggcctccagc gcatttttcta cctgaaattg aagacttgg taccaccacc agcaataatt    2100
gacaaacttt tcctggacac cttacctttc taagaccttc tcccaagcac gtcaaagaac    2160
tggaaagaaa aaaaaaataa catccagagg gggctggtca catgggcaga gagctggttg    2220
aagtgtccag ttcaccttat ctcccctt                                       2247
```

<210> SEQ ID NO 72
<211> LENGTH: 436

```
<212> TYPE: DNA
<213> ORGANISM: Human

<400> SEQUENCE: 72
tttaaaaggc cggagaggtc gtttgccctc gaaaccgaag agcccacagg agccctctcc    60
cccttcgccc ccggtgagtc tgatcagtgc cctcgtcagg gcccatgtcg actccaaccc   120
ggctatgacc agcctggact attccaggtt ccaggcgaac cctgactatc aaatgagtgg   180
agatgacacc cagcatatcc agcaattcta tgatctcctg actggctcca tggagatcat   240
ccggggctgg gcagagaaga tccctgggct tcgcagacct gcccaaagcc gaccaagacc   300
tgcttttga atcagctttc ttaggaactg tttgtccttc gattaggcat acaggtccaa    360
cccagtggga ggggtaaact tcattctttt tgcaatgggg gtgggtcttt gcacaggttt   420
gcaatgcgtt tcgtgg                                                   436

<210> SEQ ID NO 73
<211> LENGTH: 406
<212> TYPE: DNA
<213> ORGANISM: Human
<220> FEATURE:
<221> NAME/KEY: misc_feature
<222> LOCATION: (1)..(406)
<223> OTHER INFORMATION: n = unknown

<400> SEQUENCE: 73
tgactatcaa atgagtggag atgacaccca gcatatccag caattctatg atctcctgac    60
tggctccatg gagatcatcc ggggctgggc agagaagatc cctggcttcg cagacctgcc   120
caaagccgac caagacctgc tttttgaatc agctttctta gaactgtttg tccttcgatt   180
agcatacagg tccaacccag tgagggtaa actcatcttt tgcaatgggg tggtcttgca    240
caggttgcaa tgcgttcgtg gctttgggga tggattgat tccattgttg aattctcctc    300
caactttgca gaatatgaac atcgacattt ctggccttct cctgcatttg cttgccctgg    360
ntatggtcac agagagacac gggcttaagg aacccnagag agttgg                  406

<210> SEQ ID NO 74
<211> LENGTH: 598
<212> TYPE: PRT
<213> ORGANISM: Mouse

<400> SEQUENCE: 74

Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
                20                  25                  30

Asp Phe Leu Thr Pro Glu Phe Val Lys Phe Ser Met Asp Leu Thr Asn
            35                  40                  45

Thr Glu Ile Thr Ala Thr Thr Ser Leu Pro Ser Phe Ser Thr Phe Met
        50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125
```

-continued

```
Thr Pro Ser Thr Pro Ser Phe Gln Val Gln His Ser Pro Met Trp Asp
    130                 135                 140
Asp Pro Gly Ser Leu His Asn Phe His Gln Asn Tyr Val Ala Thr Thr
145                 150                 155                 160
His Met Ile Glu Gln Arg Lys Thr Pro Val Ser Arg Leu Ser Leu Phe
                165                 170                 175
Ser Phe Lys Gln Ser Pro Pro Gly Thr Pro Val Ser Ser Cys Gln Met
            180                 185                 190
Arg Phe Asp Gly Pro Leu His Val Pro Met Asn Pro Glu Pro Ala Gly
        195                 200                 205
Ser His His Val Val Asp Gly Gln Thr Phe Ala Val Pro Asn Pro Ile
    210                 215                 220
Arg Lys Pro Ala Ser Met Gly Phe Pro Gly Leu Gln Ile Gly His Ala
225                 230                 235                 240
Ser Gln Leu Leu Asp Thr Gln Val Pro Ser Pro Pro Ser Arg Gly Ser
                245                 250                 255
Pro Ser Asn Glu Gly Leu Cys Ala Val Cys Gly Asp Asn Ala Ala Cys
            260                 265                 270
Gln His Tyr Gly Val Arg Thr Cys Glu Gly Cys Lys Gly Phe Phe Lys
        275                 280                 285
Arg Thr Val Gln Lys Asn Ala Lys Tyr Val Cys Leu Ala Asn Lys Asn
    290                 295                 300
Cys Pro Val Asp Lys Arg Arg Arg Asn Arg Cys Gln Tyr Cys Arg Phe
305                 310                 315                 320
Gln Lys Cys Leu Ala Val Gly Met Val Lys Glu Val Val Arg Thr Asp
                325                 330                 335
Ser Leu Lys Gly Arg Arg Gly Arg Leu Pro Ser Lys Pro Lys Ser Pro
            340                 345                 350
Gln Asp Pro Ser Pro Pro Ser Pro Val Ser Leu Ile Ser Ala Leu
        355                 360                 365
Val Arg Ala His Val Asp Ser Asn Pro Ala Met Thr Ser Leu Asp Tyr
    370                 375                 380
Ser Arg Phe Gln Ala Asn Pro Asp Tyr Gln Met Ser Gly Asp Asp Thr
385                 390                 395                 400
Gln His Ile Gln Gln Phe Tyr Asp Leu Leu Thr Gly Ser Met Glu Ile
                405                 410                 415
Ile Arg Gly Trp Ala Glu Lys Ile Pro Gly Phe Ala Asp Leu Pro Lys
            420                 425                 430
Ala Asp Gln Asp Leu Leu Phe Glu Ser Ala Phe Leu Glu Leu Phe Val
        435                 440                 445
Leu Arg Leu Ala Tyr Arg Ser Asn Pro Val Glu Gly Lys Leu Ile Phe
    450                 455                 460
Cys Asn Gly Val Val Leu His Arg Leu Gln Cys Val Arg Gly Phe Gly
465                 470                 475                 480
Glu Trp Ile Asp Ser Ile Val Glu Phe Ser Ser Asn Leu Gln Asn Met
                485                 490                 495
Asn Ile Asp Ile Ser Ala Phe Ser Cys Ile Ala Ala Leu Ala Met Val
            500                 505                 510
Thr Glu Arg His Gly Leu Lys Glu Pro Lys Arg Val Glu Glu Leu Gln
        515                 520                 525
Asn Lys Ile Val Asn Cys Leu Lys Asp His Val Thr Phe Asn Asn Gly
    530                 535                 540
Gly Leu Asn Arg Pro Asn Tyr Leu Ser Lys Leu Leu Gly Lys Leu Pro
```

```
                545                 550                 555                 560
Glu Leu Arg Thr Leu Cys Thr Gln Gly Leu Gln Arg Ile Phe Tyr Leu
                565                 570                 575
Lys Leu Glu Asp Leu Val Pro Pro Ala Ile Ile Asp Lys Leu Phe
                580                 585                 590
Leu Asp Thr Leu Pro Phe
            595

<210> SEQ ID NO 75
<211> LENGTH: 598
<212> TYPE: PRT
<213> ORGANISM: Human

<400> SEQUENCE: 75

Met Pro Cys Val Gln Ala Gln Tyr Gly Ser Ser Pro Gln Gly Ala Ser
1               5                   10                  15
Pro Ala Ser Gln Ser Tyr Ser Tyr His Ser Ser Gly Glu Tyr Ser Ser
                20                  25                  30
Asp Phe Leu Thr Pro Glu Phe Val Lys Phe Ser Met Asp Leu Thr Asn
            35                  40                  45
Thr Glu Ile Thr Ala Thr Thr Ser Leu Pro Ser Phe Ser Thr Phe Met
    50                  55                  60
Asp Asn Tyr Ser Thr Gly Tyr Asp Val Lys Pro Pro Cys Leu Tyr Gln
65                  70                  75                  80
Met Pro Leu Ser Gly Gln Gln Ser Ser Ile Lys Val Glu Asp Ile Gln
                85                  90                  95
Met His Asn Tyr Gln Gln His Ser His Leu Pro Pro Gln Ser Glu Glu
            100                 105                 110
Met Met Pro His Ser Gly Ser Val Tyr Tyr Lys Pro Ser Ser Pro Pro
    115                 120                 125
Thr Pro Thr Thr Pro Gly Phe Gln Val Gln His Ser Pro Met Trp Asp
130                 135                 140
Asp Pro Gly Ser Leu His Asn Phe His Gln Asn Tyr Val Ala Thr Thr
145                 150                 155                 160
His Met Ile Glu Gln Arg Lys Thr Pro Val Ser Arg Leu Ser Leu Phe
                165                 170                 175
Ser Phe Lys Gln Ser Pro Pro Gly Thr Pro Val Ser Ser Cys Gln Met
            180                 185                 190
Arg Phe Asp Gly Pro Leu His Val Pro Met Asn Pro Glu Pro Ala Gly
    195                 200                 205
Ser His His Val Val Asp Gly Gln Thr Phe Ala Val Pro Asn Pro Ile
210                 215                 220
Arg Lys Pro Ala Ser Met Gly Phe Pro Gly Leu Gln Ile Gly His Ala
225                 230                 235                 240
Ser Gln Leu Leu Asp Thr Gln Val Pro Ser Pro Pro Ser Arg Gly Ser
                245                 250                 255
Pro Ser Asn Glu Gly Leu Cys Ala Val Cys Gly Asp Asn Ala Ala Cys
            260                 265                 270
Gln His Tyr Gly Val Arg Thr Cys Glu Gly Cys Lys Gly Phe Phe Lys
    275                 280                 285
Arg Thr Val Gln Lys Asn Ala Lys Tyr Val Cys Leu Ala Asn Lys Asn
        290                 295                 300
Cys Pro Val Asp Lys Arg Arg Arg Asn Arg Cys Gln Tyr Cys Arg Phe
305                 310                 315                 320
```

```
Gln Lys Cys Leu Ala Val Gly Met Val Lys Glu Val Val Arg Thr Asp
                325                 330                 335

Ser Leu Lys Gly Arg Arg Gly Arg Leu Pro Ser Lys Pro Lys Ser Pro
            340                 345                 350

Gln Glu Pro Ser Pro Ser Pro Pro Val Ser Leu Ile Ser Ala Leu
        355                 360                 365

Val Arg Ala His Val Asp Ser Asn Pro Ala Met Thr Ser Leu Asp Tyr
    370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
        435                 440                 445

Leu Arg Leu Ala Tyr Arg Ser Asn Pro Val Glu Gly Lys Leu Ile Phe
    450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Leu Ala Met Val
            500                 505                 510

Thr Glu Arg His Gly Leu Lys Glu Pro Lys Arg Val Glu Glu Leu Gln
        515                 520                 525

Asn Lys Ile Val Asn Cys Leu Lys Asp His Val Thr Phe Asn Asn Gly
    530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Ala Ile Ile Asp Lys Leu Phe
            580                 585                 590

Leu Asp Thr Leu Pro Phe
        595

<210> SEQ ID NO 76
<211> LENGTH: 600
<212> TYPE: PRT
<213> ORGANISM: Oryzias latipes

<400> SEQUENCE: 76

Met Pro Cys Val Gln Ala Gln Tyr Gly Ser Ser Pro Gln Gly Ala Ser
1               5                   10                  15

Pro Ala Ser Gln Ser Tyr Ser Tyr His Thr Ala Gly Glu Tyr Ser Cys
            20                  25                  30

Asp Phe Leu Thr Pro Glu Phe Val Lys Phe Ser Met Asp Leu Thr Asn
        35                  40                  45

Thr Glu Ile Thr Ala Thr Thr Ser Leu Pro Ser Phe Ser Thr Phe Met
    50                  55                  60

Asp Asn Tyr Asn Thr Gly Tyr Asp Val Lys Pro Pro Cys Leu Tyr Gln
65                  70                  75                  80

Met Pro His Ser Gly Glu Gln Ser Ser Ile Lys Val Glu Asp Val Gln
                85                  90                  95
```

```
Met His Ser Tyr His Gln Gln Ser His Leu Pro Pro Gln Ser Glu Glu
            100                 105                 110

Met Ile Ala His Thr Gly Pro Met Tyr Phe Lys Pro Ser Ser Pro His
            115                 120                 125

Ala Pro Ser Thr Pro Asn Phe Gln Val Gln Pro Asn His Met Trp Glu
            130                 135                 140

Asp Pro Gly Ser Leu His Ser Phe His Gln Asn Tyr Val Ala Ala Thr
145                 150                 155                 160

Ser His Met Met Glu Gln Arg Lys Thr Pro Val Ser Arg Leu Ser Leu
                165                 170                 175

Phe Ser Phe Lys Gln Ser Pro Pro Gly Thr Pro Val Ser Ser Cys Gln
            180                 185                 190

Met Arg Phe Asp Gly Pro Leu His Val Ser Met Thr His Asp Asn Pro
            195                 200                 205

Gly Ala His Arg Gly Leu Asp Gly Gln Ser Phe Ala Val Pro Ser Ala
            210                 215                 220

Ile Arg Lys Gln Ala Gly Leu Ala Phe Pro His Ser Leu Gln Leu Ser
225                 230                 235                 240

His Gly His Gln Leu Val Asp Ser Gln Val Pro Ser Pro Pro Ser Arg
                245                 250                 255

Gly Ser Pro Ser Asn Glu Gly Leu Cys Ala Val Cys Gly Asp Asn Ala
            260                 265                 270

Ala Cys Gln His Tyr Gly Val Arg Thr Cys Glu Gly Cys Lys Gly Phe
            275                 280                 285

Phe Lys Arg Thr Val Gln Lys Asn Ala Lys Tyr Val Cys Leu Ala Asn
            290                 295                 300

Lys Asn Cys Pro Val Asp Lys Arg Arg Arg Asn Arg Cys Gln Phe Cys
305                 310                 315                 320

Arg Phe Gln Lys Cys Leu Val Val Gly Met Val Arg Glu Val Val Arg
                325                 330                 335

Thr Asp Asn Leu Lys Gly Arg Arg Gly Arg Leu Pro Ser Lys Pro Lys
            340                 345                 350

Ser Pro Gln Glu Pro Ser Pro Pro Ser Pro Val Ser Leu Ile Ser
            355                 360                 365

Ala Leu Val Arg Ala His Val Asp Ser Asn Pro Ser Met Ser Ala Leu
            370                 375                 380

Asp Tyr Ser Arg Phe Gln Ala Asn Pro Asp Tyr Gln Met Thr Gly Asp
385                 390                 395                 400

Asn Thr Gln His Ile Gln Gln Phe Tyr Asp Leu Leu Thr Gly Ser Met
            405                 410                 415

Glu Ile Ile Arg Gly Trp Ala Glu Lys Ile Pro Gly Phe Ser Asp Leu
            420                 425                 430

Pro Lys Gln Asp Gln Asp Leu Leu Phe Glu Ser Ala Phe Leu Glu Leu
            435                 440                 445

Phe Val Leu Arg Leu Ala Tyr Arg Ser Asn Pro Val Glu Gly Lys Leu
            450                 455                 460

Ile Phe Cys Asn Gly Val Val Leu His Arg Leu Gln Cys Val Arg Gly
465                 470                 475                 480

Phe Gly Glu Trp Val Asp Ala Ile Val Glu Phe Ser Ser Asn Leu Gln
                485                 490                 495

Ser Leu Asp Ile Asp Ile Ser Ala Phe Ser Cys Ile Ala Ala Leu Ala
            500                 505                 510
```

-continued

```
Met Val Thr Glu Arg His Gly Leu Lys Glu Pro Lys Arg Val Glu Asp
            515                 520                 525

Leu Gln Asn Lys Ile Val Asn Cys Leu Lys Asp Gln Val Thr Phe Asn
        530                 535                 540

Ser Gly Gly Leu Asn Arg Pro Asn Tyr Leu Ser Lys Leu Leu Gly Lys
545                 550                 555                 560

Leu Pro Glu Leu Arg Thr Leu Cys Thr Gln Gly Leu Gln Arg Ile Phe
                565                 570                 575

Tyr Leu Lys Leu Glu Asp Leu Val Pro Pro Ala Ile Ile Asp Lys
                580                 585                 590

Leu Phe Leu Asp Thr Leu Pro Phe
            595                 600
```

<210> SEQ ID NO 77
<211> LENGTH: 598
<212> TYPE: PRT
<213> ORGANISM: Mouse

<400> SEQUENCE: 77

```
Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
                20                  25                  30

Asp Phe Leu Thr Pro Glu Phe Val Lys Phe Ser Met Asp Leu Thr Asn
            35                  40                  45

Thr Glu Ile Thr Ala Thr Thr Ser Leu Pro Ser Phe Ser Thr Phe Met
        50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125

Thr Pro Ser Thr Pro Ser Phe Gln Val Gln His Ser Pro Met Trp Asp
130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
        195                 200                 205

Ser His His Val Val Asp Gly Gln Thr Phe Ala Val Pro Asn Pro Ile
    210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Ser Arg Gly Ser
                245                 250                 255

Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
        275                 280                 285
```

-continued

```
Arg Thr Val Gln Lys Asn Ala Lys Tyr Val Cys Leu Ala Asn Lys Asn
    290                 295                 300
Cys Pro Val Asp Lys Arg Arg Asn Arg Cys Gln Tyr Cys Arg Phe
305                 310                 315                 320
Gln Lys Cys Leu Ala Val Gly Met Val Lys Glu Val Val Arg Thr Asp
                325                 330                 335
Ser Leu Lys Gly Arg Arg Gly Arg Leu Pro Ser Lys Pro Lys Ser Pro
            340                 345                 350
Gln Asp Pro Ser Pro Ser Pro Val Ser Leu Ile Ser Ala Leu
        355                 360                 365
Val Arg Ala His Val Asp Ser Asn Pro Ala Met Thr Ser Leu Asp Tyr
    370                 375                 380
Ser Arg Phe Gln Ala Asn Pro Asp Tyr Gln Met Ser Gly Asp Asp Thr
385                 390                 395                 400
Gln His Ile Gln Gln Phe Tyr Asp Leu Leu Thr Gly Ser Met Glu Ile
                405                 410                 415
Ile Arg Gly Trp Ala Glu Lys Ile Pro Gly Phe Ala Asp Leu Pro Lys
            420                 425                 430
Ala Asp Gln Asp Leu Leu Phe Glu Ser Ala Phe Leu Glu Leu Phe Val
        435                 440                 445
Leu Arg Leu Ala Tyr Arg Ser Asn Pro Val Glu Gly Lys Leu Ile Phe
    450                 455                 460
Cys Asn Gly Val Val Leu His Arg Leu Gln Cys Val Arg Gly Phe Gly
465                 470                 475                 480
Glu Trp Ile Asp Ser Ile Val Glu Phe Ser Ser Asn Leu Gln Asn Met
                485                 490                 495
Asn Ile Asp Ile Ser Ala Phe Ser Cys Ile Ala Ala Leu Ala Met Val
            500                 505                 510
Thr Glu Arg His Gly Leu Lys Glu Pro Lys Arg Val Glu Glu Leu Gln
        515                 520                 525
Asn Lys Ile Val Asn Cys Leu Lys Asp His Val Thr Phe Asn Asn Gly
    530                 535                 540
Gly Leu Asn Arg Pro Asn Tyr Leu Ser Lys Leu Leu Gly Lys Leu Pro
545                 550                 555                 560
Glu Leu Arg Thr Leu Cys Thr Gln Gly Leu Gln Arg Ile Phe Tyr Leu
                565                 570                 575
Lys Leu Glu Asp Leu Val Pro Pro Ala Ile Ile Asp Lys Leu Phe
            580                 585                 590
Leu Asp Thr Leu Pro Phe
        595

<210> SEQ ID NO 78
<211> LENGTH: 598
<212> TYPE: PRT
<213> ORGANISM: Mouse

<400> SEQUENCE: 78

Met Pro Cys Val Gln Ala Gln Tyr Gly Ser Ser Pro Gln Gly Ala Ser
1               5                   10                  15
Pro Ala Ser Gln Ser Tyr Ser Tyr His Ser Ser Gly Glu Tyr Ser Ser
                20                  25                  30
Asp Phe Leu Thr Pro Glu Phe Val Lys Phe Ser Met Asp Leu Thr Asn
            35                  40                  45
Thr Glu Ile Thr Ala Thr Thr Ser Leu Pro Ser Phe Ser Thr Phe Met
```

```
                50                  55                  60
Asp Asn Tyr Ser Thr Gly Tyr Asp Val Lys Pro Cys Leu Tyr Gln
 65                  70                  75                  80

Met Pro Leu Ser Gly Gln Gln Ser Ser Ile Lys Val Glu Asp Ile Gln
                 85                  90                  95

Met His Asn Tyr Gln Gln His Ser His Leu Pro Pro Gln Ser Glu Glu
                100                 105                 110

Met Met Pro His Ser Gly Ser Val Tyr Tyr Lys Pro Ser Ser Pro Pro
                115                 120                 125

Thr Pro Ser Thr Pro Ser Phe Gln Val Gln His Ser Pro Met Trp Asp
130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
                180                 185                 190

Arg Phe Asp Gly Pro Leu His Val Pro Met Asn Pro Glu Pro Ala Gly
                195                 200                 205

Ser His His Val Val Asp Gly Gln Thr Phe Ala Val Pro Asn Pro Ile
                210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Ser Arg Gly Ser
                245                 250                 255

Pro Ser Asn Glu Gly Leu Cys Ala Val Cys Gly Asp Asn Ala Ala Cys
                260                 265                 270

Gln His Tyr Gly Val Arg Thr Cys Glu Gly Cys Lys Gly Phe Phe Lys
                275                 280                 285

Arg Thr Val Gln Lys Asn Ala Lys Tyr Val Cys Leu Ala Asn Lys Asn
290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
                325                 330                 335

Ser Leu Lys Gly Arg Arg Gly Arg Leu Pro Ser Lys Pro Lys Ser Pro
                340                 345                 350

Gln Asp Pro Ser Pro Ser Pro Val Ser Leu Ile Ser Ala Leu
                355                 360                 365

Val Arg Ala His Val Asp Ser Asn Pro Ala Met Thr Ser Leu Asp Tyr
370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
                420                 425                 430

Ala Asp Gln Asp Leu Leu Phe Glu Ser Ala Phe Leu Glu Leu Phe Val
                435                 440                 445

Leu Arg Leu Ala Tyr Arg Ser Asn Pro Val Glu Gly Lys Leu Ile Phe
                450                 455                 460

Cys Asn Gly Val Val Leu His Arg Leu Gln Cys Val Arg Gly Phe Gly
465                 470                 475                 480
```

-continued

```
Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Ala Leu Ala Met Val
            500                 505                 510

Thr Glu Arg His Gly Leu Lys Glu Pro Lys Arg Val Glu Glu Leu Gln
        515                 520                 525

Asn Lys Ile Val Asn Cys Leu Lys Asp His Val Thr Phe Asn Asn Gly
    530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Ala Ile Ile Asp Lys Leu Phe
            580                 585                 590

Leu Asp Thr Leu Pro Phe
        595

<210> SEQ ID NO 79
<211> LENGTH: 598
<212> TYPE: PRT
<213> ORGANISM: Human

<400> SEQUENCE: 79

Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
        35                  40                  45

Thr Glu Ile Thr Ala Thr Thr Ser Leu Pro Ser Phe Ser Thr Phe Met
    50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125

Thr Pro Thr Thr Pro Gly Phe Gln Val Gln His Ser Pro Met Trp Asp
    130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
        195                 200                 205

Ser His His Val Val Asp Gly Gln Thr Phe Ala Val Pro Asn Pro Ile
    210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Pro Ser Arg Gly Ser
```

```
                245                 250                 255
Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
            275                 280                 285

Arg Thr Val Gln Lys Asn Ala Lys Tyr Val Cys Leu Ala Asn Lys Asn
            290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
                325                 330                 335

Ser Leu Lys Gly Arg Arg Gly Arg Leu Pro Ser Lys Pro Lys Ser Pro
                340                 345                 350

Gln Glu Pro Ser Pro Ser Pro Val Ser Leu Ile Ser Ala Leu
                355                 360                 365                       Leu

Val Arg Ala His Val Asp Ser Asn Pro Ala Met Thr Ser Leu Asp Tyr
            370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
            435                 440                 445

Leu Arg Leu Ala Tyr Arg Ser Asn Pro Val Glu Gly Lys Leu Ile Phe
        450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Ala Leu Ala Met Val
            500                 505                 510

Thr Glu Arg His Gly Leu Lys Glu Pro Lys Arg Val Glu Glu Leu Gln
        515                 520                 525

Asn Lys Ile Val Asn Cys Leu Lys Asp His Val Thr Phe Asn Asn Gly
        530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Ala Ile Ile Asp Lys Leu Phe
            580                 585                 590

Leu Asp Thr Leu Pro Phe
        595

<210> SEQ ID NO 80
<211> LENGTH: 598
<212> TYPE: PRT
<213> ORGANISM: Human

<400> SEQUENCE: 80

Met Pro Cys Val Gln Ala Gln Tyr Gly Ser Ser Pro Gln Gly Ala Ser
1               5                   10                  15
```

```
Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
            35                  40                  45

Thr Glu Ile Thr Ala Thr Thr Ser Leu Pro Ser Phe Ser Thr Phe Met
 50                  55                  60

Asp Asn Tyr Ser Thr Gly Tyr Asp Val Lys Pro Pro Cys Leu Tyr Gln
 65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
                100                 105                 110

Met Met Pro His Ser Gly Ser Val Tyr Tyr Lys Pro Ser Ser Pro Pro
                115                 120                 125

Thr Pro Thr Thr Pro Gly Phe Gln Val Gln His Ser Pro Met Trp Asp
 130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
                180                 185                 190

Arg Phe Asp Gly Pro Leu His Val Pro Met Asn Pro Glu Pro Ala Gly
                195                 200                 205

Ser His His Val Val Asp Gly Gln Thr Phe Ala Val Pro Asn Pro Ile
                210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Pro Ser Arg Gly Ser
                245                 250                 255

Pro Ser Asn Glu Gly Leu Cys Ala Val Cys Gly Asp Asn Ala Ala Cys
                260                 265                 270

Gln His Tyr Gly Val Arg Thr Cys Glu Gly Cys Lys Gly Phe Phe Lys
                275                 280                 285

Arg Thr Val Gln Lys Asn Ala Lys Tyr Val Cys Leu Ala Asn Lys Asn
                290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
                325                 330                 335

Ser Leu Lys Gly Arg Arg Gly Arg Leu Pro Ser Lys Pro Lys Ser Pro
                340                 345                 350

Gln Glu Pro Ser Pro Pro Ser Pro Pro Val Ser Leu Ile Ser Ala Leu
                355                 360                 365

Val Arg Ala His Val Asp Ser Asn Pro Ala Met Thr Ser Leu Asp Tyr
                370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
                420                 425                 430

Ala Asp Gln Asp Leu Leu Phe Glu Ser Ala Phe Leu Glu Leu Phe Val
```

-continued

```
                435                 440                 445
Leu Arg Leu Ala Tyr Arg Ser Asn Pro Val Glu Gly Lys Leu Ile Phe
    450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Ala Leu Ala Met Val
            500                 505                 510

Thr Glu Arg His Gly Leu Lys Glu Pro Lys Arg Val Glu Glu Leu Gln
        515                 520                 525

Asn Lys Ile Val Asn Cys Leu Lys Asp His Val Thr Phe Asn Asn Gly
    530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Ala Ile Ile Asp Lys Leu Phe
            580                 585                 590

Leu Asp Thr Leu Pro Phe
        595
```

<210> SEQ ID NO 81
<211> LENGTH: 598
<212> TYPE: PRT
<213> ORGANISM: Human

<400> SEQUENCE: 81

```
Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
        35                  40                  45

Thr Glu Ile Thr Ala Thr Thr Ser Leu Pro Ser Phe Ser Thr Phe Met
    50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125

Thr Pro Thr Thr Pro Gly Phe Gln Val Gln His Ser Pro Met Trp Asp
    130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
        195                 200                 205
```

```
Ser His His Val Val Asp Gly Gln Thr Phe Ala Val Pro Asn Pro Ile
210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Ser Arg Gly Ser
                245                 250                 255

Pro Ser Asn Glu Gly Leu Cys Ala Val Cys Gly Asp Asn Ala Ala Cys
                260                 265                 270

Gln His Tyr Gly Val Arg Thr Cys Glu Gly Cys Lys Gly Phe Phe Lys
            275                 280                 285

Arg Thr Val Gln Lys Asn Ala Lys Tyr Val Cys Leu Ala Asn Lys Asn
290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
                325                 330                 335

Ser Leu Lys Gly Arg Arg Gly Arg Leu Pro Ser Lys Pro Lys Ser Pro
                340                 345                 350

Gln Glu Pro Ser Pro Ser Pro Val Ser Leu Ile Ser Ala Leu
            355                 360                 365

Val Arg Ala His Val Asp Ser Asn Pro Ala Met Thr Ser Leu Asp Tyr
370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
            405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
            435                 440                 445

Leu Arg Leu Ala Tyr Arg Ser Asn Pro Val Glu Gly Lys Leu Ile Phe
450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Ala Leu Ala Met Val
            500                 505                 510

Thr Glu Arg His Gly Leu Lys Glu Pro Lys Arg Val Glu Glu Leu Gln
            515                 520                 525

Asn Lys Ile Val Asn Cys Leu Lys Asp His Val Thr Phe Asn Asn Gly
530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Ala Ile Ile Asp Lys Leu Phe
                580                 585                 590

Leu Asp Thr Leu Pro Phe
            595

<210> SEQ ID NO 82
<211> LENGTH: 598
<212> TYPE: PRT
```

-continued

<213> ORGANISM: Rat

<400> SEQUENCE: 82

```
Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
        35                  40                  45

Thr Glu Ile Thr Ala Thr Thr Ser Leu Pro Ser Phe Ser Thr Phe Met
50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125

Thr Pro Ser Thr Pro Gly Phe Gln Val Gln His Ser Pro Met Trp Asp
    130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Arg Pro Gly Thr Pro Val Ser Ser Cys Gln Met
            180                 185                 190

Arg Phe Asp Gly Pro Leu His Val Pro Met Asn Pro Glu Pro Ala Gly
        195                 200                 205

Ser His His Val Val Asp Gly Gln Thr Phe Ala Val Pro Asn Pro Ile
    210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Ser Arg Gly Ser
                245                 250                 255

Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
        275                 280                 285

Arg Thr Val Gln Lys Asn Ala Lys Tyr Val Cys Leu Ala Asn Lys Asn
    290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
                325                 330                 335

Ser Leu Lys Gly Arg Arg Gly Arg Leu Pro Ser Lys Pro Lys Ser Pro
            340                 345                 350

Gln Asp Pro Ser Pro Pro Ser Pro Val Ser Leu Ile Ser Ala Leu
        355                 360                 365

Val Arg Ala His Val Asp Ser Asn Pro Ala Met Thr Ser Leu Asp Tyr
    370                 375                 380

Ser Arg Phe Gln Ala Asn Pro Asp Tyr Gln Met Ser Gly Asp Asp Thr
385                 390                 395                 400
```

```
Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
        435                 440                 445

Leu Arg Leu Ala Tyr Arg Ser Asn Pro Val Glu Gly Lys Leu Ile Phe
450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Ala Leu Ala Met Val
                500                 505                 510

Thr Glu Arg His Gly Leu Lys Glu Pro Lys Arg Val Glu Glu Leu Gln
            515                 520                 525

Asn Lys Ile Val Asn Cys Leu Lys Asp His Val Thr Phe Asn Asn Gly
530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Ala Ile Ile Asp Lys Leu Phe
                580                 585                 590

Leu Asp Thr Leu Pro Phe
            595

<210> SEQ ID NO 83
<211> LENGTH: 598
<212> TYPE: PRT
<213> ORGANISM: Human

<400> SEQUENCE: 83

Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
        35                  40                  45

Thr Glu Ile Thr Ala Thr Thr Ser Leu Pro Ser Phe Ser Thr Phe Met
    50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125

Thr Pro Thr Thr Pro Gly Phe Gln Val Gln His Ser Pro Met Trp Asp
    130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175
```

-continued

```
Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
            195                 200                 205

Ser His His Val Val Asp Gly Gln Thr Phe Ala Val Pro Asn Pro Ile
            210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Ser Arg Gly Ser
            245                 250                 255

Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
            275                 280                 285

Arg Thr Val Gln Lys Asn Ala Lys Tyr Val Cys Leu Ala Asn Lys Asn
            290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
            325                 330                 335

Ser Leu Lys Gly Arg Arg Gly Arg Leu Pro Ser Lys Pro Lys Ser Pro
            340                 345                 350

Gln Glu Pro Ser Pro Pro Ser Pro Val Ser Leu Ile Ser Ala Leu
            355                 360                 365

Val Arg Ala His Val Asp Ser Asn Pro Ala Met Thr Ser Leu Asp Tyr
            370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
            405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
            435                 440                 445

Leu Arg Leu Ala Tyr Arg Ser Asn Pro Val Glu Gly Lys Leu Ile Phe
            450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
            485                 490                 495

Asn Ile Asp Ile Ser Ala Phe Ser Cys Ile Ala Ala Leu Ala Met Val
            500                 505                 510

Thr Glu Arg His Gly Leu Lys Glu Pro Lys Arg Val Glu Glu Leu Gln
            515                 520                 525

Asn Lys Ile Val Asn Cys Leu Lys Asp His Val Thr Phe Asn Asn Gly
            530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
            565                 570                 575

Lys Leu Glu Asp Leu Val Pro Pro Pro Ala Ile Ile Asp Lys Leu Phe
            580                 585                 590
```

Leu Asp Thr Leu Pro Phe
        595

<210> SEQ ID NO 84
<211> LENGTH: 577
<212> TYPE: PRT
<213> ORGANISM: Frog

<400> SEQUENCE: 84

Met Pro Cys Ile Gln Ala Gln His Gly Ser Leu Ser Gln Cys Ala Gly
1               5                   10                  15

Pro Cys Asp Asn Tyr Val Pro Asp Ile Leu Asn Ser Glu Phe Gly Lys
            20                  25                  30

Phe Thr Met Asp Leu Val Asn Ser Glu Ile Ala Ala Ser Thr Ser Leu
        35                  40                  45

Pro Ser Phe Ser Thr Phe Met Asp Gly Tyr Thr Gly Glu Phe Asp Ala
    50                  55                  60

Phe Leu Tyr Gln Ile Pro Ser Ser Asn Gln Ser Ser Leu Lys Val
65                  70                  75                  80

Glu Glu Phe Gln Val Phe Gly Cys Tyr Pro Gly Ser Phe Thr Asn Gln
                85                  90                  95

Leu Asp Glu Thr Met Ser Ser Gly Ser Asp Tyr Tyr Gly Ser Pro
            100                 105                 110

Cys Ser Ile Pro Ser Pro Ser Thr Pro Gly Phe Gln Asn Pro Gln Leu
        115                 120                 125

Pro Thr Trp Glu Cys Ser Tyr Gly Ala Tyr Ser Pro Thr Gln Asn Tyr
    130                 135                 140

Asp Asn Met Arg His Trp Thr Glu Gln Gln Lys Asn Ser Ile Ser Gln
145                 150                 155                 160

Gln Thr Phe Phe Ser Phe Gly Thr Pro Ala His Ser Pro Asn Met Ala
                165                 170                 175

Ala Asn Pro Leu Lys Ile Ala Pro Ala Thr His Arg Leu Asp Gln Gln
            180                 185                 190

Leu Val Asp Thr Asp Val Phe Ala Leu Ala Gln Asn Ser Ser Ala Gly
        195                 200                 205

Phe Pro Ala Val Pro Leu Gly Gln Ala Pro Gly Val Leu Asp Ser Ser
    210                 215                 220

Val Leu Leu Asp Ser Pro Leu Ser Pro Ser Lys Thr Arg Ser Pro Ser
225                 230                 235                 240

Ser Asn Glu Gly Arg Cys Ala Val Cys Gly Asp Asn Ala Ser Cys Gln
                245                 250                 255

His Tyr Gly Val Arg Thr Cys Glu Gly Cys Lys Gly Phe Phe Lys Arg
            260                 265                 270

Thr Val Gln Lys Asn Ala Lys Tyr Ile Cys Leu Ala Asn Lys Asp Cys
        275                 280                 285

Pro Val Asp Lys Arg Arg Arg Asn Arg Cys Gln Phe Cys Arg Phe Gln
    290                 295                 300

Lys Cys Leu Val Val Gly Met Val Lys Glu Val Val Arg Thr Asp Ser
305                 310                 315                 320

Leu Lys Gly Arg Arg Gly Arg Leu Pro Ser Lys Pro Lys Gln Ile Ala
                325                 330                 335

Glu Ser Ser Pro Val Asp Leu Ile Asn Ser Leu Val Arg Ala His Ile
            340                 345                 350

Asp Ser Ile Pro Ser Ser Lys Leu Asp Tyr Ser Lys Phe Gln Glu
        355                 360                 365

Thr Val Pro Leu Gln Leu Glu Lys Glu Ser Ser Val Asp Val Gln Gln
    370                 375                 380

Phe Tyr Asp Leu Leu Ser Gly Ser Leu Glu Val Ile Arg Lys Trp Ala
385                 390                 395                 400

Glu Lys Ile Gln Gly Phe Val Asp Leu Pro Lys Glu Asp Gln Asp Leu
                405                 410                 415

Leu Leu Glu Ser Ala Phe Leu Glu Leu Phe Ile Leu Arg Leu Ala Tyr
            420                 425                 430

Arg Ser Arg Pro Glu Glu Gly Lys Leu Ile Phe Cys Asn Gly Val Val
        435                 440                 445

Leu His Arg Thr Gln Cys Val Arg Gly Phe Gly Glu Trp Ile Asp Ser
    450                 455                 460

Ile Ile Glu Phe Ser His Ser Leu Gln Arg Met Asn Ile Asp Val Pro
465                 470                 475                 480

Ser Phe Ser Cys Leu Ser Ala Leu Val Ile Val Thr Asp Arg His Gly
                485                 490                 495

Leu Lys Glu Pro Lys Lys Val Glu Glu Leu Gln Ser Gln Ile Ile Asn
            500                 505                 510

Cys Leu Lys Glu His Ile Pro Ser Ser Met Asn Glu Gln Asn Arg Pro
        515                 520                 525

Asn Cys Leu Ser Lys Leu Leu Gly Lys Leu Pro Glu Leu Arg Thr Leu
    530                 535                 540

Cys Thr Gln Gly Leu Gln Arg Ile Phe Tyr Leu Lys Leu Glu Asp Leu
545                 550                 555                 560

Val Pro Pro Pro Ile Val Asp Lys Ile Phe Met Asp Thr Leu Pro
                565                 570                 575

Phe

<210> SEQ ID NO 85
<211> LENGTH: 41
<212> TYPE: PRT
<213> ORGANISM: Zebrafish

<400> SEQUENCE: 85

Val Gln Lys Gly Ser Lys Tyr Val Cys Leu Ala Asn Lys Asn Cys Pro
1               5                   10                  15

Val Asp Lys Arg Arg Asn Arg Cys Gln Tyr Cys Arg Phe Gln Lys
            20                  25                  30

Cys Leu Val Val Gly Met Val Lys Glu
            35                  40

<210> SEQ ID NO 86
<211> LENGTH: 42
<212> TYPE: PRT
<213> ORGANISM: Sea lamprey

<400> SEQUENCE: 86

Val Gln Lys Gly Ser Lys Tyr Val Cys Leu Ala Asn Lys Asn Cys Pro
1               5                   10                  15

Ile Asp Lys Arg Arg Asn Arg Cys Gln Tyr Cys Arg Phe Gln Lys
            20                  25                  30

Cys Leu Val Val Gly Met Val Lys Glu Val
            35                  40

<210> SEQ ID NO 87
<211> LENGTH: 598

```
<212> TYPE: PRT
<213> ORGANISM: Mouse

<400> SEQUENCE: 87

Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
                20                  25                  30

Asp Phe Leu Thr Pro Glu Phe Val Lys Phe Ser Met Asp Leu Thr Asn
            35                  40                  45

Thr Glu Ile Thr Ala Thr Thr Ser Leu Pro Ser Phe Ser Thr Phe Met
    50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125

Thr Pro Ser Thr Pro Ser Phe Gln Val Gln His Ser Pro Met Trp Asp
130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
        195                 200                 205

Ser His His Val Val Asp Gly Gln Thr Phe Ala Val Pro Asn Pro Ile
    210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Pro Ser Arg Gly Ser
                245                 250                 255

Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
        275                 280                 285

Arg Thr Val Gln Lys Asn Ala Lys Tyr Val Cys Leu Ala Asn Lys Asn
    290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
                325                 330                 335

Ser Leu Lys Gly Arg Arg Gly Arg Leu Pro Ser Lys Pro Lys Ser Pro
            340                 345                 350

Gln Asp Pro Ser Pro Pro Ser Pro Val Ser Leu Ile Ser Ala Leu
        355                 360                 365

Val Arg Ala His Val Asp Ser Asn Pro Ala Met Thr Ser Leu Asp Tyr
    370                 375                 380

Ser Arg Phe Gln Ala Asn Pro Asp Tyr Gln Met Ser Gly Asp Asp Thr
385                 390                 395                 400
```

```
Gln His Ile Gln Gln Phe Tyr Asp Leu Leu Thr Gly Ser Met Glu Ile
                405                 410                 415
Ile Arg Gly Trp Ala Glu Lys Ile Pro Gly Phe Ala Asp Leu Pro Lys
            420                 425                 430
Ala Asp Gln Asp Leu Leu Phe Glu Ser Ala Phe Leu Glu Leu Phe Val
        435                 440                 445
Leu Arg Leu Ala Tyr Arg Ser Asn Pro Val Glu Gly Lys Leu Ile Phe
    450                 455                 460
Cys Asn Gly Val Val Leu His Arg Leu Gln Cys Val Arg Gly Phe Gly
465                 470                 475                 480
Glu Trp Ile Asp Ser Ile Val Glu Phe Ser Ser Asn Leu Gln Asn Met
                485                 490                 495
Asn Ile Asp Ile Ser Ala Phe Ser Cys Ile Ala Ala Leu Ala Met Val
                500                 505                 510
Thr Glu Arg His Gly Leu Lys Glu Pro Lys Arg Val Glu Glu Leu Gln
            515                 520                 525
Asn Lys Ile Val Asn Cys Leu Lys Asp His Val Thr Phe Asn Asn Gly
        530                 535                 540
Gly Leu Asn Arg Pro Asn Tyr Leu Ser Lys Leu Leu Gly Lys Leu Pro
545                 550                 555                 560
Glu Leu Arg Thr Leu Cys Thr Gln Gly Leu Gln Arg Ile Phe Tyr Leu
                565                 570                 575
Lys Leu Glu Asp Leu Val Pro Pro Ala Ile Ile Asp Lys Leu Phe
            580                 585                 590
Leu Asp Thr Leu Pro Phe
        595

<210> SEQ ID NO 88
<211> LENGTH: 20
<212> TYPE: DNA
<213> ORGANISM: Human

<400> SEQUENCE: 88
cgcaagccac ataaacaagg                                            20

<210> SEQ ID NO 89
<211> LENGTH: 24
<212> TYPE: DNA
<213> ORGANISM: Artificial Sequence
<220> FEATURE:
<223> OTHER INFORMATION: Primer

<400> SEQUENCE: 89
gcattgcaac ctgtgcaaga ccac                                       24

<210> SEQ ID NO 90
<211> LENGTH: 24
<212> TYPE: DNA
<213> ORGANISM: Artificial Sequence
<220> FEATURE:
<223> OTHER INFORMATION: Primer

<400> SEQUENCE: 90
gtttgccctc gaaaaccgaa gagc                                       24

<210> SEQ ID NO 91
<211> LENGTH: 19
<212> TYPE: DNA
<213> ORGANISM: Artificial Sequence
```

-continued

```
<220> FEATURE:
<223> OTHER INFORMATION: Primer

<400> SEQUENCE: 91
aactctgctg aagccatgc                                                    19

<210> SEQ ID NO 92
<211> LENGTH: 20
<212> TYPE: DNA
<213> ORGANISM: Artificial Sequence
<220> FEATURE:
<223> OTHER INFORMATION: Primer

<400> SEQUENCE: 92
gagaagccct cttatgtcga                                                   20

<210> SEQ ID NO 93
<211> LENGTH: 26
<212> TYPE: DNA
<213> ORGANISM: Artificial Sequence
<220> FEATURE:
<223> OTHER INFORMATION: Primer

<400> SEQUENCE: 93
ctcgcctcaa ggagccagcc ccgctt                                            26

<210> SEQ ID NO 94
<211> LENGTH: 2799
<212> TYPE: DNA
<213> ORGANISM: Human

<400> SEQUENCE: 94
ggcacgaggg gcacattggc ggccagggcc agtccgcccg gcggctcgcg cacggctccg        60
cggtcccttt tgcctgtcca gccggccgcc tgtccctgct ccctccctcc gtgaggtgtc       120
cgggttccct tcgcccagct ctcccacccc tacccgaccc cggcgcccgg gctcccagag       180
ggaactgcac ttcggcagag ttgaatgaat gaagagagac gcggagaact cctaaggagg       240
agattggaca ggctggactc cccattgctt ttctaaaaat cttggaaact ttgtccttca       300
ttgaattacg acactgtcca cctttaattt cctcgaaaac gcctgtaact cggctgaagc       360
catgccttgt gttcaggcgc agtatgggtc ctcgcctcaa ggagccagcc ccgcttctca       420
gagctacagt taccactctt cgggagaata cagctccgat ttcttaactc cagagtttgt       480
caagtttagc atggacctca ccaacactga aatcactgcc accacttctc tccccagctt       540
cagtaccttt atggacaact acagcacagg ctacgacgtc aagccacctt gcttgtacca       600
aatgcccctg tccggacagc agtcctccat taaggtagaa gacattcaga tgcacaacta       660
ccagcaacac agccacctgc cccccagtc tgaggagatg atgccgcact ccgggtcggt        720
ttactacaag ccctcctcgc cccgacgcc caccacccg gcttccagg tgcagcacag          780 ccccatgtgg gacgacccgg gatctctcca caacttccac cagaactacg tggccactac       840
gcacatgatc gagcagagga aaacgccagt ctcccgcctc tccctcttct cctttaagca       900 atcgcccct ggcaccccgg tgtctagttg ccagatgcgc ttcgacgggc cctgcacgt        960 ccccatgaac ccggagcccg ccggcagcca ccacgtggtg gacgggcaga ccttcgctgt      1020
gcccaacccc attcgcaagc ccgcgtccat gggcttcccg gcctgcaga tcggccacgc       1080 gtctcagctg ctcgacacgc aggtgccctc accgccgtcg cggggctccc cctccaacga      1140
ggggctgtgc gctgtgtgtg gggacaacgc ggcctgccaa cactacggcg tgcgcacctg      1200
```

```
tgagggctgc aaaggcttct ttaagcgcac agtgcaaaaa aatgcaaaat acgtgtgttt    1260
agcaaataaa aactgcccag tggacaagcg tcgccggaat cgctgtcagt actgccgatt    1320
tcagaagtgc ctggctgttg ggatggtcaa agaagtggtt cgcacagaca gtttaaaagg    1380
ccggagaggt cgtttgccct cgaaaccgaa gagcccacag gagccctctc cccctttcgcc   1440
cccggtgagt ctgatcagtg ccctcgtcag ggcccatgtc gactccaacc cggctatgac    1500
cagcctggac tattccaggt tccaggcgaa ccctgactat caaatgagtg gagatgacac    1560
ccagcatatc cagcaattct atgatctcct gactggctcc atggagatca tccggggctg    1620
ggcagagaag atccctggct cgcagacct gcccaaagcc gaccaagacc tgcttttttga    1680
atcagctttc ttagaactgt ttgtccttcg attagcatac aggtccaacc cagtggaggg    1740
taaactcatc ttttgcaatg gggtggtctt gcacaggttg caatgcgttc gtggctttgg    1800
ggaatggatt gattccattg ttgaattctc ctccaacttg cagaatatga acatcgacat    1860
ttctgccttc tcctgcattg ctgccctggc tatggtcaca gagagacacg ggctcaagga    1920
acccaagaga gtggaagaac tgcaaaacaa gattgtaaat tgtctcaaag accacgtgac    1980
tttcaacaat gggggttga accgccccaa ttatttgtcc aaactgttgg ggaagctccc    2040
agaacttcgt acctttgca cagggggct acagcgcatt ttctacctga aattggaaga    2100
cttggtgcca ccgccagcaa taattgacaa acttttcctg gacactttac ctttctaaga    2160
cctcctccca agcacttcaa aggaactgga atgataatgg aaactgtcaa gaggggggcaa    2220
gtcacatggg cagagatagc cgtgtgagca gtctcagctc aagctgcccc ccatttctgt    2280
aaccctccta gccccccttga tccctaaaga aaacaaacaa acaaacaaaa actgttgcta    2340
tttcctaacc tgcaggcaga acctgaaagg gcatttttggc tccggggcat cctggattta    2400
gaacatggac tacacacaat acagtggtat aaacttttta ttctcagttt aaaaatcagt    2460
ttgttgttca gaagaaagat tgctataagg tataatggga aatgtttggc catgcttggt    2520
tgttgcagtt cagacaaatg taacacacac acacatacac acacacacac acacagagac    2580
acatcttaag gggacccaca agtattgccc tttaacaaga cttcaaagtt ttctgctgta    2640
aagaaagctg taatatatag taaaactaaa tgttgcgtgg gtggcatgag ttgaagaagg    2700
caaaggcttg taaatttacc caatgcagtt tggcttttta aattattttg tgcctatttta   2760
tgaataaata ttcaaaattc taaaaaaaaa aaaaaaaa                           2799
```

<210> SEQ ID NO 95
<211> LENGTH: 21
<212> TYPE: DNA
<213> ORGANISM: Human

<400> SEQUENCE: 95
actgcatggg ctgcatctac t                                              21

<210> SEQ ID NO 96
<211> LENGTH: 22
<212> TYPE: DNA
<213> ORGANISM: Human

<400> SEQUENCE: 96
agcttcctgt gtctgtatt ca                                              22

<210> SEQ ID NO 97
<211> LENGTH: 22
<212> TYPE: DNA
<213> ORGANISM: Human

```
<400> SEQUENCE: 97
cctaccttca gccgagttac ag                                              22

<210> SEQ ID NO 98
<211> LENGTH: 22
<212> TYPE: DNA
<213> ORGANISM: Human

<400> SEQUENCE: 98
gacccaggct gagtgtgtta tc                                              22

<210> SEQ ID NO 99
<211> LENGTH: 21
<212> TYPE: DNA
<213> ORGANISM: Human

<400> SEQUENCE: 99
ggtggaagtt gtggagagat c                                               21

<210> SEQ ID NO 100
<211> LENGTH: 22
<212> TYPE: DNA
<213> ORGANISM: Human

<400> SEQUENCE: 100
atctctccac aacttccacc ag                                              22

<210> SEQ ID NO 101
<211> LENGTH: 22
<212> TYPE: DNA
<213> ORGANISM: Human

<400> SEQUENCE: 101
ctgcttccct ttctcagaca cc                                              22

<210> SEQ ID NO 102
<211> LENGTH: 22
<212> TYPE: DNA
<213> ORGANISM: Human

<400> SEQUENCE: 102
tcgtagaccc cagtcacata ac                                              22

<210> SEQ ID NO 103
<211> LENGTH: 22
<212> TYPE: DNA
<213> ORGANISM: Human

<400> SEQUENCE: 103
atgtcttcct ccaaatgggt cg                                              22

<210> SEQ ID NO 104
<211> LENGTH: 22
<212> TYPE: DNA
<213> ORGANISM: Human

<400> SEQUENCE: 104
aatgcttcta gtcagtgaag gc                                              22

<210> SEQ ID NO 105
<211> LENGTH: 22
<212> TYPE: DNA
```

<213> ORGANISM: Human

<400> SEQUENCE: 105
gccagcttct taccctggaa ta                                        22

<210> SEQ ID NO 106
<211> LENGTH: 22
<212> TYPE: DNA
<213> ORGANISM: Human

<400> SEQUENCE: 106
attccagttc caggcgaacc ct                                        22

<210> SEQ ID NO 107
<211> LENGTH: 22
<212> TYPE: DNA
<213> ORGANISM: Human

<400> SEQUENCE: 107
gtctcctccc tcccttatta cc                                        22

<210> SEQ ID NO 108
<211> LENGTH: 21
<212> TYPE: DNA
<213> ORGANISM: Human

<400> SEQUENCE: 108
aattgcaggt ccaacccagt g                                         21

<210> SEQ ID NO 109
<211> LENGTH: 21
<212> TYPE: DNA
<213> ORGANISM: Human

<400> SEQUENCE: 109
tgcagtactg acctgtgacc a                                         21

<210> SEQ ID NO 110
<211> LENGTH: 20
<212> TYPE: DNA
<213> ORGANISM: Human

<400> SEQUENCE: 110
gtcacaggtc agtactgcag                                           20

<210> SEQ ID NO 111
<211> LENGTH: 21
<212> TYPE: DNA
<213> ORGANISM: Human

<400> SEQUENCE: 111
ggaggtctta caaaggtaaa g                                         21

<210> SEQ ID NO 112
<211> LENGTH: 20
<212> TYPE: DNA
<213> ORGANISM: Human

<400> SEQUENCE: 112
gacaaacttt tcctggacac                                           20

<210> SEQ ID NO 113
<211> LENGTH: 20

```
<212> TYPE: DNA
<213> ORGANISM: Human

<400> SEQUENCE: 113
cactgtattg tgtgtagtcc                                              20

<210> SEQ ID NO 114
<211> LENGTH: 19
<212> TYPE: DNA
<213> ORGANISM: Human

<400> SEQUENCE: 114 aaagggatg aaccgggta                                                19

<210> SEQ ID NO 115
<211> LENGTH: 20
<212> TYPE: DNA
<213> ORGANISM: Human

<400> SEQUENCE: 115
ttttccgaaa gaggtgtgac                                              20

<210> SEQ ID NO 116
<211> LENGTH: 19
<212> TYPE: DNA
<213> ORGANISM: Human

<400> SEQUENCE: 116
cgaccaagac ctgcttttg                                               19

<210> SEQ ID NO 117
<211> LENGTH: 19
<212> TYPE: DNA
<213> ORGANISM: Human

<400> SEQUENCE: 117
taggtttccc ttcctccct                                               19

<210> SEQ ID NO 118
<211> LENGTH: 20
<212> TYPE: DNA
<213> ORGANISM: Human

<400> SEQUENCE: 118
ccagggacat tgcttaacat                                              20

<210> SEQ ID NO 119
<211> LENGTH: 20
<212> TYPE: DNA
<213> ORGANISM: Human

<400> SEQUENCE: 119
gagcaggatt tgtaaccctg                                              20

<210> SEQ ID NO 120
<211> LENGTH: 19
<212> TYPE: DNA
<213> ORGANISM: Human

<400> SEQUENCE: 120
tggagacact gaacgggta                                               19

<210> SEQ ID NO 121
```

-continued

```
<211> LENGTH: 20
<212> TYPE: DNA
<213> ORGANISM: Human

<400> SEQUENCE: 121
tgaaaagttt tgagatggag                                              20

<210> SEQ ID NO 122
<211> LENGTH: 20
<212> TYPE: DNA
<213> ORGANISM: Human

<400> SEQUENCE: 122
tcctaacctg caggcagaac                                              20

<210> SEQ ID NO 123
<211> LENGTH: 20
<212> TYPE: DNA
<213> ORGANISM: Human

<400> SEQUENCE: 123
ctgaactgca acaaccaagc                                              20

<210> SEQ ID NO 124
<211> LENGTH: 18
<212> TYPE: DNA
<213> ORGANISM: Human

<400> SEQUENCE: 124
gcggtccctt tggctggc                                                18
```